(12) United States Patent
Suzuki et al.

(10) Patent No.: US 9,150,551 B2
(45) Date of Patent: *Oct. 6, 2015

(54) CARBAZOLE COMPOUND, LIGHT-EMITTING ELEMENT MATERIAL, ORGANIC SEMICONDUCTOR MATERIAL, LIGHT-EMITTING ELEMENT, LIGHT-EMITTING DEVICE, LIGHTING DEVICE, AND ELECTRONIC DEVICE

(75) Inventors: Hiroki Suzuki, Kanagawa (JP); Harue Osaka, Kanagawa (JP); Tsunenori Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 1009 days.

This patent is subject to a terminal disclaimer.

(21) Appl. No.: 13/282,722

(22) Filed: Oct. 27, 2011

(65) Prior Publication Data

US 2012/0104370 A1    May 3, 2012

(30) Foreign Application Priority Data

Oct. 29, 2010 (JP) .................... 2010-243133

(51) Int. Cl.
| | |
|---|---|
| *H01L 51/50* | (2006.01) |
| *C07D 407/14* | (2006.01) |
| *C07D 409/14* | (2006.01) |
| *C07D 407/10* | (2006.01) |
| *C07D 209/82* | (2006.01) |
| *C07D 409/10* | (2006.01) |
| *C07D 405/04* | (2006.01) |

(Continued)

(52) U.S. Cl.
CPC ............ *C07D 405/04* (2013.01); *C07D 405/14* (2013.01); *C07D 409/04* (2013.01); *C07D 409/14* (2013.01); *H01L 51/0072* (2013.01); *H01L 51/0073* (2013.01); *H01L 51/5012* (2013.01)

(58) Field of Classification Search
None
See application file for complete search history.

(56) References Cited

U.S. PATENT DOCUMENTS

| 8,039,122 B2 | 10/2011 | Kawakami et al. |
| 8,247,089 B2 | 8/2012 | Otsu et al. |

(Continued)

FOREIGN PATENT DOCUMENTS

| EP | 2 395 573 A1 | 12/2011 |
| EP | 2 479 814 A1 | 7/2012 |

(Continued)

OTHER PUBLICATIONS

Goldsmith, C.R. et al., "C-H Bond Activation by a Ferric Methoxide Complex: Modeling the Rate—Determining Step in the Mechanism of Lipoxygenase," J. Am. Chem. Soc., vol. 124, No. 1, Jan. 1, 2002, pp. 83-96.

(Continued)

*Primary Examiner* — J. L. Yang
(74) *Attorney, Agent, or Firm* — Husch Blackwell LLP

(57) ABSTRACT

A carbazole compound in which the 2-position of a dibenzofuran skeleton or a dibenzothiophene skeleton is bonded to the 3-position of a carbazole skeleton and nitrogen of the carbazolyl group is bonded to the 9- or 10-position of an anthracene skeleton directly or via a phenylene group was able to be synthesized. It was found out that the carbazole compound has an excellent carrier-transport property, favorable film quality, and a wide band gap, and can be suitably used as a light-emitting element material and an organic semiconductor material.

34 Claims, 16 Drawing Sheets

(51) Int. Cl.
    *C07D 405/14* (2006.01)
    *C07D 409/04* (2006.01)
    *H01L 51/00* (2006.01)

(56) References Cited

U.S. PATENT DOCUMENTS

| | | |
|---|---|---|
| 8,298,687 B2 | 10/2012 | Kawakami et al. |
| 8,603,647 B2 | 12/2013 | Kawakami et al. |
| 8,642,782 B2 * | 2/2014 | Suzuki et al. ............ 548/440 |
| 2009/0015140 A1 | 1/2009 | Kawakami et al. |
| 2010/0069647 A1 | 3/2010 | Suzuki et al. |
| 2011/0114928 A1 | 5/2011 | Suzuki et al. |
| 2011/0272687 A1 | 11/2011 | Katakura et al. |
| 2012/0061714 A1 | 3/2012 | Osaka et al. |
| 2012/0074390 A1 | 3/2012 | Seo et al. |

FOREIGN PATENT DOCUMENTS

| | | |
|---|---|---|
| JP | 2007-15933 | 1/2007 |
| JP | 2007-039431 A | 2/2007 |
| JP | 2007-288035 A | 11/2007 |
| JP | 2010-135467 A | 6/2010 |
| JP | 2010-168345 A | 8/2010 |
| JP | 2010/090077 | 8/2012 |
| WO | WO 2006/104221 A1 | 10/2006 |
| WO | WO 2010/005066 A1 | 1/2010 |

OTHER PUBLICATIONS

Ohnishi, T. et al, "A Method of Measuring an Energy Level," *High Molecular EL Materials Development of Light-Emitting High Molecular Compounds,* Kyoritsu Shuppan, Dec. 25, 2004, p. 64-67 (with English translation, pp. 1-3).

* cited by examiner

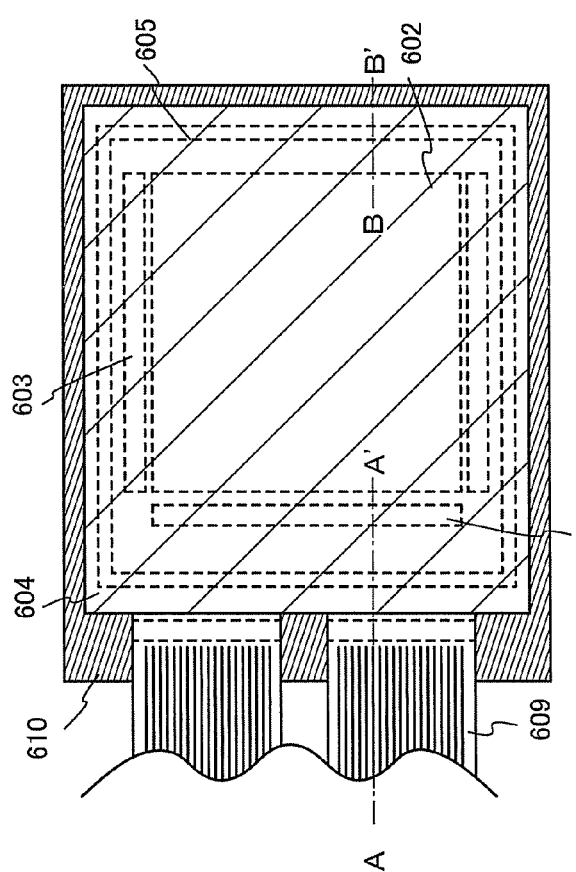
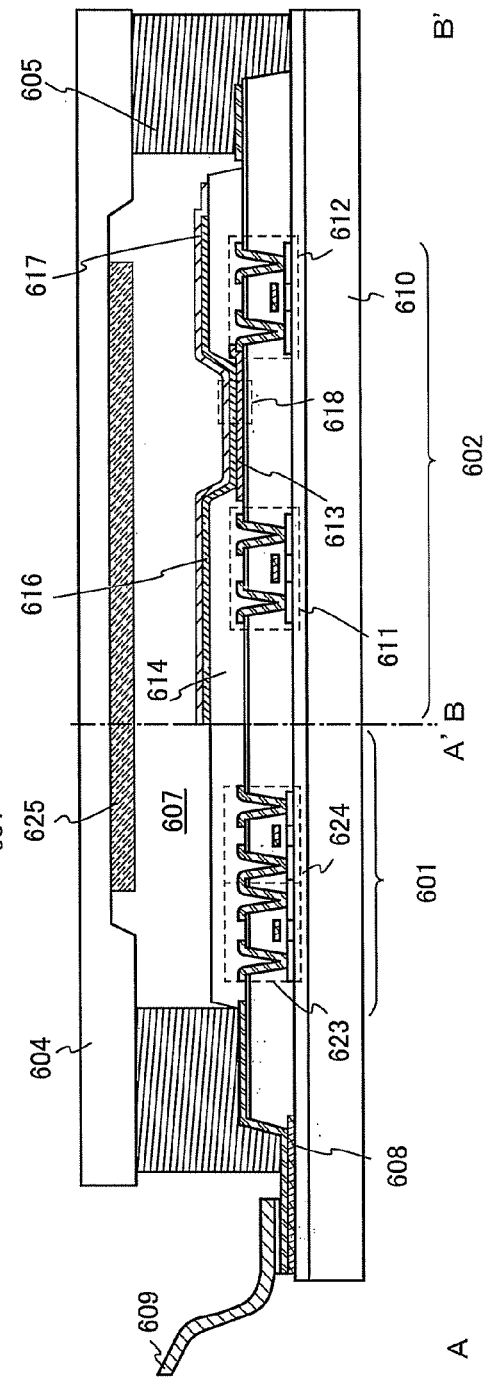
FIG. 3A
FIG. 3B

CARBAZOLE COMPOUND, LIGHT-EMITTING ELEMENT MATERIAL, ORGANIC SEMICONDUCTOR MATERIAL, LIGHT-EMITTING ELEMENT, LIGHT-EMITTING DEVICE, LIGHTING DEVICE, AND ELECTRONIC DEVICE

BACKGROUND OF THE INVENTION

1. Field of the Invention

The present invention relates to carbazole compounds that can be used as a light-emitting element material. The present invention further relates to light-emitting element materials, organic semiconductor materials, light-emitting elements, light-emitting devices, lighting devices, and electronic devices each using the carbazole compound.

2. Description of the Related Art

A display device using a light-emitting element (organic EL element) in which an organic compound is used as a light-emitting substance has been developed rapidly as a next generation lighting device or display device because it has advantages that such a light-emitting element can be manufactured to be thin and lightweight, has very high response speed with respect to an input signal, and has low power consumption.

In an organic EL element, when a voltage is applied between a pair of electrodes between which a light-emitting layer is interposed, electrons and holes injected from the electrodes are recombined to form an excited state, and when the excited state returns to a ground state, light is emitted. A wavelength of light emitted from a light-emitting substance is peculiar to the light-emitting substance; thus, by using different types of organic compounds as light-emitting substances, light-emitting elements which exhibit various wavelengths, i.e., various colors can be obtained.

In the case of a display device which is expected to display images, such as a display, in order to reproduce full-color images, at least light having wavelength components of three colors, i.e., red, green, and blue, is required to be obtained. In the case of a lighting device, in order to obtain high color rendering property, light having wavelength components thoroughly in the visible light region is ideally obtained. Actually, two or more kinds of light having different wavelengths are mixed to be used for lighting application in many cases. Note that it is known that by mixing light of three colors, red, green, and blue, white light emission having high color rendering property can be obtained.

Light emitted from a light-emitting substance is peculiar to the substance as described above. However, important performances as a light-emitting element, such as lifetime, power consumption, and emission efficiency, are not only dependent on a light-emitting substance but also greatly dependent on layers other than a light-emitting layer, an element structure, properties of the emission center substance and a host, compatibility between them, or the like. Therefore, it is true that many kinds of light-emitting element materials are necessary in order to show the growth of this field. For the above-described reasons, light-emitting element materials which have a variety of molecular structures have been proposed (for example, see Patent Document 1).

In particular, high-energy emission of blue light needs an emission center substance having a wide band gap and a host material having a wider band gap; therefore, it is difficult to say the variation of materials that can be used in fabricating a light-emitting element having favorable characteristics is sufficiently wide.

REFERENCE

Patent Document

[Patent Document 1] Japanese Published Patent Application No. 2007-15933

SUMMARY OF THE INVENTION

In view of the above, an object of one embodiment of the present invention is to provide a novel carbazole compound that can be used for a transport layer or as a host material or a light-emitting material of a light-emitting element.

Another object of one embodiment of the present invention is to provide a light-emitting element material using the above novel carbazole compound.

Another object of one embodiment of the present invention is to provide an organic semiconductor material using the above novel carbazole compound.

Another object of one embodiment of the present invention is to provide a light-emitting element with high light emission efficiency.

Another object of one embodiment of the present invention is to provide a light-emitting device, a lighting device, or an electronic device with low power consumption. Note that in one embodiment of the present invention, it is only necessary that at least one of the above-described objects is achieved.

The present inventors were able to synthesize a carbazole compound in which the 2-position of a dibenzofuran skeleton or a dibenzothiophene skeleton is bonded to the 3-position of a carbazole skeleton and nitrogen of the carbazolyl group is bonded to the 9- or 10-position of an anthracene skeleton directly or via a phenylene group. Further, the present inventors have found out that the carbazole compound has a high carrier-transport property and can be suitably used as a material of a light-emitting element and an organic semiconductor material.

That is, one embodiment of the present invention is a carbazole compound in which the 2-position of a dibenzofuran skeleton or a dibenzothiophene skeleton is bonded to the 3-position of a carbazole skeleton and nitrogen of the carbazolyl group is bonded to the 9- or 10-position of an anthracene skeleton directly or via a phenylene group.

Note that in the above-described carbazole compound, the anthracene skeleton and the dibenzofuran or dibenzothiophene skeleton may have a substituent. In the case where these skeletons has a substituent or substituents, the substituent(s) can be individually any of an alkyl group having 1 to 6 carbon atoms and an aryl group having 6 to 13 carbon atoms.

In addition, the carbazole skeleton in the above-described carbazole compound may further have a dibenzofuran-2-yl group or a dibenzothiophene-2-yl group at the 6-position of the carbazole skeleton. The dibenzofuran-2-yl group or dibenzothiophene-2-yl group may further have a substituent, and the substituent can be selected from any of an alkyl group having 1 to 6 carbon atoms and an aryl group having 6 to 13 carbon atoms. The substituent is preferably an aryl group in which case the amorphous property and the thermophysical property are improved. The substituent is preferably an alkyl group in which case the solubility in a solvent is improved and the purification is easier. However, it is preferable that the substituent be not included for easy synthesis.

The carbazole compound having any of such structures has a high carrier-transport property and can be suitably used as a host material or for a carrier-transport layer of a light-emitting element. Since the carbazole compound has a high carrier-transport property, a light-emitting element driven with a low driving voltage can be fabricated.

In addition, the carbazole compound has a wide band gap and thus can be suitably used as a host material in which an emission center substance that emits blue fluorescence is dispersed. Since the carbazole compound has a wide band gap, energy of carriers that are recombined in the host material can be effectively transported to the emission center substance; therefore, a light-emitting element with high emission efficiency can be fabricated.

Further, the carbazole compound having a wide band gap can be suitably used for a carrier-transport layer that is adjacent to a light-emitting layer containing an emission center substance that emits blue fluorescence without deactivating excitation energy of the emission center substance. Therefore, a light-emitting element with high emission efficiency can be fabricated.

The carbazole compound emits fluorescence with high quantum yield. Therefore, the carbazole compound can be used as a light-emitting material, and thus a light-emitting element with high emission efficiency can be fabricated.

The above-described carbazole compound is specifically described below. That is, another embodiment of the present invention is a carbazole compound represented by a general formula (G1) below.

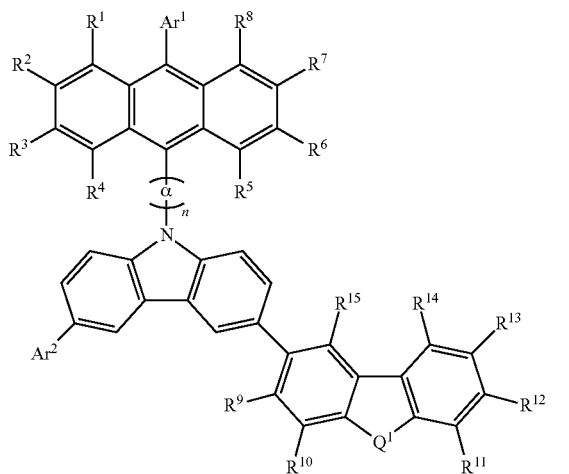

(G1)

In the formula, $Ar^1$ represents any of hydrogen and an aryl group having 6 to 13 carbon atoms, and $R^1$ to $R^{15}$ individually represent any of hydrogen, an alkyl group having 1 to 6 carbon atoms, and an aryl group having 6 to 13 carbon atoms. In addition, n is 0 or 1, α represents a group represented by a structural formula (α-1) or a structural formula (α-2) below. $Ar^2$ represents any of hydrogen, an alkyl group having 1 to 6 carbon atoms, an aryl group having 6 to 13 carbon atoms, and a group represented by a general formula (g1) below. $Q^1$ represents oxygen or sulfur.

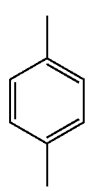

(α-1)

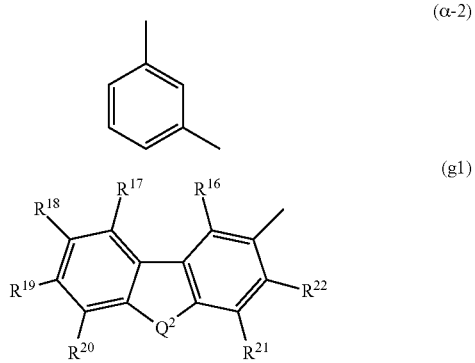

In the formula, $R^{16}$ to $R^{22}$ individually represent any of hydrogen, an alkyl group having 1 to 6 carbon atoms, and an aryl group having 6 to 13 carbon atoms. $Q^2$ represents oxygen or sulfur.

Note that n in the general formula (G1) is preferably 1 in which case a wide band gap material can be provided.

In addition, $Ar^2$ in the general formula (G1) is preferably hydrogen in which case a wide band gap material can be provided. Further, $Ar^2$ is preferably an aryl group having 6 to 13 carbon atoms or a group, represented by the general formula (g1) above in which case the carrier-transport property is high. The group represented by the general formula (g1) above is especially preferable.

Further, either or both $Q^1$ or/and $Q^2$ in the general formula (G1) is/are preferably oxygen in which case the band gap is wider.

That is, another structure of the present invention is a carbazole compound represented by a general formula (G2) below.

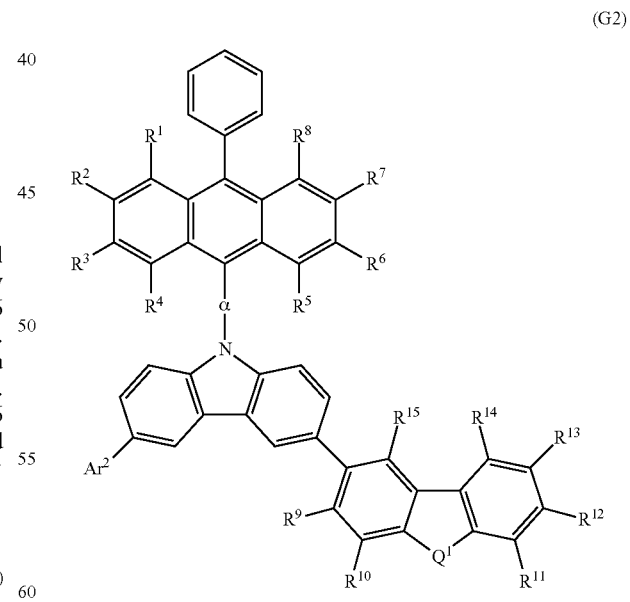

(G2)

In the formula, $R^1$ to $R^{15}$ individually represent any of hydrogen, an alkyl group having 1 to 6 carbon atoms, and an aryl group having 6 to 13 carbon atoms. In addition, α represents a group represented by a structural formula (α-1) or a structural formula (α-2) below. $Ar^2$ represents any of hydrogen, an alkyl group having 1 to 6 carbon atoms, an aryl group having 6 to 13 carbon atoms, and a group represented by a general formula (g1) below. $Q^1$ represents oxygen or sulfur.

(α-1)

(α-2)

(g1)

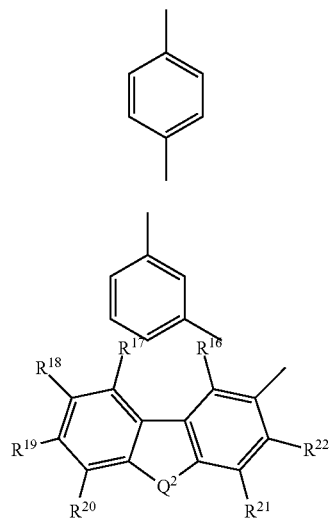

In the formula, $R^{16}$ to $R^{22}$ individually represent any of hydrogen, an alkyl group having 1 to 6 carbon atoms, and an aryl group having 6 to 13 carbon atoms. $Q^2$ represents oxygen or sulfur.

In the case where the anthracene skeleton has a substituent, the substitution site(s) of the substituent is/are preferably any one or a plurality of $R^2$, $R^3$, $R^6$, and $R^7$, and in the case where the dibenzofuran skeleton or dibenzothiophene skeleton has a substituent, the substitution site(s) of the substituent is/are preferably any one or a plurality of $R^{10}$, $R^{11}$, $R^{13}$, $R^{18}$, $R^{20}$, and $R^{21}$, for a reduction in cost of producing the substance owing to easiness of the synthesis and availability of the material.

That is, another structure of the present invention is a carbazole compound represented by a general formula (G3) below.

(G3)

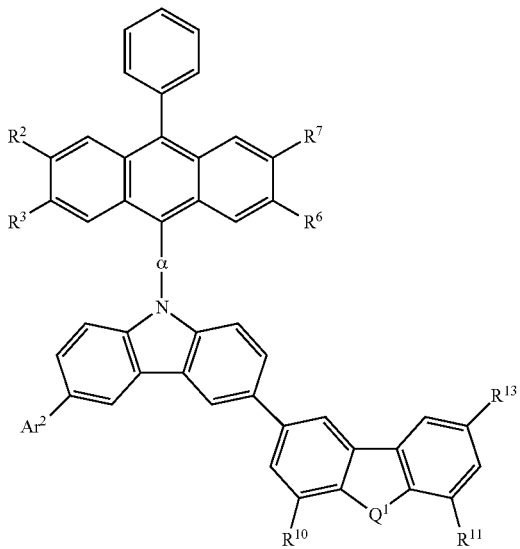

In the formula, $R^2$, $R^3$, $R^6$, $R^7$, $R^{10}$, $R^{11}$, and $R^{13}$ individually represent any of hydrogen, an alkyl group having 1 to 6 carbon atoms, and an aryl group having 6 to 13 carbon atoms. In addition, α represents a group represented by a structural formula (α-1) or a structural formula (α-2) below. $Ar^2$ represents any of hydrogen, an alkyl group having 1 to 6 carbon atoms, an aryl group having 6 to 13 carbon atoms, and a group represented by a general formula (g2) below. $Q^1$ represents oxygen or sulfur.

(α-1)

(α-2)

(g2)

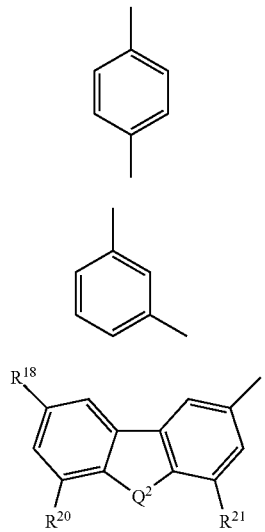

In the formula, $R^{18}$, $R^{20}$, and $R^{21}$ individually represent any of hydrogen, an alkyl group having 1 to 6 carbon atoms, and an aryl group having 6 to 13 carbon atoms. $Q^2$ represents oxygen or sulfur.

A dibenzofuran skeleton or a dibenzothiophene skeleton does not preferably include a substituent for higher solubility in a solvent and easier synthesis.

That is, another structure of the present invention is a carbazole compound represented by a general formula (G4) below.

(G4)

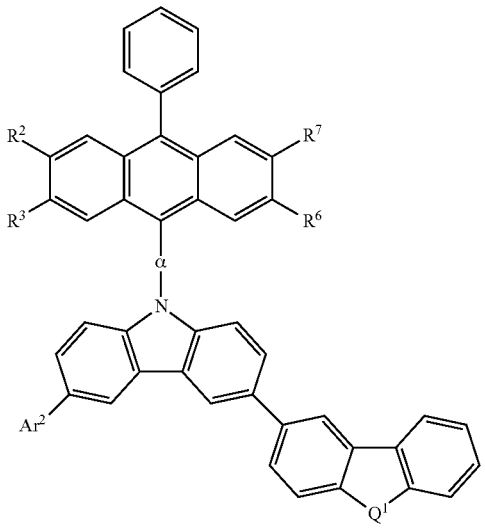

In the formula, $R^2$, $R^3$, $R^6$, and $R^7$ individually represent any of hydrogen, an alkyl group having 1 to 6 carbon atoms, and an aryl group having 6 to 13 carbon atoms. In addition, α represents a group represented by a structural formula (α-1) or a structural formula (α-2) below. Ar² represents any of hydrogen, an alkyl group having 1 to 6 carbon atoms, an aryl group having 6 to 13 carbon atoms, and a group represented by a general formula (g3) below. Q¹ represents oxygen or sulfur.

(α-1)

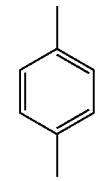

(α-2)

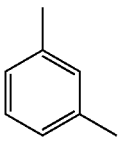

(g3)

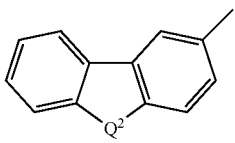

In the formula, Q² represents oxygen or sulfur.

All $R^1$ to $R^{22}$ are more preferably hydrogen for easier synthesis, availability of the material, and the like.

That is, another structure of the present invention is a carbazole compound represented by a general formula (G5) below.

(G5)

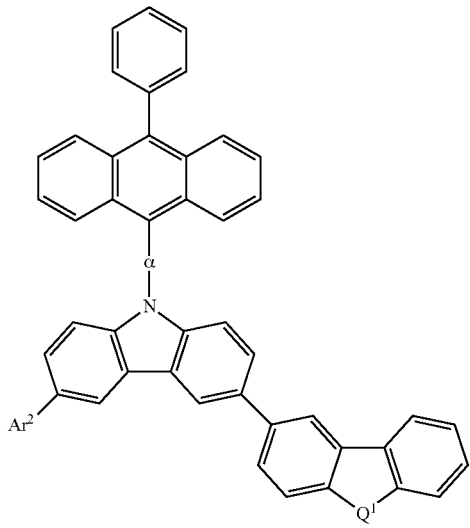

In the formula, Ar² represents any of hydrogen, an alkyl group having 1 to 6 carbon atoms, an aryl group having 6 to 13 carbon atoms, and a group represented by a general formula (g3) below. In addition, α represents a group represented by a structural formula (α-1) or a structural formula (α-2) below. Q¹ represents oxygen or sulfur.

(α-1)

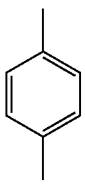

(α-2)

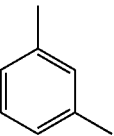

(g3)

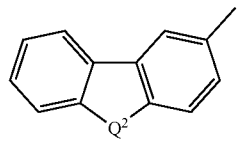

In the formula, Q² represents oxygen or sulfur.

In the general formula (G1), α is preferably a para-substituted phenylene group represented by the structural formula (α-1) for a higher carrier-transport property and a higher thermophysical property (Tg).

That is, another structure of the present invention is a carbazole compound represented by a general formula (G6) below.

(G6)

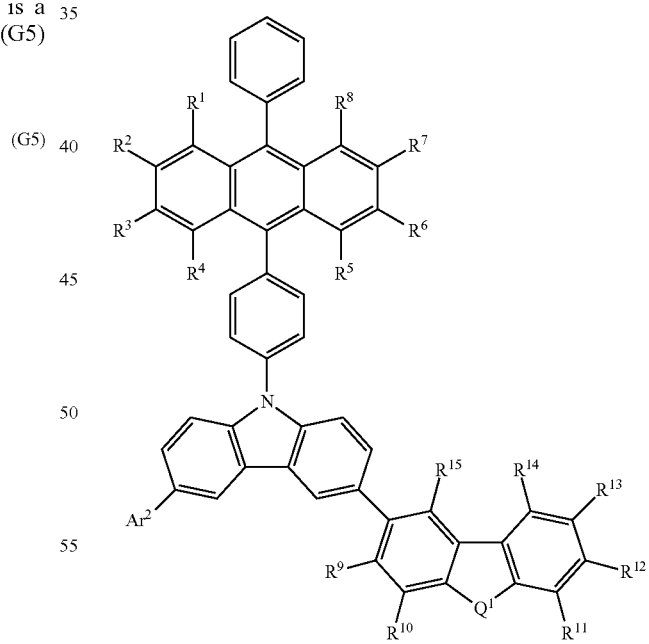

In the formula, $R^1$ to $R^{15}$ individually represent any of hydrogen, an alkyl group having 1 to 6 carbon atoms, and an aryl group having 6 to 13 carbon atoms. Ar² represents any of hydrogen, an alkyl group having 1 to 6 carbon atoms, an aryl group having 6 to 13 carbon atoms, and a group represented by a general formula (g1) below. Q¹ represents oxygen or sulfur.

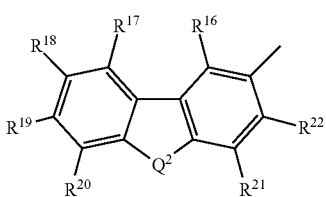

(g1)

In the formula, $R^{16}$ to $R^{22}$ individually represent any of hydrogen, an alkyl group having 1 to 6 carbon atoms, and an aryl group having 6 to 13 carbon atoms. $Q^2$ represents oxygen or sulfur.

In the case where the anthracene skeleton has a substituent, the substitution site(s) of the substituent is/are preferably any one or a plurality of $R^2$, $R^3$, $R^6$, and $R^7$, and in the case where the dibenzofuran skeleton or dibenzothiophene skeleton has a substituent, the substitution site(s) of the substituent is/are preferably any one or a plurality of $R^{10}$, $R^{11}$, $R^{13}$, $R^{18}$, $R^{20}$, and $R^{21}$, for a reduction in cost of producing the substance owing to easiness of the synthesis and availability of the material.

That is, another structure of the present invention is a carbazole compound represented by a general formula (G7) below.

(G7)

In the formula, $R^2$, $R^3$, $R^6$, $R^7$, $R^{10}$, $R^{11}$, and $R^{13}$ individually represent any of hydrogen, an alkyl group having 1 to 6 carbon atoms, and an aryl group having 6 to 13 carbon atoms. $Ar^2$ represents any of hydrogen, an alkyl group having 1 to 6 carbon atoms, an aryl group having 6 to 13 carbon atoms, and a group represented by a general formula (g2) below. $Q^1$ represents oxygen or sulfur.

(g2)

In the formula, $R^{18}$, $R^{20}$, and $R^{21}$ individually represent any of hydrogen, an alkyl group having 1 to 6 carbon atoms, and an aryl group having 6 to 13 carbon atoms. $Q^2$ represents oxygen or sulfur.

A dibenzofuran skeleton or a dibenzothiophene skeleton does not preferably include a substituent for higher solubility in a solvent and easier synthesis.

That is, another structure of the present invention is a carbazole compound represented by a general formula (G8) below.

(G8)

In the formula, $R^2$, $R^3$, $R^6$, and $R^7$ individually represent any of hydrogen, an alkyl group having 1 to 6 carbon atoms, and an aryl group having 6 to 13 carbon atoms. $Ar^2$ represents any of hydrogen, an alkyl group having 1 to 6 carbon atoms, an aryl group having 6 to 13 carbon atoms, and a group represented by a general formula (g3) below. $Q^1$ represents oxygen or sulfur.

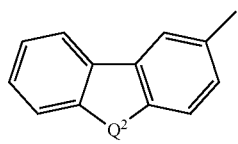

(g3)

In the formula, $Q^2$ represents oxygen or sulfur.

All $R^1$ to $R^{22}$ are more preferably hydrogen for easier synthesis, availability of the material, and the like.

That is, another structure of the present invention is a carbazole compound represented by a general formula (G9) below.

(G9)

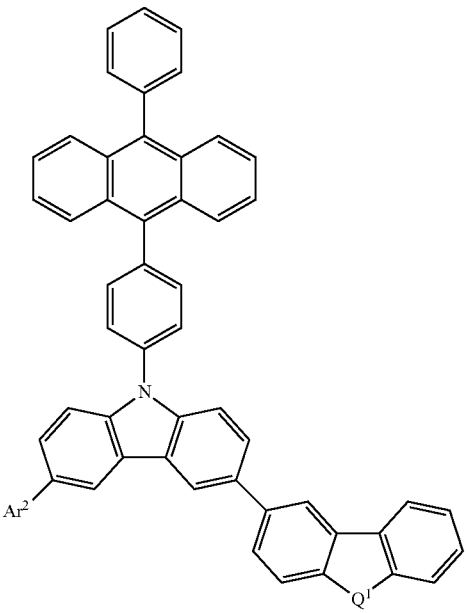

In the formula, $Ar^2$ represents any of hydrogen, an alkyl group having 1 to 6 carbon atoms, an aryl group having 6 to 13 carbon atoms, and a group represented by a general formula (g3) below. $Q^1$ represents oxygen or sulfur.

(g3)

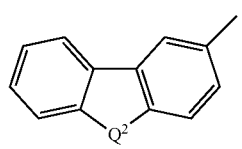

In the formula, $Q^2$ represents oxygen or sulfur.

The structure is preferably asymmetry for stable evaporation rate.

That is, another structure of the present invention is a carbazole compound represented by a general formula (G10) below.

(G10)

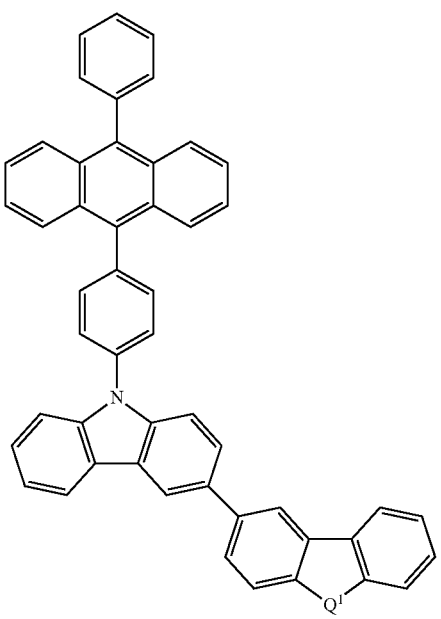

In the formula, $Q^1$ represents oxygen or sulfur.

For higher hole-injection property, a dibenzofuran skeleton or a dibenzothiophene skeleton is preferably bonded at both the 3-position and the 6-position of a carbazole group.

That is, another structure of the present invention is a carbazole compound represented by a general formula (G11) below.

(G11)

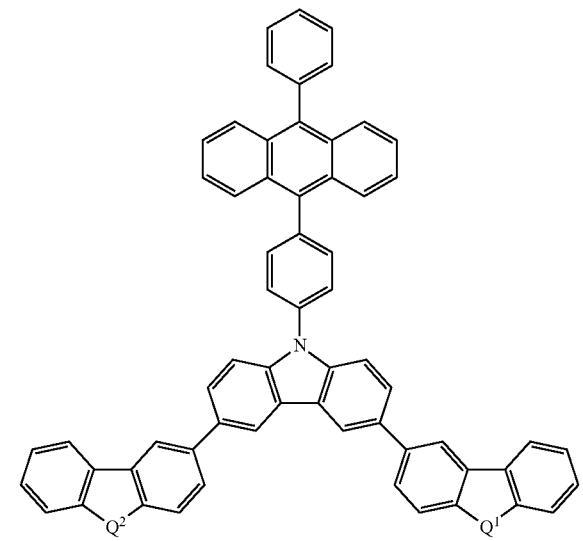

In the formula, $Q^1$ represents oxygen or sulfur and $Q^2$ represents oxygen or sulfur.

Another structure of the present invention is a carbazole compound represented by a structural formula below.

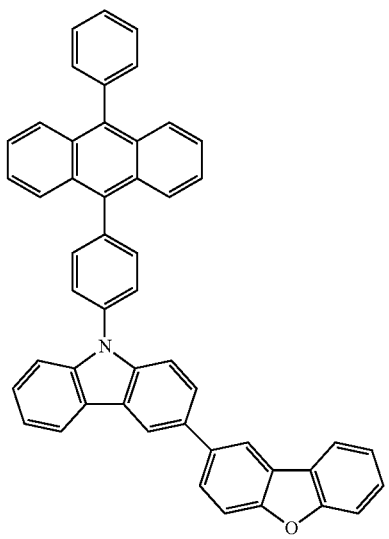 [SMILES: c1ccc(-c2c3ccccc3c(-c3ccc(-n4c5ccccc5c5cc(-c6ccc7oc8ccccc8c7c6)ccc54)cc3)c3ccccc23)cc1]

Another structure of the present invention is a carbazole compound represented by a structural formula below.

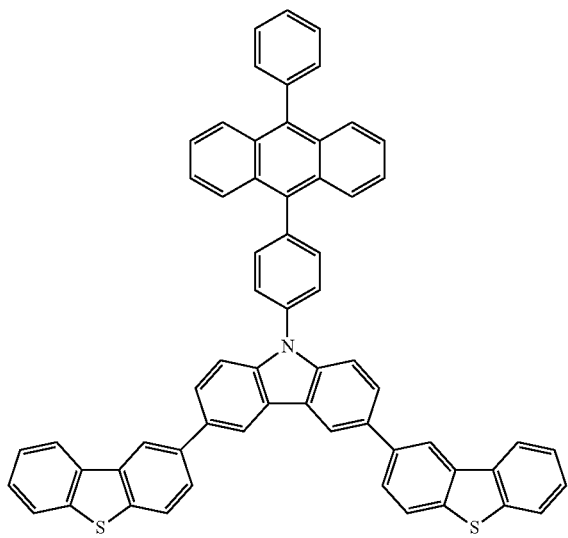 [SMILES: c1ccc(-c2c3ccccc3c(-c3ccc(-n4c5ccc(-c6ccc7sc8ccccc8c7c6)cc5c5cc(-c6ccc7sc8ccccc8c7c6)ccc54)cc3)c3ccccc23)cc1]

Another structure of the present invention is an organic semiconductor material containing any of the above-described carbazole compounds.

Another structure of the present invention is a light-emitting element material containing any of the above-described carbazole compounds.

Another structure of the present invention is a light-emitting element in which a layer containing an organic compound is interposed between a pair of electrodes, and the layer containing an organic compound contains any of the above-described carbazole compounds.

Another structure of the present invention is a light-emitting device including the above-described light-emitting element.

Another structure of the present invention is a lighting device including the above-described light-emitting element.

Another structure of the present invention is an electronic device including the above-described light-emitting element and a unit that controls the light-emitting element.

A carbazole compound having any of the above-described structures is a substance having both a high carrier-transport property and a wide energy gap, and thus can be used suitably for a transport layer or as a host material or a light-emitting substance of a light-emitting element. A light-emitting element using a light-emitting element material containing the carbazole compound can be a light-emitting element with high emission efficiency. In addition, a light-emitting element using a light-emitting element material containing the carbazole compound can be a light-emitting element driven with a low driving voltage. Further, a light-emitting element using a light-emitting element material containing the carbazole compound can be a light-emitting element having a long lifetime. The carbazole compound can also be used as an organic semiconductor material.

BRIEF DESCRIPTION OF THE DRAWINGS

FIGS. 3A and 3B are conceptual diagrams of an active matrix light-emitting device.

DETAILED DESCRIPTION OF THE INVENTION

Figure 1A:
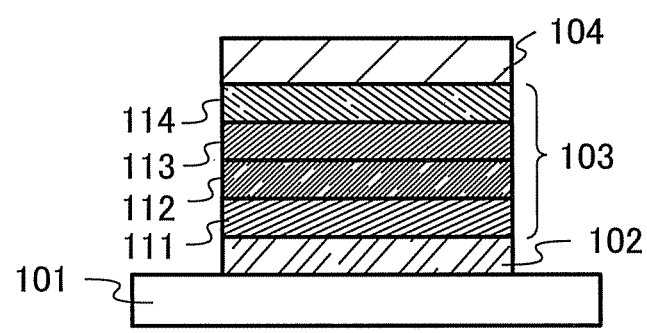
FIGS. 1A and 1B are conceptual diagrams of light-emitting elements.

Hereinafter, embodiments of the present invention are described. It is easily understood by those skilled in the art that modes and details disclosed herein can be modified in various ways without departing from the spirit and the scope of the present invention. Therefore, the present invention is not construed as being limited to description of the embodiments.

Embodiment 1

A carbazole compound in this embodiment is a carbazole compound in which the 2-position of a dibenzofuran skeleton or a dibenzothiophene skeleton is bonded to the 3-position of a carbazole skeleton and nitrogen of the carbazolyl group is bonded to the 9- or 10-position of an anthracene skeleton directly or via a phenylene group. In this carbazole compound, the anthracene skeleton and the dibenzofuran or dibenzothiophene skeleton may have a substituent. In the case where these skeletons has a substituent or substituents, the substituent(s) can be selected from any of an alkyl group having 1 to 6 carbon atoms and an aryl group having 6 to 13 carbon atoms.

In addition, the carbazole skeleton in the above-described carbazole compound may further have a dibenzofuran-2-yl group or a dibenzothiophene-2-yl group at the 6-position of the carbazole skeleton. The dibenzofuran-2-yl group or dibenzothiophene-2-yl group may further have a substituent, and the substituent can be selected from any of an alkyl group having 1 to 6 carbon atoms and an aryl group having 6 to 13 carbon atoms.

The above-described carbazole compound has a high carrier-transport property and can be suitably used as a material of a light-emitting element and an organic semiconductor material. In the case of being used as a material of a light-emitting element, since the carbazole compound has a high carrier-transport property, the carbazole compound can be suitably used as a host material or for a carrier-transport layer of a light-emitting element. Since the carbazole compound has a high carrier-transport property, a light-emitting element driven with a low driving voltage can be fabricated.

In addition, the carbazole compound has a wide band gap and thus can be suitably used as a host material in which an emission center substance that emits blue fluorescence is dispersed. Since the carbazole compound has a wide band gap, energy of carriers that are recombined in the host material can be effectively transported to the emission center substance; therefore, a light-emitting element with high emission efficiency can be fabricated. Note that the carbazole compound can be used as a host material in which an emission center substance that emits fluorescence with a wavelength longer than that of blue is dispersed.

Further, the carbazole compound having a wide band gap can be suitably used as a material used for a carrier-transport layer that is adjacent to a light-emitting layer containing an emission center substance that emits blue fluorescence without deactivating excitation energy of the emission center substance. Therefore, a light-emitting element with high emission efficiency can be fabricated. Needless to say, the carbazole compound can also be used as a material used for a carrier-transport layer that is adjacent to a light-emitting layer containing an emission center substance that emits fluorescence with a wavelength longer than that of blue.

The above-described carbazole compound can also be represented by a general formula (G1) below.

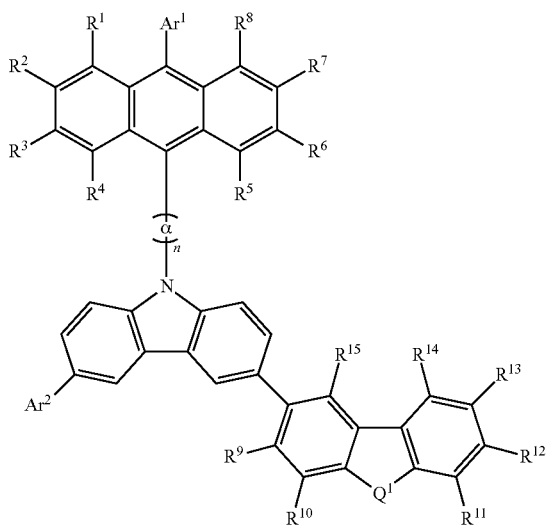

(G1)

In the formula, $Ar^1$ represents any of hydrogen and an aryl group having 6 to 13 carbon atoms, and $R^1$ to $R^{15}$ individually represent any of hydrogen, an alkyl group having 1 to 6 carbon atoms, and an aryl group having 6 to 13 carbon atoms. In addition, n is 0 or 1, α represents a group represented by a structural formula (α-1) or a structural formula (α-2) below. $Ar^2$ represents any of hydrogen, an alkyl group having 1 to 6 carbon atoms, an aryl group having 6 to 13 carbon atoms, and a group represented by a general formula (g1) below. $Q^1$ represents oxygen or sulfur.

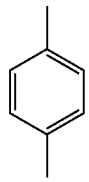

(α-1)

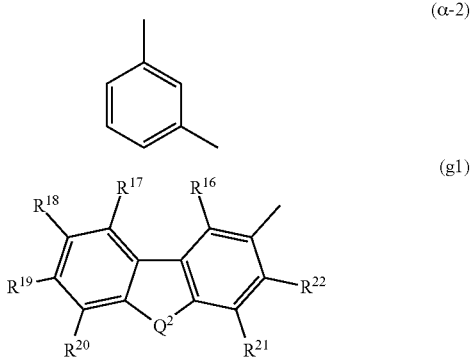

(α-2)

(g1)

In the formula, $R^{16}$ to $R^{22}$ individually represent any of hydrogen, an alkyl group having 1 to 6 carbon atoms, and an aryl group having 6 to 13 carbon atoms. $Q^2$ represents oxygen or sulfur.

When n in the general formula (G1) is 1, extension of the conjugation from an anthracene skeleton to a carbazole skeleton can be more effectively prevented, and a substance having a wide band gap can be provided.

In the case where the anthracene skeleton has a substituent, the substitution site(s) of the substituent is/are preferably any one or a plurality of $R^2$, $R^3$, $R^6$, and $R^7$, and in the case where the dibenzofuran skeleton or dibenzothiophene skeleton has a substituent, the substitution site(s) of the substituent is/are preferably any one or a plurality of $R^{10}$, $R^{11}$, $R^{13}$, $R^{18}$, $R^{20}$, and $R^{21}$, for a reduction in cost of producing the substance owing to easiness of the synthesis and availability of the material. For the same reasons, all $R^1$ to $R^{22}$ are more preferably hydrogen for easier synthesis, availability of the material, and the like.

The above-described substituents individually represent any of hydrogen, an alkyl group having 1 to 6 carbon atoms, and an aryl group having 6 to 13 carbon atoms. In the case of the alkyl group, a methyl group, an ethyl group, a propyl group, a butyl group, a tert-butyl group, a pentyl group, a hexyl group, a cyclohexyl group, or the like can be used. In the case of the aryl group, a phenyl group, a naphthyl group, a biphenyl group, or the like can be used. Such a substituent is preferably included for a more steric molecular structure and higher amorphous property. The substituent is preferably an alkyl group for such effects as higher solubility in an organic solvent, easier synthesis, easier deposition by a wet method, and the like.

In the general formula (G1), α is preferably a para-substituted phenylene group represented by the structural formula (α-1) for a higher carrier-transport property and a higher thermophysical property (Tg).

In the general formula (G1), α is preferably a meta-substituted phenylene group represented by the structural formula (α-2) for a more steric structure than a para-substituted phenylene group, higher amorphous property, and higher solubility.

In the formula, in the case where $Ar^2$ has a substituent, $Q^1$ and $Q^2$ are preferably the same element (the same substituents are preferably bonded to the 3- and 6-position of a carbazole skeleton) for easier synthesis.

In the formula, all $R^{16}$ to $R^{22}$ in $Ar^2$ are preferably hydrogen for solubility in an organic solvent and easier synthesis. In the case where $Ar^2$ has a substituent, the substituent is preferably an alkyl group for high solubility in an organic solvent.

Note that the carbazole compound represented by the general formula (G1) is a material with low symmetry in a molecule. Thus, the evaporation rate in evaporation can be stabilized, the thickness of a film can be easily controlled, and a light-emitting element with a stable quality can be provided.

The carbazole compound represented by the general formula (G1) is a so-called bipolar material having both an electron-transport property and a hole-transport property. By using a bipolar material for a light-emitting layer of a light-emitting element, localization of an emission region can be prevented, and a light-emitting element with high emission efficiency can be provided.

As specific examples of structures of the carbazole compound represented by the general formula (G1) above, substances represented by structural formulas (100) to (141) below and the like can be given.

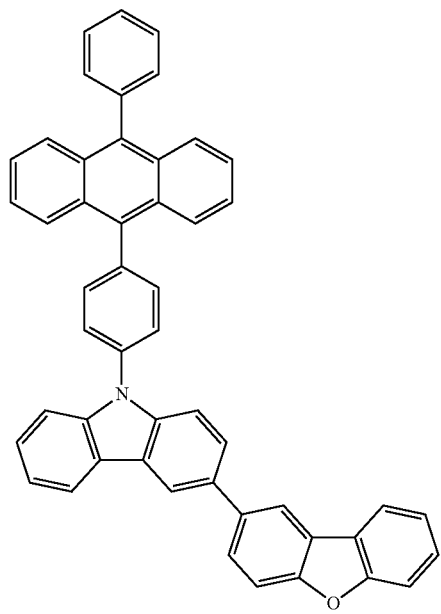

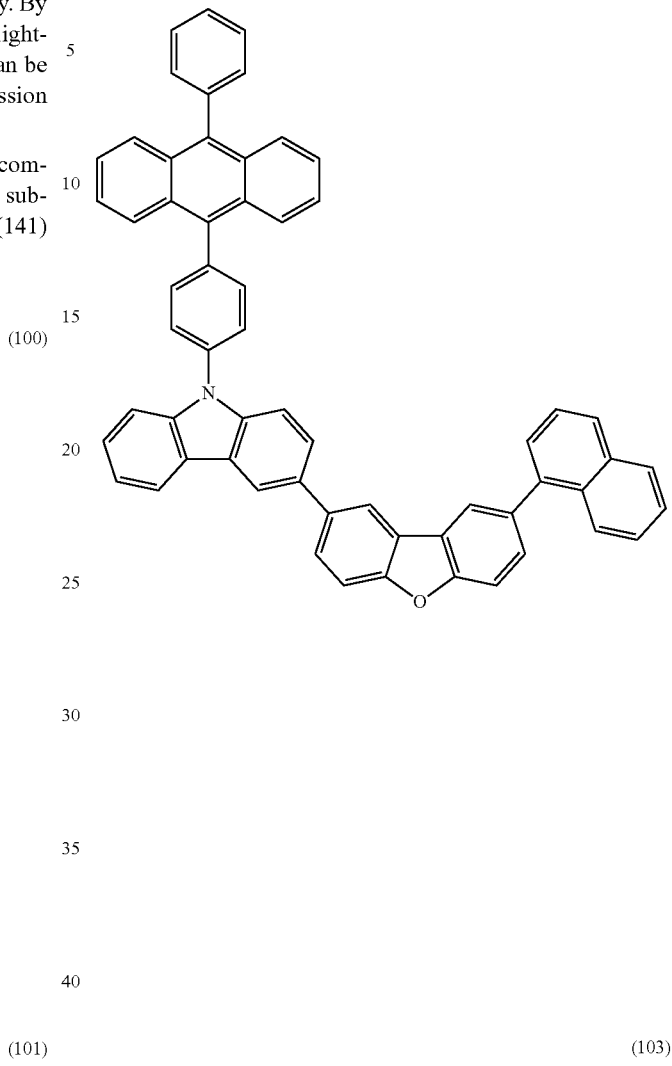

(104)
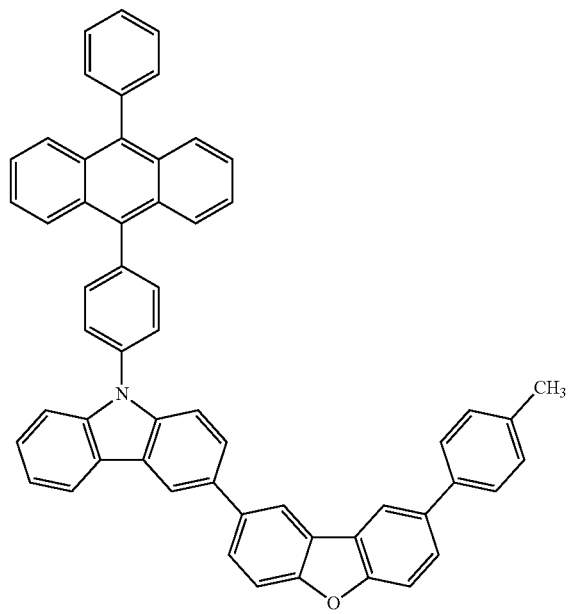
(106)
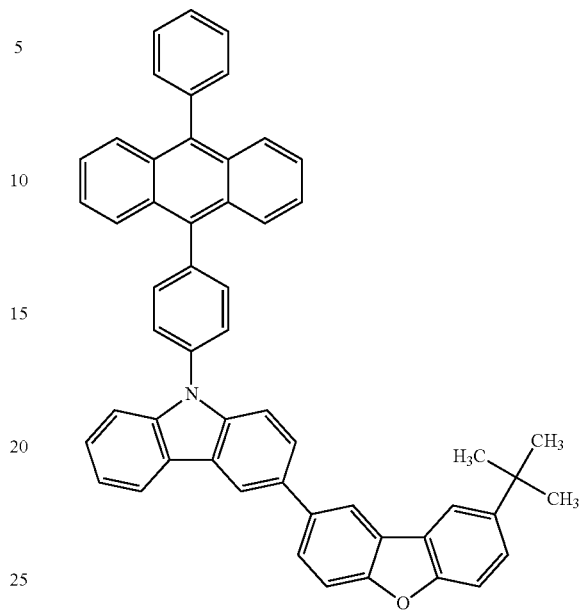
(105)
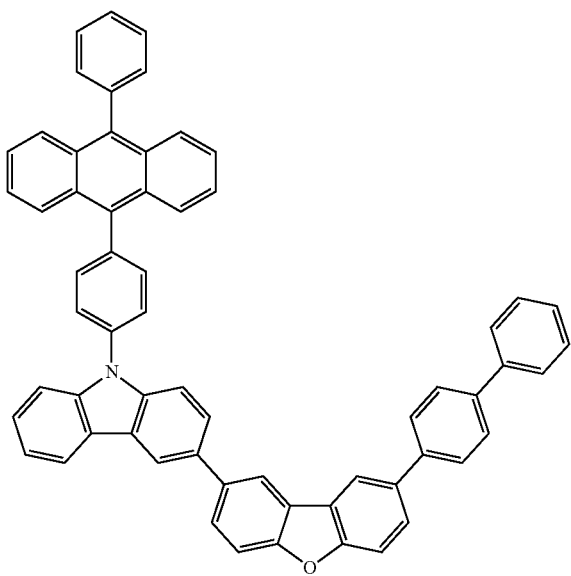
(107)
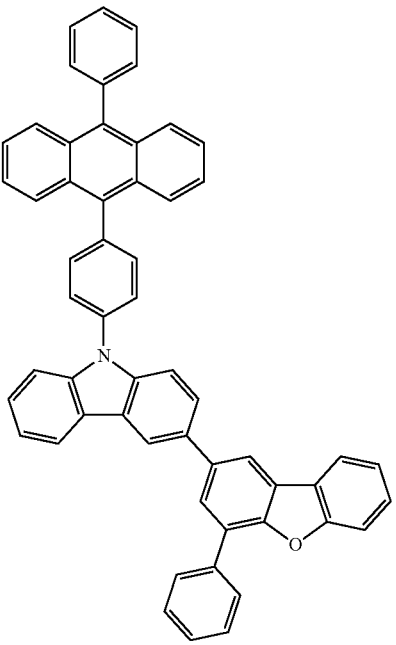

(108)
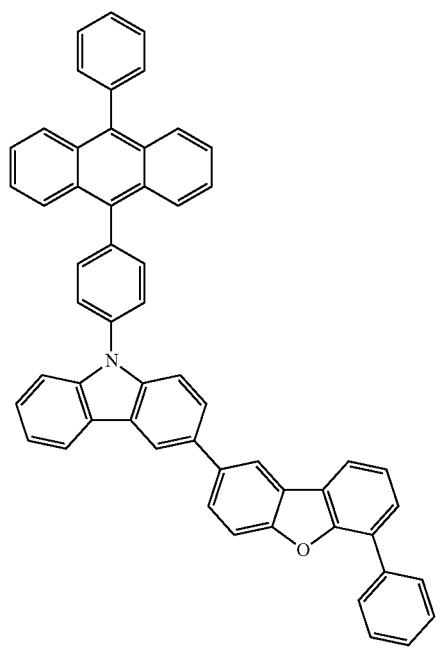
(110)
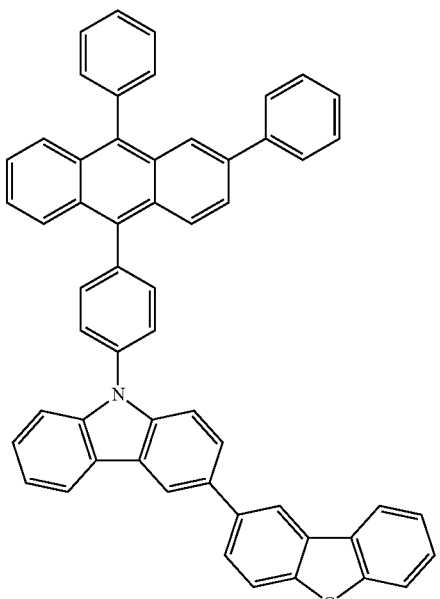
(109)
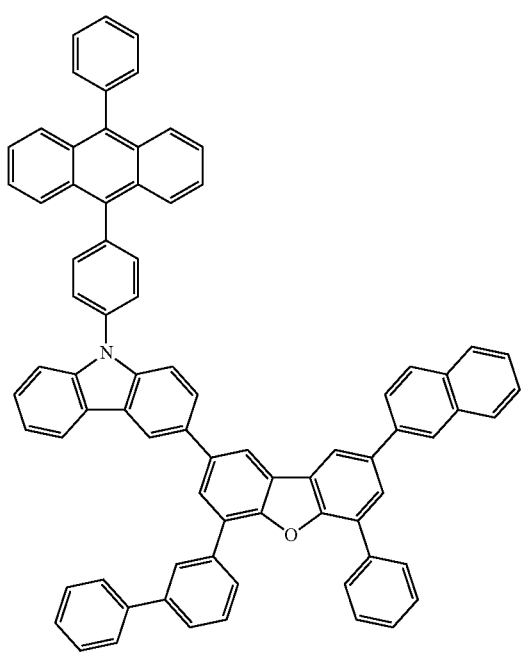
(111)
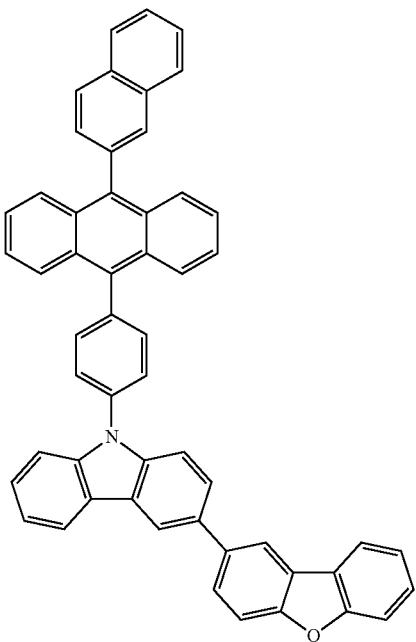

-continued
(112)
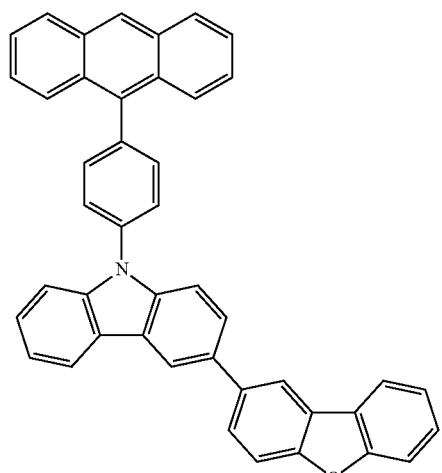
(113)
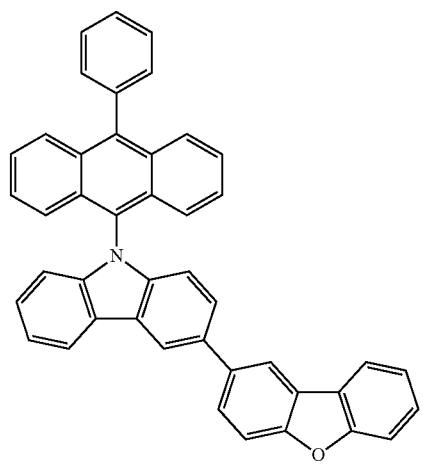
(114)
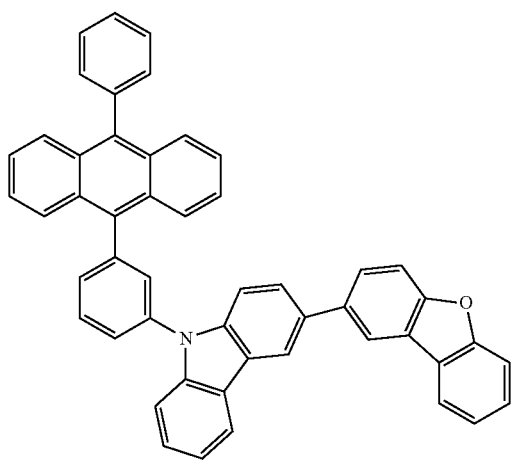
-continued
(115)
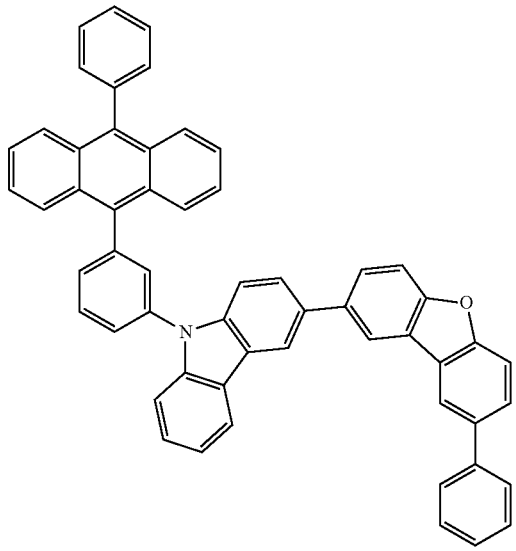
(116)
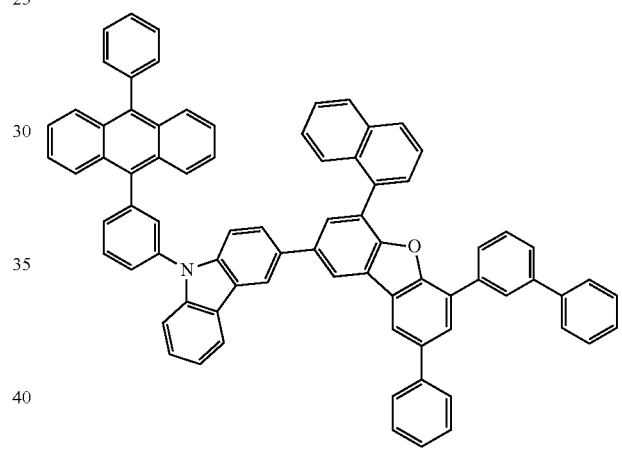
(117)
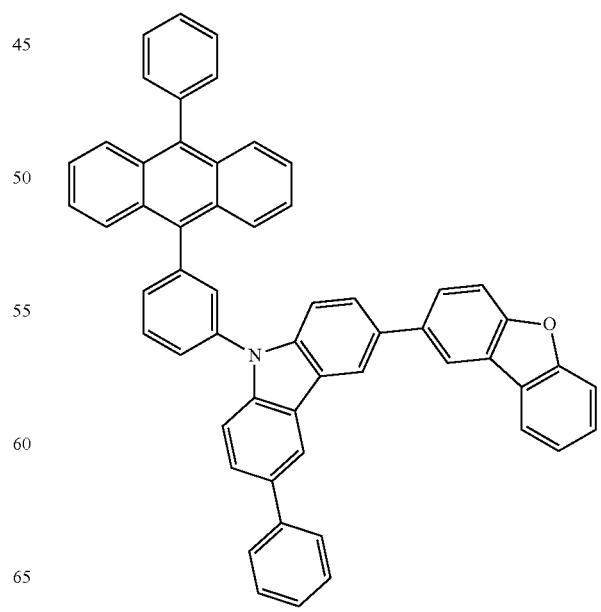

(118)
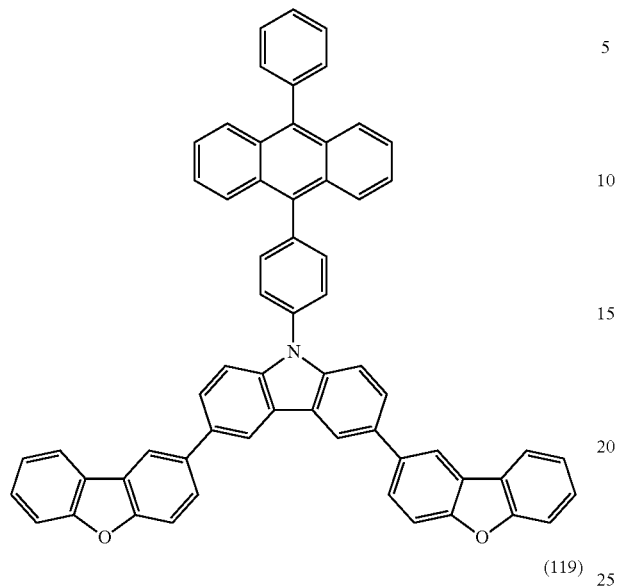
(119)
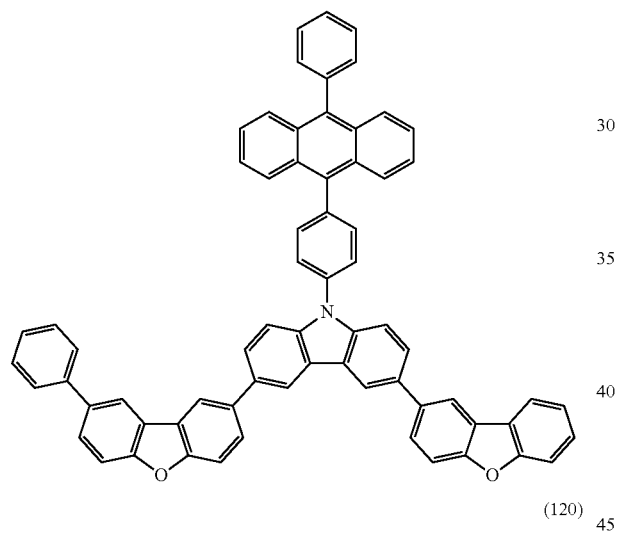
(120)
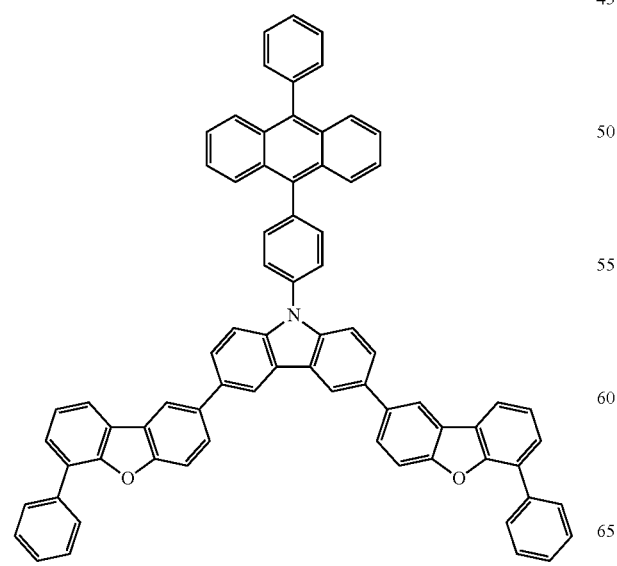
(121)
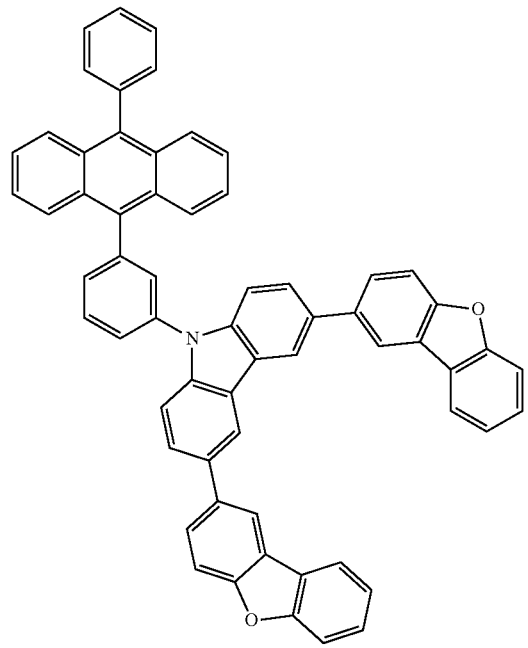
(122)
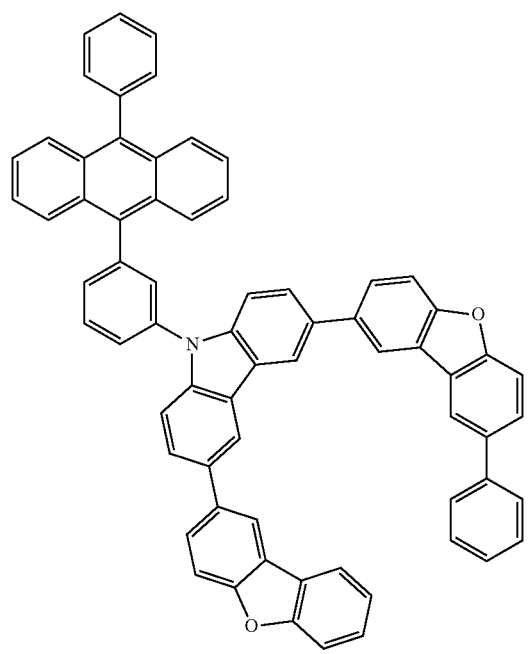

(123)
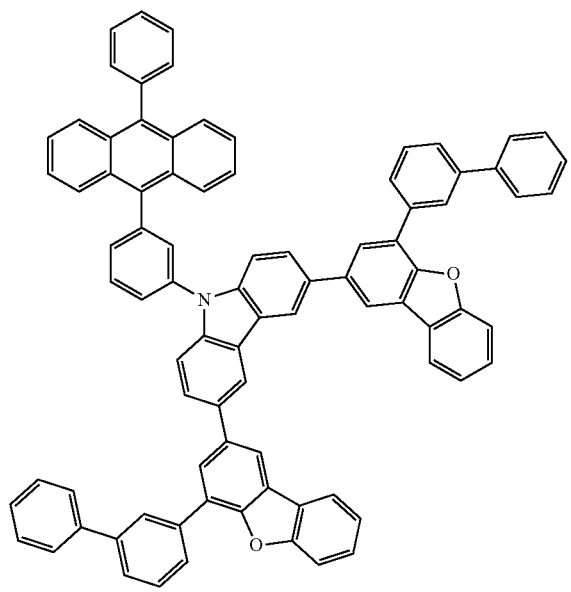
(124)
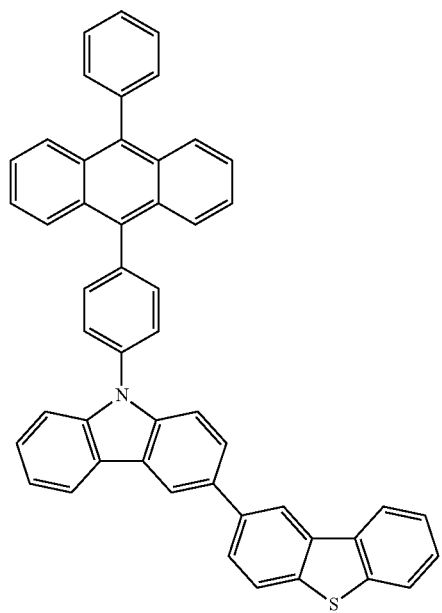
(125)
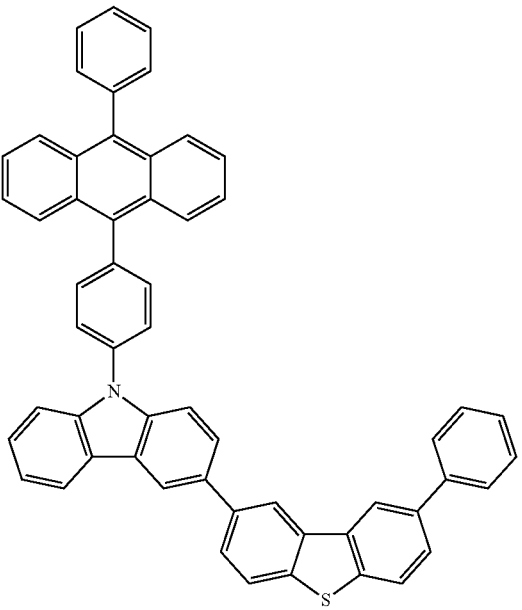
(126)
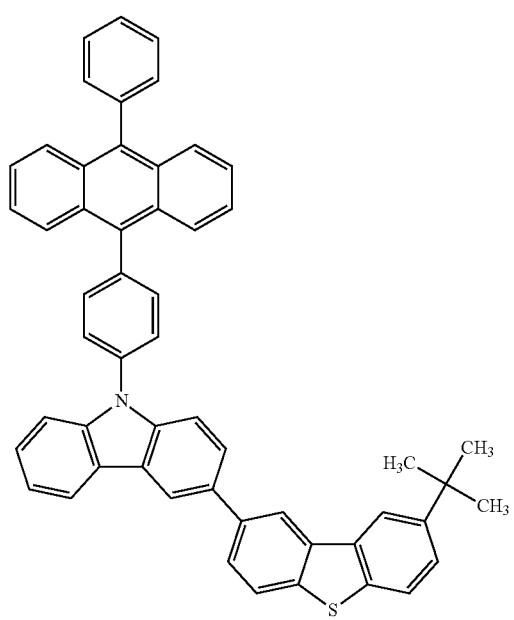

(127)
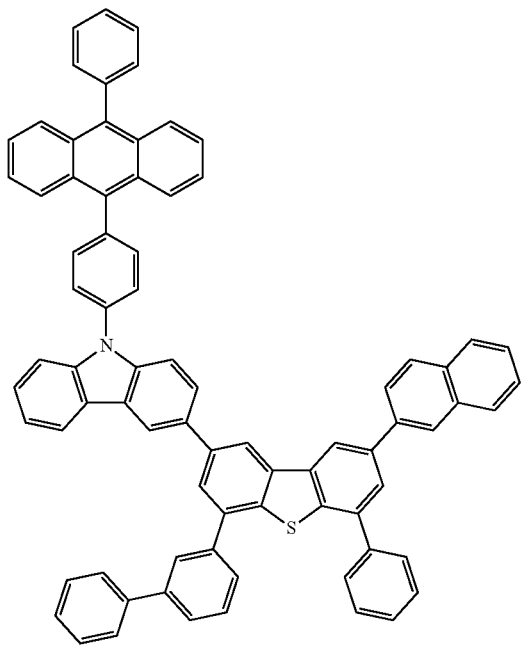
(128)
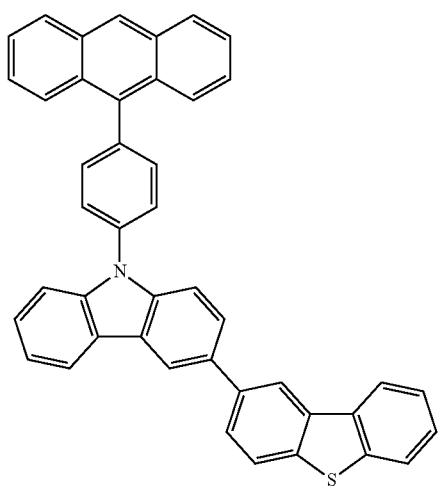
(129)
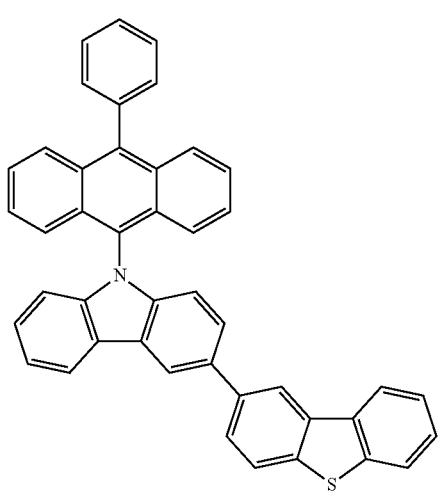
(130)
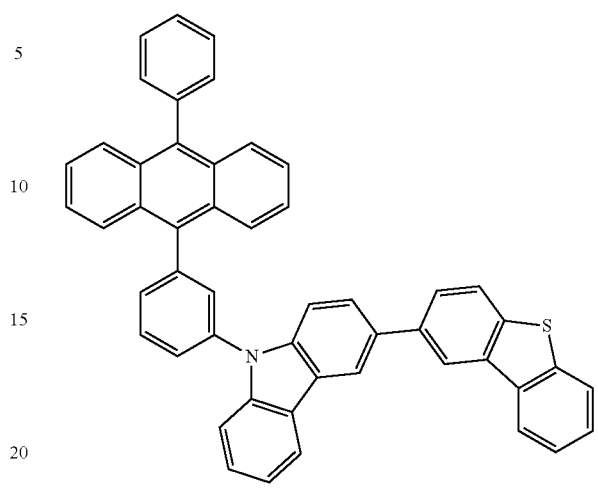
(131)
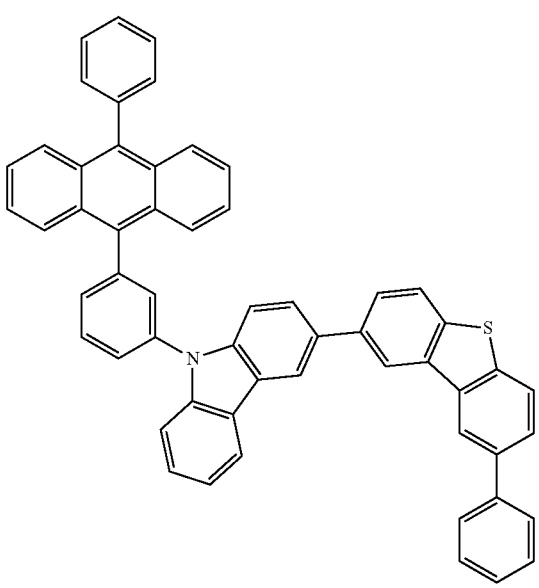

-continued
(132)
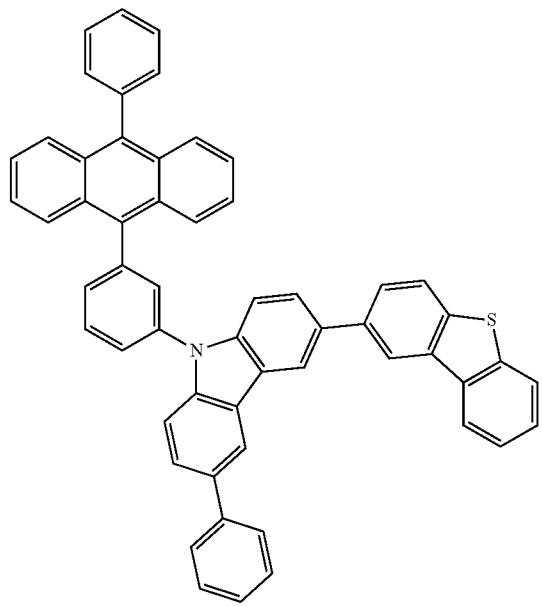
(133)
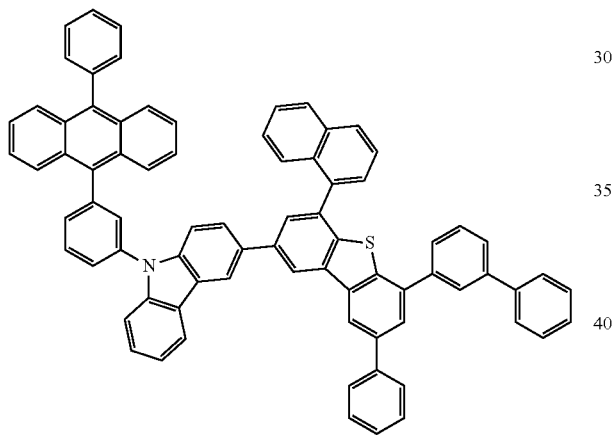
(134)
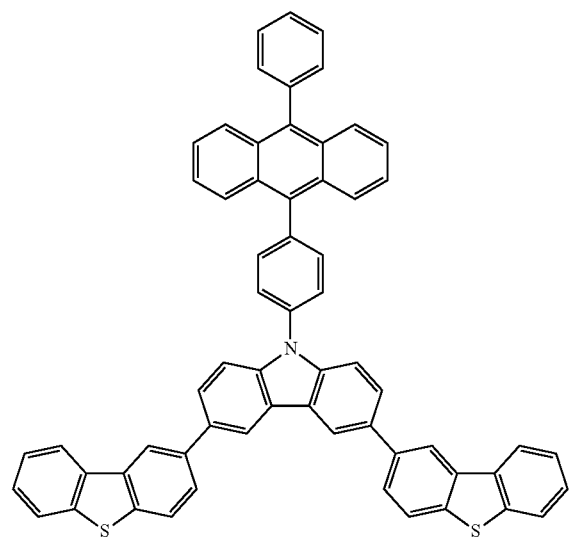
-continued
(135)
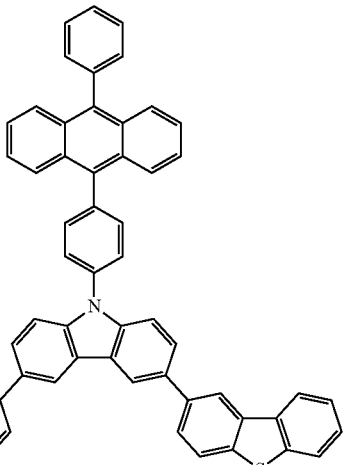
(136)
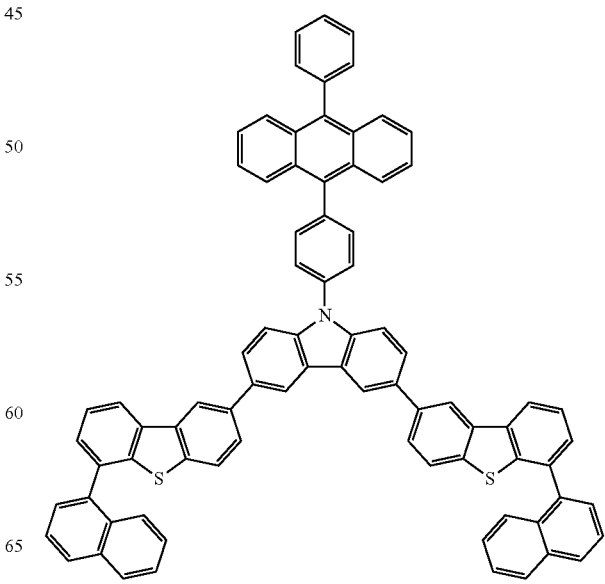

(137)
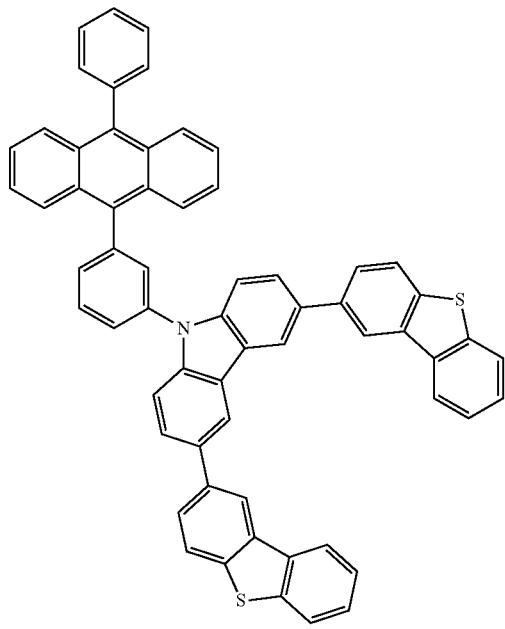
(138)
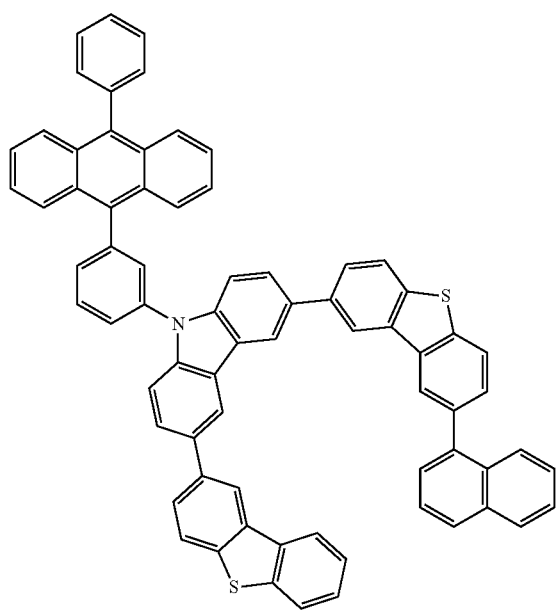
(139)
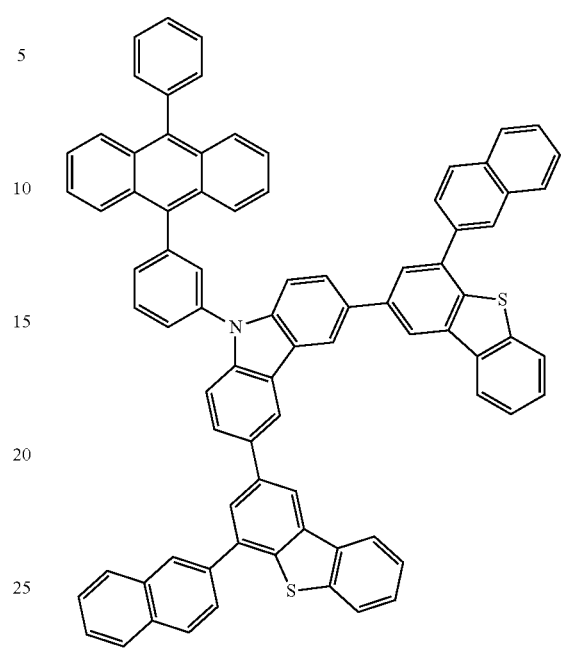
(140)
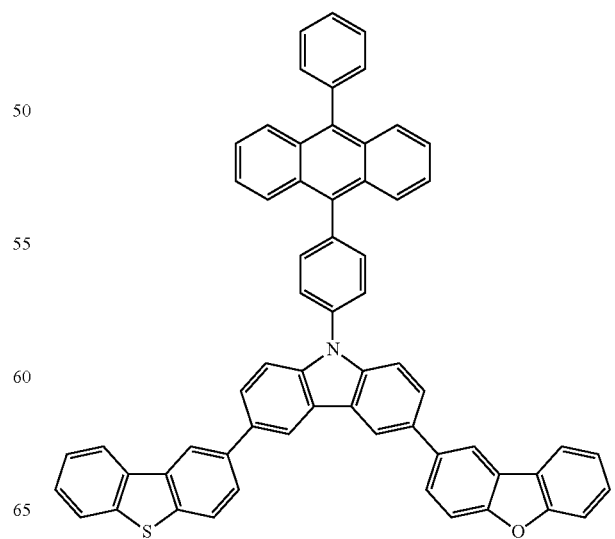

(141)

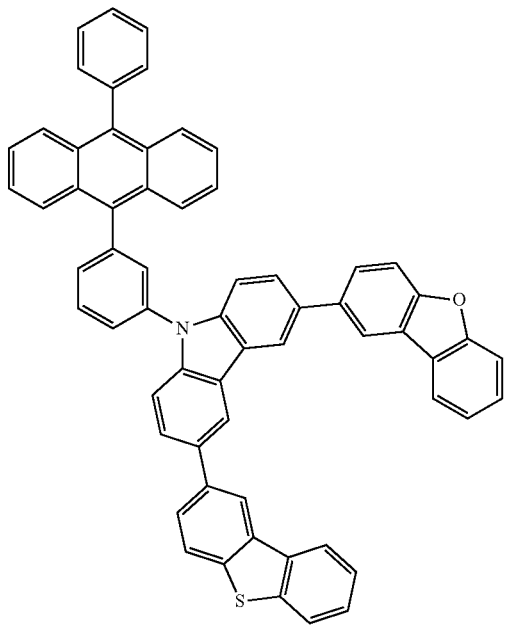

The above-described carbazole compound is suitable as a carrier-transport material or a host material because the carrier-transport property is high. Owing to this, a light-emitting element driven with a low driving voltage can also be provided. The carbazole compound in this embodiment has a rigid group such as dibenzothiophene or dibenzofuran, and thus the morphology is excellent and the film quality is stable. Further, the thermophysical property is also excellent. From the above, a light-emitting element using such a carbazole compound can be a light-emitting element having a long lifetime. In addition, since the carbazole compound includes an anthracene skeleton, which is a chromophore, the carbazole compound can be used as a light-emitting material.

Embodiment 2

Next, in this embodiment, a method of synthesizing the carbazole compound represented by a general formula (G1) is described. A variety of reactions can be applied to a method of synthesizing the carbazole compound. For example, synthesis reactions described below enable the synthesis of the carbazole compound represented by the general formula (G1).

[Method 1 of Synthesizing Carbazole Compound Represented by General Formula (G1)]

The carbazole compound (G1) described in Embodiment 1 can be synthesized in accordance with a synthesis scheme (A-1) below. That is, a halide of an anthracene derivative (a compound A) is coupled with a carbazole derivative (a compound B) by using a metal catalyst, a metal, or a metal compound in the presence of a base, so that the carbazole compound (G1) described in this embodiment is obtained.

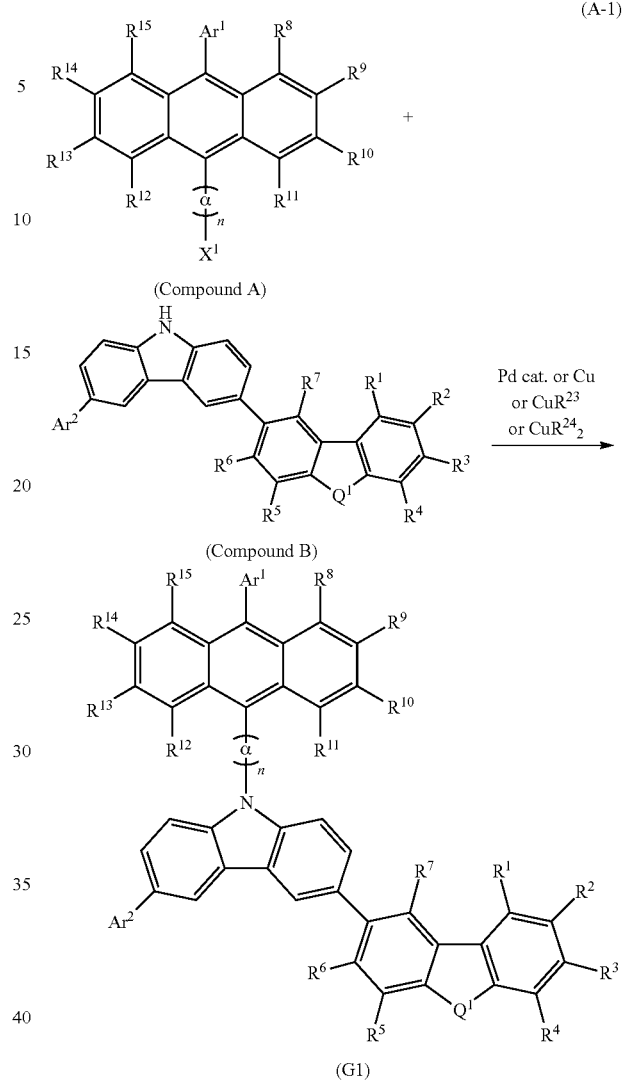

In the synthesis scheme (A-1), $Q^1$ represents oxygen or sulfur. In addition, $R^1$ to $R^{15}$ individually represent any of hydrogen, an alkyl group having 1 to 6 carbon atoms, and an aryl group having 6 to 13 carbon atoms. Note that n is 0 or 1. Further, $Ar^1$ represents hydrogen or an aryl group having 6 to 13 carbon atoms, $Ar^2$ represents any of hydrogen, an alkyl group having 1 to 6 carbon atoms, an aryl group having 6 to 13 carbon atoms, and a group represented by a general formula (g1) below. In the formula, $R^{16}$ to $R^{22}$ individually represent any of hydrogen, an alkyl group having 1 to 6 carbon atoms, and an aryl group having 6 to 13 carbon atoms. $Q^2$ represents oxygen or sulfur.

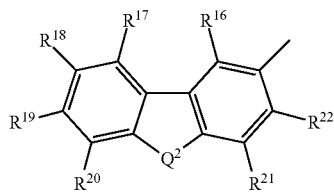

In the case where a Hartwig-Buchwald reaction is performed in the synthesis scheme (A-1), $X^1$ represents a halogen or a triflate group. As the halogen, iodine or bromine is preferable. In this reaction, a palladium catalyst including a palladium compound or a palladium complex such as bis(dibenzylideneacetone)palladium(0) or palladium(II) acetate and a ligand that coordinates to the palladium complex or the palladium compound, such as tri(tert-butyl)phosphine, tri(n-hexyl)phosphine, or tricyclohexylphosphine, is used. Examples of the base include organic bases such as sodium tert-butoxide, inorganic bases such as a potassium carbonate, and the like. In the case where a solvent is used, toluene, xylene, benzene, tetrahydrofuran, or the like can be used.

In the case where an Ullmann reaction is performed in the synthesis scheme (A-1), $X^1$ represents a halogen. As the halogen, iodine or bromine is preferable. As a catalyst, copper or a copper compound is used. In the case where a copper compound is used as the catalyst, $R^{23}$ and $R^{24}$ in the formula (A-1) individually represent a halogen, an acetyl group, or the like. As the halogen, chlorine, bromine, or iodine can be given. Note that copper(I) iodide where $R^{23}$ is iodine or copper(II) acetate where $R^{24}$ is an acetyl group is preferably used. As the base which is used, an inorganic base such as a potassium carbonate can be given. As a solvent, 1,3-dimethyl-3,4,5,6-tetrahydro-2(1H)-pyrimidinone (DMPU), toluene, xylene, benzene, and the like can be employed. However, the solvent is not limited thereto. In the Ullmann reaction, the objective substance can be obtained in a shorter time and in a higher yield when the reaction temperature is 100° C. or higher; therefore, it is preferable to use DMPU or xylene that has a high boiling point. In addition, since the reaction temperature is more preferably 150° C. or higher, DMPU is more preferably used.

[Method 2 of Synthesizing Carbazole Compound Represented by General Formula (G1)]

In the case where n is 1, the carbazole compound (G1) described in Embodiment 1 can be synthesized also in accordance with a synthesis scheme (A-2) below. That is, a halide of an anthracene derivative (a compound C) is coupled with an organoboron compound of a carbazole derivative (a compound D) according to a Suzuki-Miyaura reaction using a palladium catalyst, so that the carbazole compound represented by the general formula (G1) can be obtained.

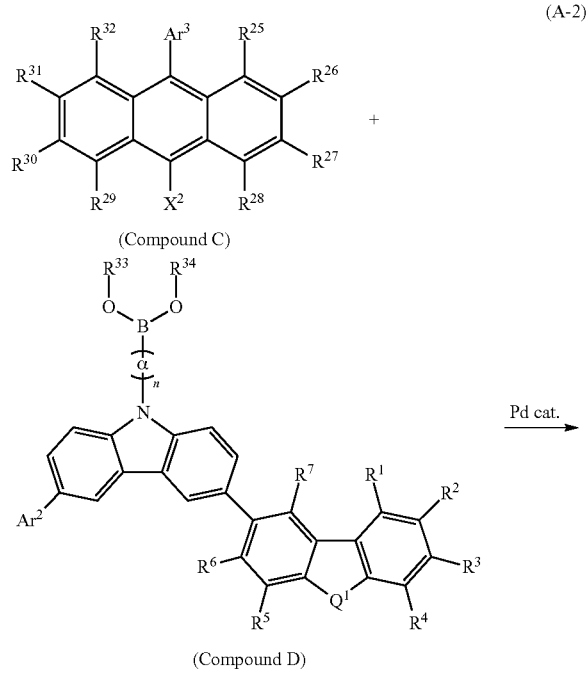

(A-2)

(Compound C)

(Compound D)

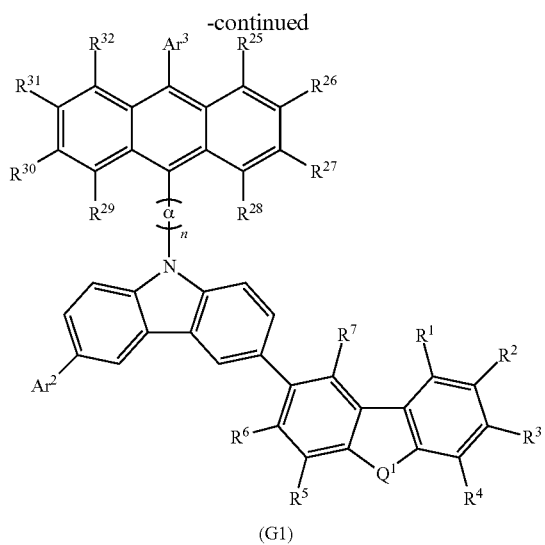

(G1)

In the synthesis scheme (A-2), $X^2$ represents a halogen. As the halogen, iodine or bromine is preferable. In the synthesis scheme (A-2), $R^{33}$ and $R^{34}$ individually represent hydrogen or an alkyl group having 1 to 6 carbon atoms, may be the same or different from each other, and may be combined with each other to form a ring.

In addition, $Q^1$ represents oxygen or sulfur, and $R^1$ to $R^6$ and $R^{25}$ to $R^{32}$ individually represent any of hydrogen, an alkyl group having 1 to 6 carbon atoms, and an aryl group having 6 to 13 carbon atoms. Note that n is 1. Further, $Ar^3$ represents hydrogen or an aryl group having 6 to 13 carbon atoms, $Ar^2$ represents any of hydrogen, an alkyl group having 1 to 6 carbon atoms, an aryl group having 6 to 13 carbon atoms, and a group represented by the general formula (g1) below. In the formula, $R^{16}$ to $R^{22}$ individually represent any of hydrogen, an alkyl group having 1 to 6 carbon atoms, and an aryl group having 6 to 13 carbon atoms. $Q^2$ represents oxygen or sulfur.

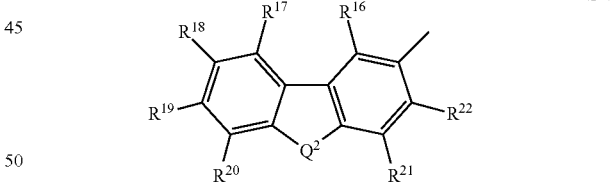

(g1)

In the reaction in the synthesis scheme (A-2), a palladium catalyst including a palladium compound or a palladium complex such as palladium(II) acetate or tetrakis(triphenylphosphine)palladium(0) and a ligand that coordinates to the palladium complex or the palladium compound, such as tri(ortho-tolyl)phosphine or tricyclohexylphosphine, is used. Examples of the base include organic bases such as sodium tert-butoxide, inorganic bases such as a potassium carbonate, and the like. Examples of solvents are as follows: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as 1,2-dimethoxyethane, and water; and the like. Use of a mixed solvent of toluene and water or a mixed solvent of toluene, ethanol, and water is more preferable.

The halide of an anthracene derivative (the compound C) is reacted with the organoboron compound of a carbazole compound (the compound D) in the scheme (A-2) above; however, even when compounds where reactive groups of the compound C and the compound D are interchanged (the halogen group and the boron compound are interchanged) are reacted with each other, the same substance can be synthesized.

In the above manner, the carbazole compound described in Embodiment 1 can be synthesized.

Embodiment 3

This embodiment shows an example in which any of the carbazole compounds described in Embodiment 1 is used for an active layer of a vertical transistor (SIT), which is a kind of an organic semiconductor element.

Figure 2:
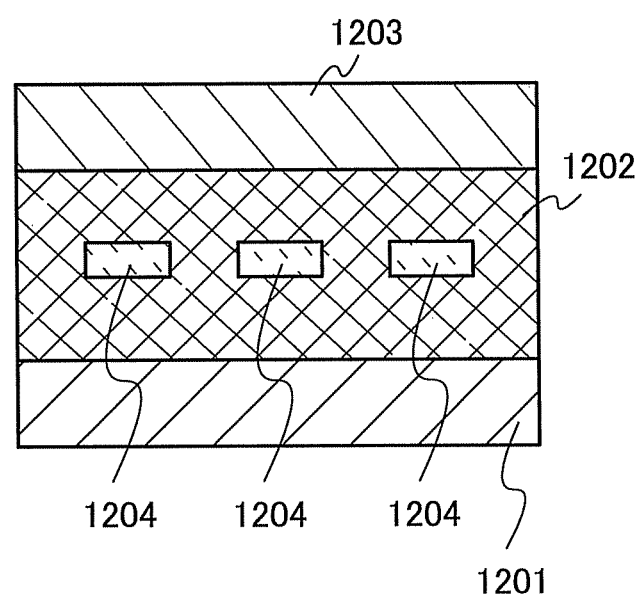
FIG. 2 is a conceptual diagram of an organic semiconductor element.

The element has a structure in which a thin-film active layer 1202 containing the carbazole compound described in Embodiment 1 is interposed between a source electrode 1201 and a drain electrode 1203, and a gate electrode 1204 is embedded in the active layer 1202, as illustrated in FIG. 2. The gate electrode 1204 is electrically connected to a unit to apply a gate voltage, and the source electrode 1201 and the drain electrode 1203 are electrically connected to a unit to control the voltage between the source and the drain.

In such an element structure, when a voltage is applied between the source and the drain under the condition where a gate voltage is not applied, a current flows (an ON state). Then, when a gate voltage is applied in this state, a depletion layer is generated in the periphery of the gate electrode 1204, and thus a current does not flow (an OFF state). With such a mechanism, the element operates as a transistor.

In a vertical transistor, a material which has both a carrier-transport property and favorable film quality is required for an active layer like in a light-emitting element. Any of the carbazole compounds described in Embodiment 1 can be suitably used because it sufficiently meets these requirements.

Embodiment 4

In this embodiment, one embodiment of a light-emitting element using any of the carbazole compounds described in Embodiment 1 is described with reference to FIG. 1A.

A light-emitting element of this embodiment has a plurality of layers between a pair of electrodes. In this embodiment, the light-emitting element includes a first electrode 102, a second electrode 104, and a layer 103 containing an organic compound provided between the first electrode 102 and the second electrode 104. In addition, in this embodiment, the first electrode 102 serves as an anode and the second electrode 104 serves as a cathode. In other words, when a voltage is applied between the first electrode 102 and the second electrode 104 such that the potential of the first electrode 102 is higher than that of the second electrode 104, light emission can be obtained.

The substrate 101 is used as a support of the light-emitting element. As the substrate 101, glass, plastic, or the like can be used, for example. Note that materials other than glass or plastic can be used as long as they can function as a support of a light-emitting element.

The first electrode 102 is preferably formed using a metal, an alloy, a conductive compound, a mixture of them, or the like each having a high work function (specifically, a work function of 4.0 eV or higher). Specifically, for example, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like can be given. Films of these conductive metal oxides are usually formed by sputtering; however, a sol-gel method or the like may also be used. For example, indium oxide-zinc oxide (IZO) can be formed by a sputtering method using indium oxide into which zinc oxide of 1 to 20 wt % is added, as a target. Moreover, indium oxide containing tungsten oxide and zinc oxide (IWZO) can be formed by a sputtering method using a target in which 0.5 to 5 wt % of tungsten oxide and 0.1 to 1 wt % of zinc oxide with respect to indium oxide are contained. Besides, gold (Au), platinum (Pt), nickel (Ni), tungsten (W), chromium (Cr), molybdenum (Mo), iron (Fe), cobalt (Co), copper (Cu), palladium (Pd), graphene, nitride of a metal material (e.g., titanium nitride), and the like can be given.

There is no particular limitation on a stacked structure of the layer 103 containing an organic compound. The layer 103 containing an organic compound may be formed as appropriate by combining a layer that contains a substance having a high electron-transport property, a layer that contains a substance having a high, hole-transport property, a layer that contains a substance having a high electron-injection property, a layer that contains a substance having a high hole-injection property, a layer that contains a bipolar substance (a substance having a high electron- and hole-transport property), and the like. For example, the layer 103 containing an organic compound can be formed in an appropriate combination of a hole-injection layer, a hole-transport layer, a light-emitting layer, an electron-transport layer, an electron-injection layer, and the like. In this embodiment, described is a structure in which the layer 103 containing an organic compound includes a hole-injection layer 111, a hole-transport layer 112, a light-emitting layer 113, and an electron-transport layer 114 stacked in that order over the first electrode 102. Specific materials to form each of the layers are given below.

The hole-injection layer 111 is a layer that contains a substance having a high hole-injection property. As the substance having a high hole-injection property, the following can be used: molybdenum oxide, vanadium oxide, ruthenium oxide, tungsten oxide, manganese oxide, or the like. Alternatively, the hole-injection layer 111 can be formed using a phthalocyanine-based compound such as phthalocyanine (abbreviation: $H_2Pc$) or copper phthalocyanine (abbreviation: CuPc); an aromatic amine compound such as 4,4'-bis [N-(4-diphenylaminophenyl)-N-phenylamino]bipheriyl (abbreviation: DPAB) or N,N'-bis[4-[bis(3-methylphenyl)amino]phenyl]-N,N'-diphenyl-[1,1'-biphenyl]-4,4'-diamine (abbreviation: DNTPD); a high molecular compound such as poly(ethylenedioxythiophene)/poly(styrenesulfonic acid) (PEDOT/PSS), or the like.

Alternatively, the hole-injection layer 111 can be formed using a composite material in which a substance having an acceptor property is mixed into a substance having a high hole-transport property. Note that, by using such a substance having an acceptor property into which a substance having a high hole-transport property is mixed, a material used to form an electrode may be selected regardless of its work function. In other words, besides a material having a high work function, a material having a low work function can also be used for the first electrode 102. As the acceptor substance, 7,7,8, 8-tetracyano-2,3,5,6-tetrafluoroquinodimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air and its hygroscopic property is low and is easily treated.

As the substance having high hole-transport properties used for the composite material, any of various organic compounds such as an aromatic amine compound, a carbazole compound, aromatic hydrocarbon, and a high molecular compound (such as an oligomer, a dendrimer, or a polymer) can be used. The organic compound used for the composite material is preferably an organic compound having a high hole-transport property. Specifically, a substance having a hole mobility of $1 \times 10^{-6}$ cm$^2$/V·s or higher is preferably used. However, other substances may be used if the substances have a hole-transport property higher than an electron-transport property. An organic compound which can be used as a substance having a high hole-transport property for the composite material is specifically given below.

As aromatic amine compounds, for example, there are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis[4-[bis(3-methylphenyl)amino]phenyl]-N,N'-diphenyl-[1,1'-biphenyl]-4,4'-diamine (abbreviation: DNTPD), 1,3,5-tris[N-(4-diphenylaminophenyl)-N-phenylamino]benzene (abbreviation: DPA3B), and the like.

As carbazole compounds that can be used for the composite material, specifically, there are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

In addition, as the carbazole compounds that can be used for the composite material, there are also 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbon which can be used for the composite material include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. As described above, aromatic hydrocarbon which has a hole mobility of $1 \times 10^{-6}$ cm$^2$/V·s or higher and which has 14 to 42 carbon atoms is more preferable.

The aromatic hydrocarbon which can be used for the composite material may have a vinyl skeleton. As the aromatic hydrocarbon having a vinyl group, the following are given for example: 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Moreover, a high molecular compound such as poly(N-vinylcarbazole) (abbreviation: PVK), poly(-vinyltiphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine (abbreviation: poly-TPD) can also be used.

Any of the carbazole compounds described in Embodiment 1 can also be used as aromatic hydrocarbon that can be used for a composite material.

The hole-transport layer 112 is a layer that contains a substance having a high hole-transport property. As a substance having a high hole-transport property, those given above as the substances having a high hole-transport property, which can be used for the composite material, can be similarly used. Note that a detailed description is omitted to avoid repetition. The description of the composite material is to be referred to.

The light-emitting layer 113 is a layer that contains a light-emitting substance. The light-emitting layer 113 may be formed with a film of a light-emitting substance alone or a film in which an emission center substance is dispersed in a host material; in this embodiment, a light-emitting layer of a host-guest type in which the carbazole compound represented by the general formula (G1) described in Embodiment 1 is used as a host material is described.

In the light-emitting layer 113, as a material that can be used as the emission center substance, any of a variety of substances that emit fluorescence with a wavelength longer than that of blue can be applied to. Examples of the emission center substance include the N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N,N-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo quinolizin-9-yl)ethenyl]-4H-pyran-4-ylidenel}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like can be given.

Alternatively, any of the carbazole compounds represented by the general formula (G1) described in Embodiment 1 can be used as the emission center substance because it is a fluorescent material with a high quantum yield.

Any of the carbazole compounds represented by the general formula (G1) described in Embodiment 1 has a wide band gap and thus can be suitably used as a host material in which an emission center substance that emits blue fluorescence is dispersed. Needless to say, the carbazole compound can be used as a host material in which an emission center substance that emits fluorescence with a wavelength longer than that of blue is dispersed. Since the carbazole compound has a wide band gap, energy of carriers that are recombined in the host material can be effectively transported to the emission center substance; therefore, a light-emitting element with high emission efficiency can be fabricated.

In the case where the carbazole compound represented by the general formula (G1) is not used as the above-described host material, examples of the host material include metal complexes, heterocyclic compounds, and aromatic amine compounds. As metal complexes, the following can be given: tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), bis[2-(2-benzothiazolyl)phenolato]zinc(II) (abbreviation: ZnBTZ), and the like. As heterocyclic compounds, the following can be given: 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), bathocuproine (abbreviation: BCP), 9-[4-(5-phenyl-1,3,4-oxadiazol-2-yl)phenyl]-9H-carbazole (abbreviation: CO11), and the like. As aromatic amine compounds, the following can be given: 4,4'-bis[N-(1-naphthyl)-N-phenylamino]biphenyl (abbreviation: NPB or α-NPD), N,N'-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]-1,1'-biphenyl (abbreviation: BSPB), and the like. In addition, condensed polycyclic aromatic compounds such as anthracene derivatives, phenanthrene derivatives, pyrene derivatives, chrysene derivatives, and dibenzo[g,p]chrysene derivatives are given. Specific examples of the condensed polycyclic aromatic compound include 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N",N",N''',N'''-octaphenyldibenzo[g,p]chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), and the like. One or more substances having a wider energy gap than the above-described emission center substance may be selected from these substances and known substances.

The light-emitting layer 113 may be a stack of two or more layers. For example, in the case where the light-emitting layer 113 is formed by stacking a first light-emitting layer and a second light-emitting layer in that order from the hole-transport layer side, the first light-emitting layer is formed using a substance having a hole-transport property as the host material and the second light-emitting layer is formed using a substance having an electron-transport property as the host material.

In the case where the light-emitting layer having the above-described structure is formed using a plurality of materials, the light-emitting layer can be formed using co-evaporation by a vacuum evaporation method; or an inkjet method, a spin coating method, a dip coating method, or the like using a solution of the materials.

The electron-transport layer 114 is a layer that contains a substance having a high electron-transport property. For example, a layer containing a metal complex having a quinoline skeleton or a benzoquinoline skeleton, such as tris(8-quinolinolato)aluminum (abbreviation: Alq), tris(4-methyl-8-quinolinolato)aluminum (abbreviation: Alq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq), or the like can be used. Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here are mainly ones that have an electron mobility of $1 \times 10^{-6}$ cm$^2$/V·s or higher. The electron-transport layer may be formed using other substances than those described above as long as the substances have an electron-transport property higher than a hole-transport property.

Any of the carbazole compounds represented by the general formula (G1) described in Embodiment 1 can be applied to the electron-transport layer 114. Further, the carbazole compound having a wide band gap can be suitably used as a material used for a carrier-transport layer that is adjacent to a light-emitting layer containing an emission center substance that emits blue fluorescence without deactivating excitation energy of the emission center substance. Therefore, a light-emitting element with high emission efficiency can be fabricated. Needless to say, the carbazole compound can also be used as a material used for a carrier-transport layer that is adjacent to a light-emitting layer containing an emission center substance that emits fluorescence with a wavelength longer than that of blue.

Furthermore, the electron-transport layer is not limited to a single layer, and two or more layers formed using the aforementioned substances may be stacked.

Further, a layer for controlling transport of electron carriers may be provided between the electron-transport layer and the light-emitting layer. Specifically, the layer for controlling transport of electron carriers is a layer formed by adding a small amount of substance having a high electron-trapping property to the material having a high electron-transport property as described above, so that carrier balance can be adjusted. Such a structure is very effective in suppressing a problem (such as shortening of element lifetime) caused when electrons pass through the light-emitting layer.

In addition, an electron-injection layer may be provided between the electron-transport layer and the second electrode 104, in contact with the second electrode 104. As the electron-injection layer, an alkali metal, an alkaline earth metal, or a compound thereof such as lithium fluoride (LiF), cesium fluoride (CsF), or calcium fluoride ($CaF_2$) can be used. For example, a layer of a material having an electron-transport property containing an alkali metal, an alkaline earth metal, or a compound thereof, such as an Alq layer containing magnesium (Mg), can be used. By using a layer of a substance having an electron-transport property containing an alkali metal or an alkaline earth metal as the electron-injection layer, electron injection from the second electrode 104 is performed efficiently, which is preferable.

The second electrode 104 can be funned using a metal, an alloy, an electrically conductive compound, or a mixture of them, having a low work function (specifically, a work function of 3.8 eV or lower). As a specific example of such a cathode material, an element belonging to Group 1 or 2 in the periodic table, i.e., an alkali metal such as lithium (Li) or cesium (Cs), or an alkaline earth metal such as magnesium (Mg), calcium (Ca), or strontium (Sr); an alloy containing any of them (such as MgAg or AlLi); a rare earth metal such as europium (Eu) or ytterbium (Yb); an alloy containing such a rare earth metal; or the like can be used. However, when the electron-injection layer is provided between the second electrode 104 and the electron-transport layer, the second electrode 104 can be formed using any of a variety of conductive materials such as Al, Ag, ITO, or indium oxide-tin oxide containing silicon or silicon oxide regardless of its work function. These conductive materials can be deposited by a sputtering method, an inkjet method, a spin-coating method, or the like.

Further, any of a variety of methods can be employed for forming the layer 103 containing an organic compound regardless of a dry process or a wet process. For example, a vacuum evaporation method, an inkjet method, a spin coating method or the like may be used. A different formation method may be employed for each electrode or each layer.

The electrode may be formed by a wet method using a sol-gel method, or by a wet method using a paste of a metal material. Alternatively, the electrode may be formed by a dry method such as a sputtering method or a vacuum evaporation method.

In the light-emitting element having the above-described structure, a current flows due to a potential difference made between the first electrode 102 and the second electrode 104, a hole and an electron are recombined in the light-emitting layer 113, which contains a substance having a high light-emitting property, and light is emitted. That is, a light-emitting region is formed in the light-emitting layer 113.

The emitted light is extracted out through one or both of the first electrode 102 and the second electrode 104. Therefore, one or both of the first electrode 102 and the second electrode 104 is/are light-transmissive electrode(s). When only the first electrode 102 has a light-transmitting property, light emission is extracted from the substrate side through the first electrode 102. Meanwhile, when only the second electrode 104 has a light-transmitting property, light emission is extracted from the side opposite to the substrate side through the second electrode 104. In a case where each of the first electrode 102 and the second electrode 104 has a light-transmitting property, light emission is extracted from both of the substrate side and the side opposite to the substrate side through the first electrode 102 and the second electrode 104.

The structure of the layers provided between the first electrode 102 and the second electrode 104 is not limited to the aforementioned one. However, a structure in which a light-emitting region for recombination of holes and electrons is positioned away from the first electrode 102 and the second electrode 104 so as to prevent quenching due to the proximity of the light-emitting region and a metal used for an electrode or a carrier-injection layer is preferable. The order of stacking the layers is not limited to the above, and the following order, which is opposite to that in FIG. 1A, may be employed: the second electrode, the electron-injection layer, the electron-transport layer, the light-emitting layer, the hole-transport layer, the hole-injection layer, and the first electrode from the substrate side.

In addition, as for the hole-transport layer or the electron-transport layer in direct contact with the light-emitting layer, particularly a carrier-transport layer in contact with a side closer to a light-emitting region in the light-emitting layer 113, in order to suppress energy transfer from an exciton which is generated in the light-emitting layer, it is preferable that the energy gap thereof be wider than the energy gap of the light-emitting substance contained in the light-emitting layer or the energy gap of the emission center substance contained in the light-emitting layer.

Since the light-emitting element in this embodiment is formed using any of the carbazole compounds described in Embodiment 1, which has a wide energy gap, as a host material and/or for an electron-transport layer, efficient light emission can be realized even when the emission center substance has a wide energy gap and emits blue fluorescence, and a light-emitting element with high emission efficiency can be provided. Accordingly, a light-emitting element with lower power consumption can be provided. In addition, light emission from a host material or a material used for a carrier-transport layer is unlikely to occur; thus, a light-emitting element that provides light emission with high color purity can be provided. Further, any of the carbazole compounds described in Embodiment 1 has an excellent carrier-transport property; therefore, a light-emitting element driven with a low driving voltage can be provided.

In this embodiment, the light-emitting element is formed over a substrate made of glass, plastic, or the like. By manufacturing a plurality of such light emitting elements over one substrate, a passive matrix light-emitting device can be manufactured. In addition, for example, a thin film transistor (TFT) may be formed over a substrate formed of glass, plastic, or the like, and a light-emitting element may be manufactured over an electrode electrically connected to the TFT. In this way, an active matrix light-emitting device in which the TFT controls the drive of the light-emitting element can be manufactured. Note that there is no particular limitation on the structure of the TFT. Either a staggered TFT or an inverted staggered TFT may be employed. In addition, crystallinity of a semiconductor used for the TFT is not particularly limited either; an amorphous semiconductor or a crystalline semiconductor may be used. In addition, a driver circuit formed over a TFT substrate may be constructed from both n-channel and p-channel TFTs or from one of n-channel and p-channel TFTs.

Embodiment 5

In this embodiment, an embodiment of a light-emitting element with a structure in which a plurality of light-emitting units are stacked (hereinafter this type of light-emitting element is also referred to as a stacked element) is described with reference to FIG. 1B. This light-emitting element is a light-emitting element including a plurality of light-emitting units between a first electrode and a second electrode. Each light-emitting unit can have a structure similar to that of the layer 103 containing an organic compound described in Embodiment 4. That is, a light-emitting element described in Embodiment 4 includes a single light-emitting unit; the light-emitting element in this embodiment includes a plurality of light-emitting units.

Figure 1B:
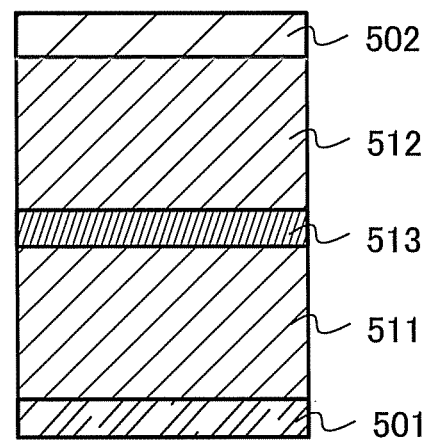

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 correspond to the first electrode 102 and the second electrode 104 in Embodiment 4, respectively, and electrodes similar to those described in Embodiment 4 can be applied to the first electrode 501 and the second electrode 502. Further, the first light-emitting unit 511 and the second light-emitting unit 512 may have the same structure or different structures.

A charge generation layer 513 contains a composite material of an organic compound and a metal oxide. The composite material of an organic compound and a metal oxide is described in Embodiment 4, and contains an organic compound and a metal oxide such as vanadium oxide, molybdenum oxide, or tungsten oxide. As the organic compound, a variety of compounds such as an aromatic amine compound, a carbazole compound, aromatic hydrocarbon, and a high molecular compound (an oligomer, a dendrimer, a polymer, or the like) can be used. As the organic compound, it is preferable to use the organic compound which has a hole-transport property and has a hole mobility of $1\times10^{-6}$ cm$^2$/V·s or higher. However, other substances may be used if the substances have a hole-transport property higher than an electron-transport property. A composite of an organic compound with metal oxide is excellent in carrier-injection property and carrier-transport property, and hence, low-voltage driving and low-current driving can be achieved.

The charge generation layer 513 may be formed by a combination of a layer containing the composite material of an organic compound and metal oxide with a layer containing another material. For example, a layer containing a composite material of the organic compound and the metal oxide may be combined with a layer containing a compound of a substance selected from substances having an electron-donating property and a compound with a high electron-transport property. Moreover, a layer containing a composite material of the organic compound and the metal oxide may be combined with a transparent conductive film.

The charge generation layer 513 interposed between the first light-emitting unit 511 and the second light-emitting unit 512 may have any structure as long as electrons can be injected to a light-emitting unit on one side and holes can be injected to a light-emitting unit on the other side when a voltage is applied between the first electrode 501 and the second electrode 502. For example, in FIG. 1B, any layer can be employed as the charge generation layer 513 as long as the layer injects electrons into the first light-emitting unit 511 and holes into the second light-emitting unit 512 when a voltage is applied such that the potential of the first electrode is higher than that of the second electrode.

Although this embodiment shows the light-emitting element having two light emitting units, the present invention can be similarly applied to a light-emitting element in which three or more light-emitting units are stacked. By arrangement of a plurality of light-emitting units, which are partitioned by the charge generation layer between a pair of electrodes, as in the light-emitting element of this embodiment, light emission in a high luminance region can be achieved with current density kept low. Thus, its current density can be kept low, so that a light-emitting element having a long lifetime can be realized. When the light-emitting element is applied for illumination, voltage drop due to resistance of an electrode material can be reduced, thereby achieving homogeneous light emission in a large area. Moreover, a light-emitting device, which can be driven at a low voltage and consumes less power, can be realized.

The light-emitting units emit light having different colors from each other, thereby obtaining light emission of a desired color in the whole light-emitting element. For example, in a light-emitting element having two light-emitting units, the emission colors of the first light-emitting unit and the second light-emitting unit are made complementary, so that the light-emitting element which emits white light as the whole light-emitting element can be obtained. Note that the word "complementary" means color relationship in which an achromatic color is obtained when colors are mixed. That is, when complementary colored light emitted from substances is mixed, white light emission can be obtained. This can be applied to a light-emitting element having three or more light-emitting units. For example, when the first light-emitting unit emits red light, the second light-emitting unit emits green light, and the third light-emitting unit emits blue light, white light can be emitted from the whole light-emitting element.

Since the light-emitting element of this embodiment contains any of the carbazole compounds described in Embodiment 1, a light-emitting element with high emission efficiency can be provided. In addition, a light-emitting element driven with a low driving voltage can be provided. Further, a light-emitting element having a long lifetime can be provided. In addition, the light-emitting unit containing the carbazole compound can provide light that originates from the emission center substance with high color purity; therefore, it is easy to adjust the color of light emitted from the light-emitting element as a whole.

Note that this embodiment can be freely combined with another embodiment.

Embodiment 6

In this embodiment, a light-emitting device including a light-emitting element containing any of the carbazole compounds described in Embodiment 1 is described.

In this embodiment, the light-emitting device including a light-emitting element containing any of the carbazole compounds described in Embodiment 1 is described with reference to FIGS. 3A and 3B. Note that FIG. 3A is a top view illustrating the light-emitting device and FIG. 3B is a cross-sectional view of FIG. 3A taken along lines A-A' and B-B'. The light-emitting device includes a driver circuit portion (source-side driver circuit) 601, a pixel portion 602, and a driver circuit portion (gate-side driver circuit) 603 which are illustrated with dotted lines. These units control light emission of the light-emitting element. Moreover, a reference numeral 604 denotes a sealing substrate; 605, a sealing material; and 607, a space surrounded by the sealing material 605.

Reference numeral 608 denotes a wiring for transmitting signals to be inputted into the source-side driver circuit 601 and the gate-side driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, the cross-sectional structure is described with reference to FIG. 3B. The driver circuit portion and the pixel portion are formed over an element substrate 610. In this embodiment, the source-side driver circuit 601, which is the driver circuit portion, and one pixel of the pixel portion 602 are shown.

In the source-side driver circuit 601, a CMOS circuit is formed in which an n-channel TFT 623 and a p-channel TFT 624 are combined. Such a driver circuit may be formed by using various circuits such as a CMOS circuit, a PMOS circuit, or an NMOS circuit. Although this embodiment illustrates a driver-integrated type where the driver circuit is formed over the substrate, the present invention is not limited to this, and the driver circuit may be formed outside the substrate, not over the substrate.

The pixel portion 602 is formed with a plurality of pixels including a switching TFT 611, a current controlling TFT 612, and a first electrode 613 electrically connected to a drain of the current controlling TFT 612. An insulator 614 is formed to cover the end portions of the first electrode 613. Here, the insulator 614 is formed using a positive type photosensitive acrylic resin film.

In order to improve the coverage, the insulator 614 is formed to have a curved surface with curvature at its upper or lower end portion. For example, in the case of using positive photosensitive acrylic for the insulator 614, only the upper end portion of the insulator 614 preferably has a curved surface with a radius of curvature of 0.2 to 3 μm. As the insulator 614, either a negative type which becomes insoluble in etchant by irradiation with light or a positive type which becomes soluble in etchant by irradiation with light can be used.

A layer 616 containing an organic compound and a second electrode 617 are formed over the first electrode 613. As a material used for the first electrode 613 which functions as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like can be used. Alternatively, a stack of a titanium nitride film and a film containing aluminum as its main component, a stack of three layers of a titanium nitride film, a film containing aluminum as its main component, and a titanium nitride film, or the like can be used. When the first electrode 613 has a stacked structure, resistance as a wiring is low, a good ohmic contact is formed, and further, the first electrode 613 can be made to function as an anode.

In addition, the layer 616 containing an organic compound is formed by any of a variety of methods such as an evaporation method using an evaporation mask, an inkjet method, and a spin coating method. The layer 616 containing an organic compound contains any of the carbazole compounds described in Embodiment 1. Further, the layer 616 containing an organic compound may be formed using another material such as a low molecular compound or a high molecular compound (the category of the high molecular compound includes an oligomer and a dendrimer).

As a material used for the second electrode 617, which is formed over the layer 616 containing an organic compound and serves as a cathode, a material having a low work function (such as Al, Mg, Li, Ca, or an alloy or compound thereof, such as MgAg, MgIn, or AlLi) is preferably used. In the case where light generated in the layer 616 containing an organic compound passes through the second electrode 617, the second electrode 617 is preferably formed using a stack of a thin metal film and a transparent conductive film (ITO, indium oxide containing zinc oxide at 2 wt % to 20 wt %, indium tin oxide containing silicon, zinc oxide (ZnO), or the like).

Note that the light-emitting element is formed by the first electrode 613, the layer 616 containing an organic compound, and the second electrode 617. The light-emitting element has any of the structures described in Embodiment 4 or Embodiment 5. Note that the pixel portion, which includes a plurality of light-emitting elements, in the light-emitting device of this embodiment may include both the light-emitting element having any of the structures described in Embodiment 4 or Embodiment 5 and the light-emitting element having a structure other than that.

Further, a light-emitting element 618 is provided in the space 607 surrounded with the element substrate 610, the sealing substrate 604, and the sealing material 605 by pasting the sealing substrate 604 and the element substrate 610 using the sealing material 605. The space 607 may be filled with filler, and may be filled with an inert gas (such as nitrogen or argon), the sealing material 605, or the like.

An epoxy based resin is preferably used for the sealing material 605. A material used for them is desirably a material which does not transmit moisture or oxygen as much as possible. As a material for the sealing substrate 604, a plastic substrate made of FRP (Fiberglass-Reinforced Plastics), PVF (polyvinyl fluoride), polyester, acrylic, or the like can be used besides a glass substrate or a quartz substrate.

In this manner, the light-emitting device manufactured using the light-emitting element containing any of the carbazole compounds described in Embodiment 1 can be obtained.

Since the light-emitting device in this embodiment is formed using the light-emitting element containing any of the carbazole compounds described Embodiment 1, a light-emitting device having favorable characteristics can be provided. Specifically, since any of the carbazole compounds described in Embodiment 1 has a wide energy gap and high triplet excitation energy and can suppress energy transfer from a light-emitting substance, a light-emitting element with high emission efficiency can be provided; thus, a light-emitting device with less power consumption can be provided. In addition, since a light-emitting element driven with a low driving voltage can be provided, a light-emitting device driven with a low driving voltage can be provided. Further, since the light-emitting element formed using any of the carbazole compounds described in Embodiment 1 has a long lifetime, a light-emitting device with high reliability can be provided.

Figure 4A:
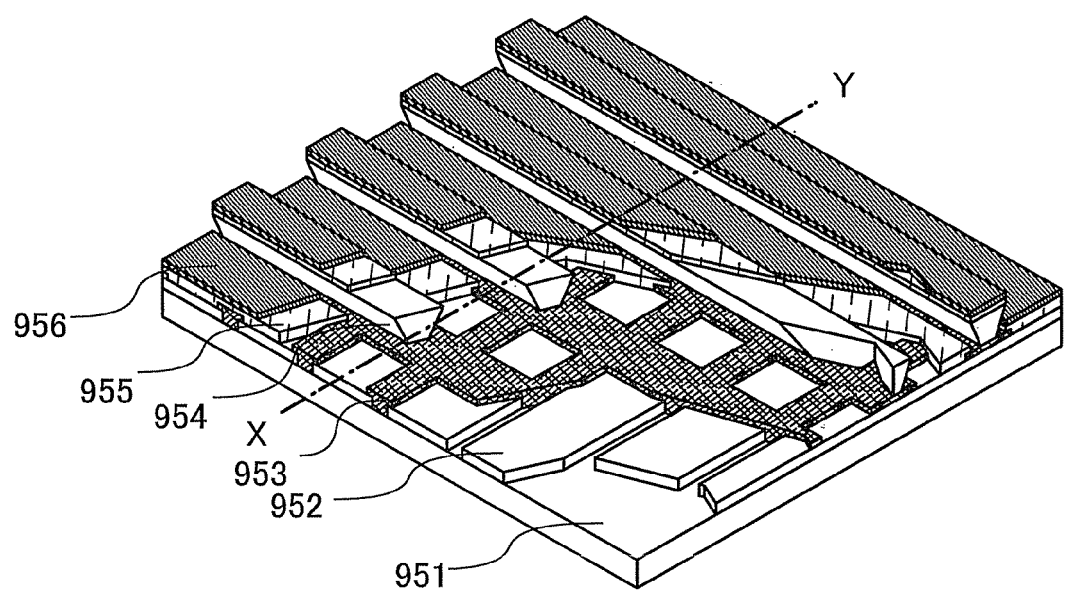
FIGS. 4A and 4B are conceptual diagrams of a passive matrix light-emitting device.
Figure 4B:
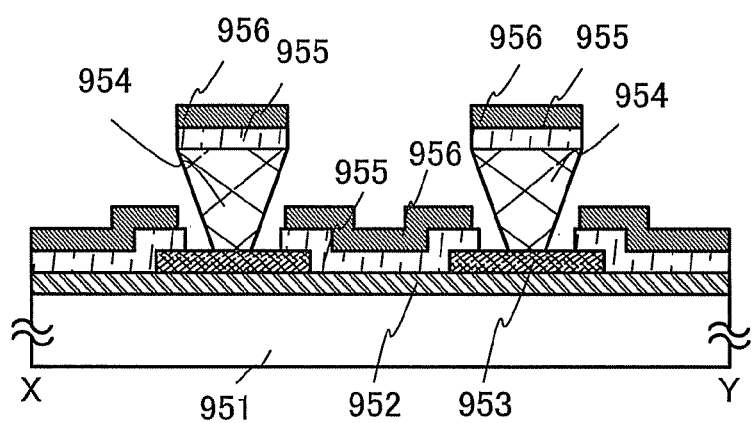

Although an active matrix light-emitting device is described in this embodiment as described above, a passive matrix light-emitting device may be alternatively manufactured. FIGS. 4A and 4B illustrate a passive matrix light-emitting device manufactured according to the present invention. FIG. 4A is a perspective view of the light-emitting device, and FIG. 4B is a cross-sectional view taken along line X-Y in FIG. 4A. In FIGS. 4A and 4B, an electrode 952 and an electrode 956 are provided over a substrate 951, and a layer 955 containing an organic compound is provided between the electrodes 952 and 956. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. That is, a cross section in a short side of the partition layer 954 is a trapezoidal shape, and a lower side (the side which faces in the direction similar to a plane direction of the insulating layer 953 and is in contact with the insulating layer 953) is shorter than an upper side (the side which faces in the direction similar to a plane direction of the insulating layer 953 and is not in contact with the insulating layer 953). By providing the partition layer 954 in this manner, defects of the light-emitting element due to static charge and the like can be prevented. The passive matrix light-emitting device can also be driven with low power consumption by including the light-emitting element according to Embodiment 4 or Embodiment 5, which contains any of the carbazole compounds described in Embodiment 1 and is operated with a low driving voltage. In addition, the light-emitting device can be driven with low power consumption by including the light-emitting element according to Embodiments 4 or Embodiment 5, which contains any of the carbazole compounds described in Embodiment 1 and accordingly has high emission efficiency. Further, the light-emitting device can have high reliability by including the light-emitting element according to Embodiment 4 or Embodiment 5, which contains any of the carbazole compounds described in Embodiment 1.

Embodiment 7

In Embodiment 7, electronic devices each of which includes, as a part thereof, the light-emitting device described in Embodiment 6 is described. Since the light-emitting device described in Embodiment 6 includes the light-emitting element containing any of the carbazole compounds described in Embodiment 1, the power consumption of the light-emitting device is reduced; as a result, electronic devices described in this embodiment can be electronic devices having a display portion with low power consumption. In addition, electronic devices driven with a low driving voltage can be provided. Further, electronic devices having high reliability can be provided.

Examples of the electronic devices to which the light-emitting device is applied include television sets (also referred to as televisions or television receivers), monitors of computers or the like, cameras such as digital cameras or digital video cameras, digital photo frames, cellular phones (also referred to as mobile phones or cellular phone sets), portable game consoles, portable information terminals, audio reproducing devices, large game machines such as pachinko machines, and the like. Specific examples of these electronic devices are described below.

Figure 5A:
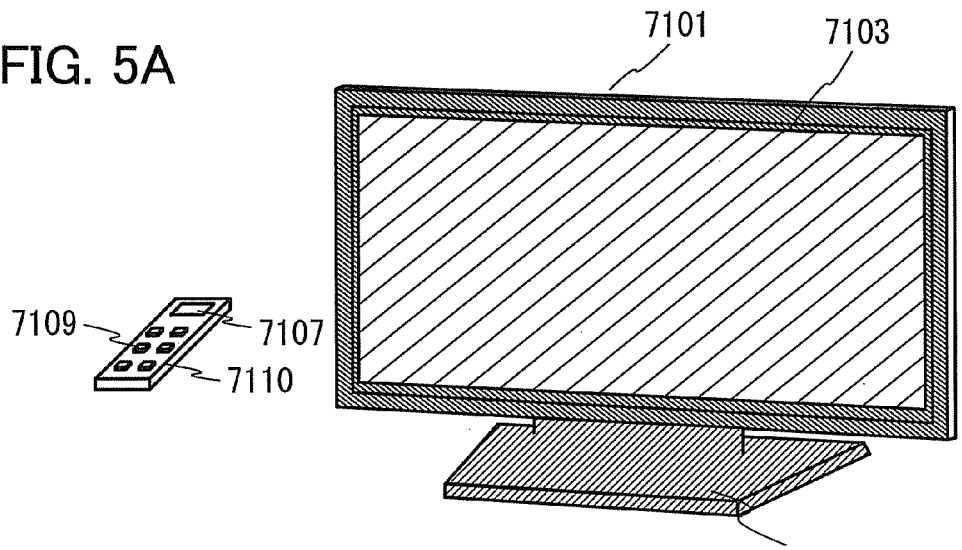
FIGS. 5A to 5D each illustrate an electronic device.

FIG. 5A illustrates an example of a television device. In the television device, a display portion 7103 is incorporated in a housing 7101. In addition, here, the housing 7101 is supported by a stand 7105. Images can be displayed on the display portion 7103, and the display portion 7103 is formed using light-emitting elements arranged in matrix, each of which is similar to that described in Embodiment 4 or Embodiment 5. The light-emitting elements can have high emission efficiency because each light-emitting element contains any of the carbazole compounds described in Embodiment 1. In addition, a light-emitting element driven with a low driving voltage can be provided. Further, a light-emitting element having high reliability can be provided. Therefore, this television device having the display portion 7103 which is formed using the light-emitting elements consumes less power. In addition, a television device driven with a low driving voltage can be provided. Further, a television device having high reliability can be provided.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

Figure 5B:
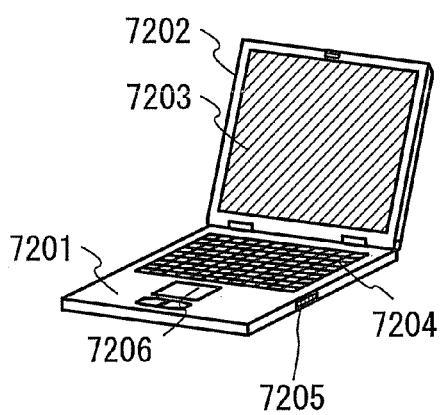

FIG. 5B illustrates a computer having a main body 7201, a housing 7202, a display portion 7203, a keyboard 7204, an external connection port 7205, a pointing device 7206, and the like. Note that this computer is formed using light-emitting elements arranged in matrix, each of which is similar to that described in Embodiment 4 or Embodiment 5, for the display portion 7203. The light-emitting elements can have high emission efficiency because each light-emitting element contains any of the carbazole compounds described in Embodiment 1. In addition, a light-emitting element driven with a low driving voltage can be provided. Further, a light-emitting element having high reliability can be provided. Therefore, this computer having the display portion 7203 which is formed using the light-emitting elements consumes less power. In addition, a computer driven with a low driving voltage can be provided. Further, a computer having high reliability can be provided.

Figure 5C:
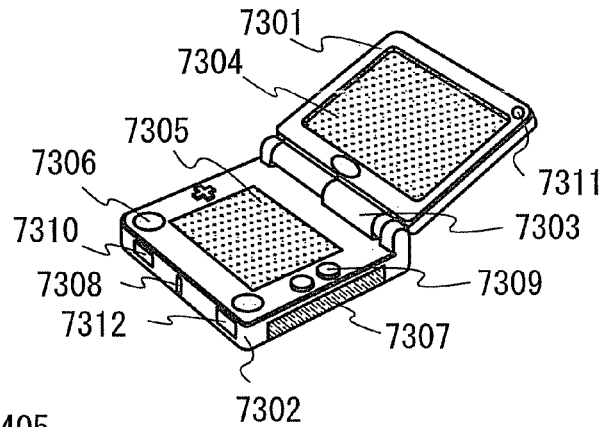

FIG. 5C illustrates a portable game machine having two housings, a housing 7301 and a housing 7302, which are connected with a joint portion 7303 so that the portable game machine can be opened or folded. A display portion 7304 formed using light-emitting elements arranged in matrix, each of which is similar to that described in Embodiment 4 or Embodiment 5 is incorporated in the housing 7301, and a display portion 7305 is incorporated in the housing 7302. In addition, the portable game machine illustrated in FIG. 5C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. Needless to say, the structure of the portable game machine is not limited thereto, and at least one of or both the display portions 7304 and 7305 is/are formed using the light-emitting elements arranged in matrix, each of which is similar to that described in Embodiment 4 or Embodiment 5, and another accessory may be provided as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above. The portable game machine including the above-described display portion 7304 can be a portable game machine with reduced power consumption because the light-emitting elements used in the display portion 7304 have high emission efficiency by containing any of the carbazole compounds described in Embodiment 1. In addition, a portable game machine driven with a low driving voltage can be provided because the light-emitting elements used in the display portion 7304 can be driven with a low driving voltage by containing any of the carbazole compounds described in Embodiment 1. Further, a portable game machine with high reliability can be provided because the light-emitting elements used in the display portion 7304 have high reliability by containing any of the carbazole compounds described in Embodiment 1.

Figure 5D:
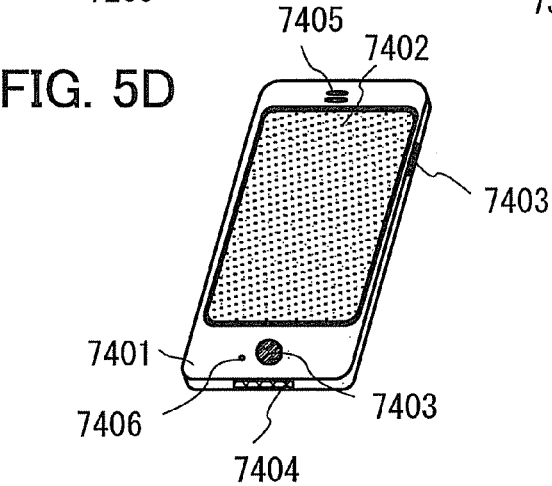

FIG. 5D illustrates an example of a mobile phone. The mobile phone is provided with a display portion 7402 incorporated in a housing 7401, operation buttons 7403, an external connection port 7404, a speaker 7405, a microphone 7406, and the like. Note that the mobile phone includes the display portion 7402 formed using light-emitting elements arranged in matrix, each of which is similar to that described in Embodiment 4 or Embodiment 5. The light-emitting elements can have high emission efficiency because each light-emitting element contains any of the carbazole compounds described in Embodiment 1. In addition, a light-emitting element driven with a low driving voltage can be provided. Further, a light-emitting element having high reliability can be provided. Therefore, this mobile phone having the display portion 7402 which is formed using the light-emitting elements consumes less power. In addition, a mobile phone driven with a low driving voltage can be provided. Further, a mobile phone having high reliability can be provided.

When the display portion 7402 of the mobile phone illustrated in FIG. 5D is touched with a finger or the like, data can be input into the mobile phone. In this case, operations such as making a call and creating e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating an e-mail, a text input mode mainly for inputting text is selected for the display portion 7402 so that text displayed on a screen can be input. In that case, it is preferable to display a keyboard or number buttons on almost all the area of the screen of the display portion 7402.

When a detection device which includes a sensor for detecting inclination, such as a gyroscope or an acceleration sensor, is provided inside the mobile phone, the direction of the mobile phone (whether the mobile phone is placed horizontally or vertically for a landscape mode or a portrait mode) is determined so that display on the screen of the display portion 7402 can be automatically switched.

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a light source for sensing which emits a near-infrared light in the display portion, an image of a finger vein, a palm vein, or the like can be taken.

Note that the structure described in this embodiment can be combined with any of the structures described in Embodiments 1 to 6 as appropriate.

As described above, the application range of the light-emitting device including the light-emitting elements, such as the light-emitting element described in Embodiment 4 or Embodiment 5, containing any of the carbazole compounds described in Embodiment 1, is extremely wide; therefore, the light-emitting device can be applied to electronic devices of a variety of fields. By using any of the carbazole compounds described in Embodiment 1, an electronic device with reduced power consumption can be provided. In addition, an electronic device driven with a low driving voltage can be provided. Further, an electronic device having high reliability can be provided.

The light-emitting device described in Embodiment 6 can also be used as a lighting device. One embodiment in which the light-emitting device described in Embodiment 6 is used as a lighting device is described with reference to FIG. 6.

Figure 6:
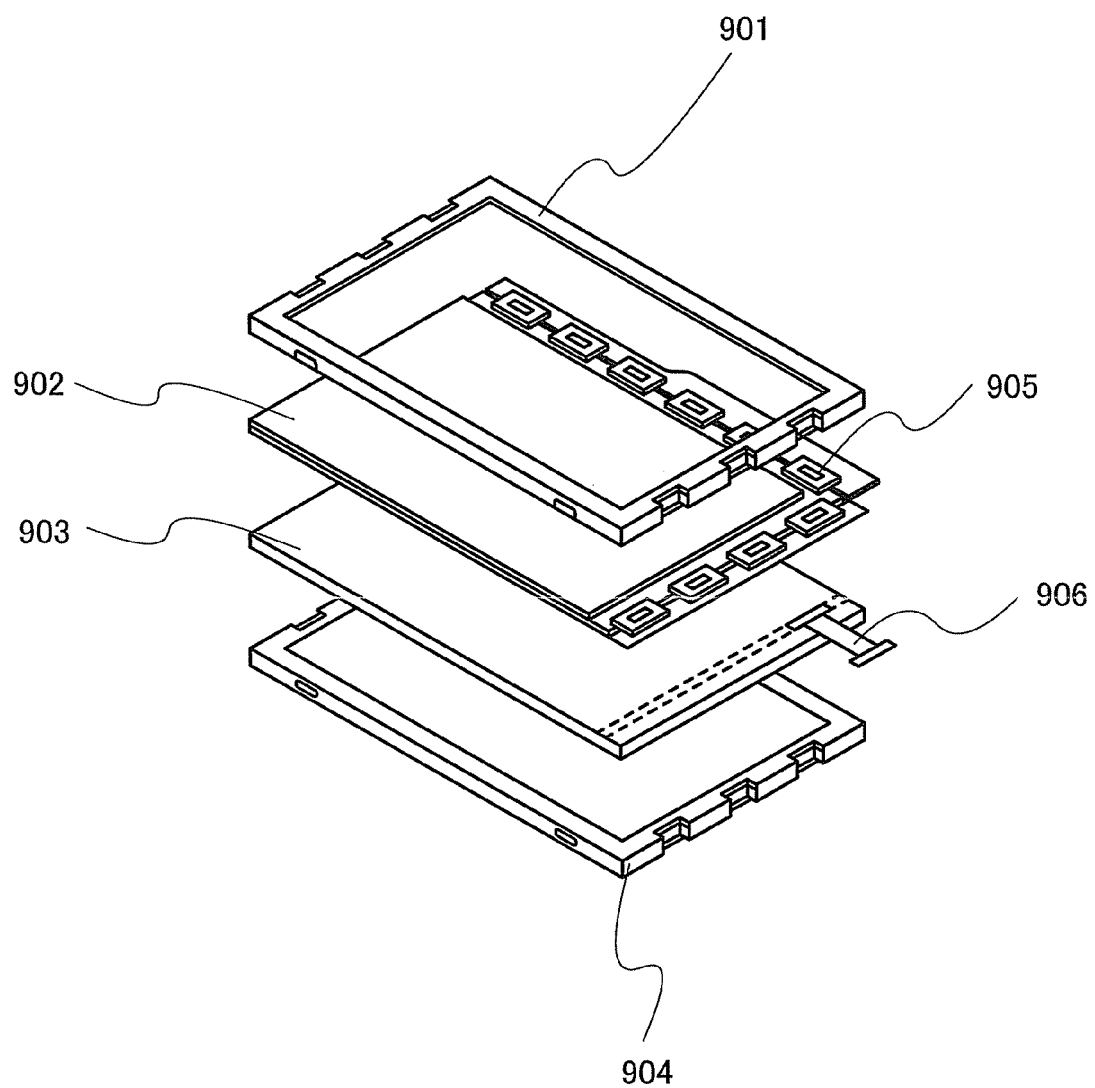
FIG. 6 illustrates an electronic device.

FIG. 6 illustrates an example of a liquid crystal display device using the light-emitting device described in Embodiment 6 as a backlight. The liquid crystal display device shown in FIG. 6 includes a housing 901, a liquid crystal layer 902, a backlight 903, and a housing 904. The liquid crystal layer 902 is connected to a driver IC 905. The light-emitting device of Embodiment 6 is used as the backlight 903, to which current is supplied through a terminal 906.

With the use of the light-emitting device described in Embodiment 6 as the backlight of the liquid crystal display device, a backlight with less power consumption can be provided. Further, the light-emitting device described in Embodiment 6 is a lighting device with plane light emission and can have a large area. Therefore, the backlight can have a large area, and a liquid crystal display device having a large area can be obtained. Furthermore, since the light-emitting device described in Embodiment 6 is thin, it becomes possible to reduce the thickness of a display device.

Figure 7:
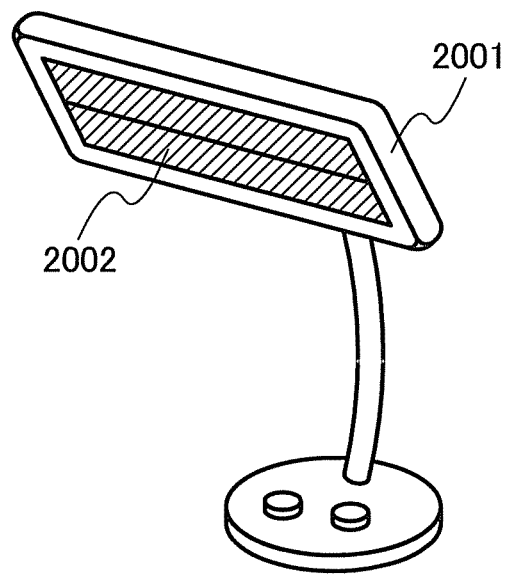
FIG. 7 illustrates a lighting device.

FIG. 7 illustrates an example in which the light-emitting device described in Embodiment 6 is used as a table lamp which is a lighting device. The table lamp illustrated in FIG. 7 includes a housing 2001 and a light source 2002, and the light-emitting device described in Embodiment 6 is used as the light source 2002.

Figure 8:
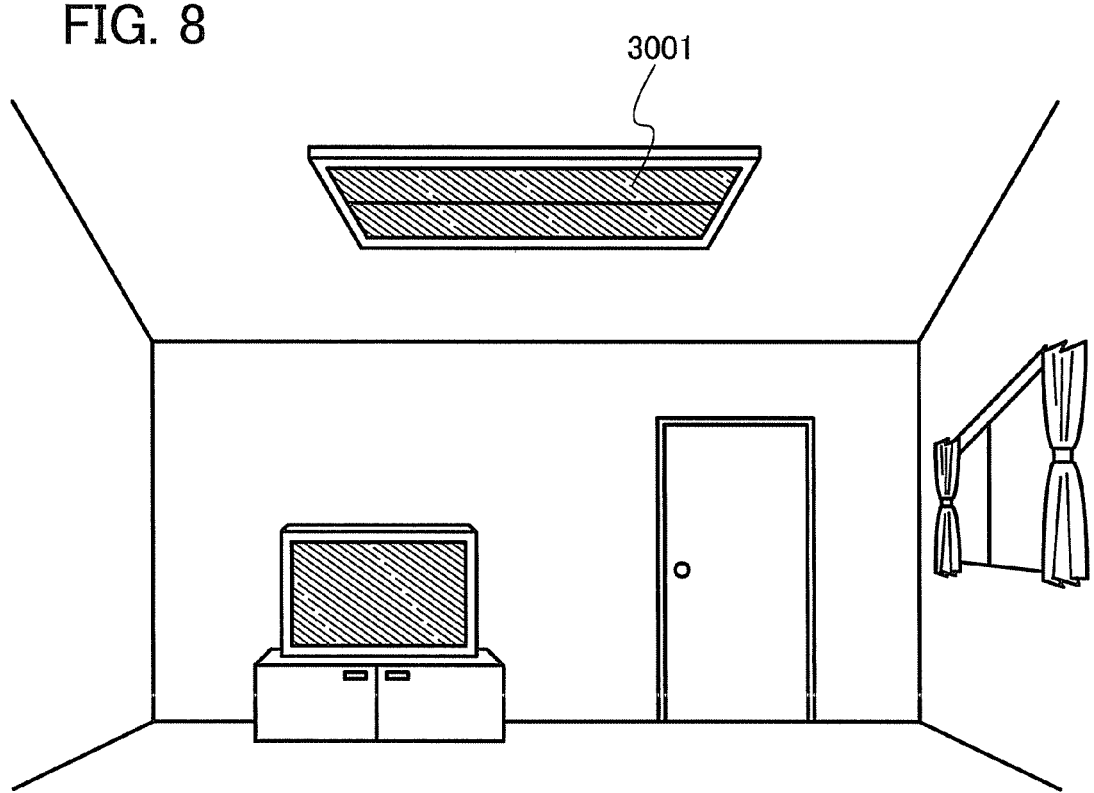
FIG. 8 illustrates a lighting device.

FIG. 8 illustrates an example in which the light-emitting device described in Embodiment 6 is used as an indoor lighting apparatus 3001. Since the light-emitting device described in Embodiment 6 consumes less power, a lighting device that consumes less power can be obtained. Further, since the light-emitting device described in Embodiment 6 can have a large area, the light-emitting device can be used as a large-area lighting apparatus. Further, since the light-emitting device described in Embodiment 6 is thin, the light-emitting device can be used for a lighting device having reduced thickness.

Figure 9:
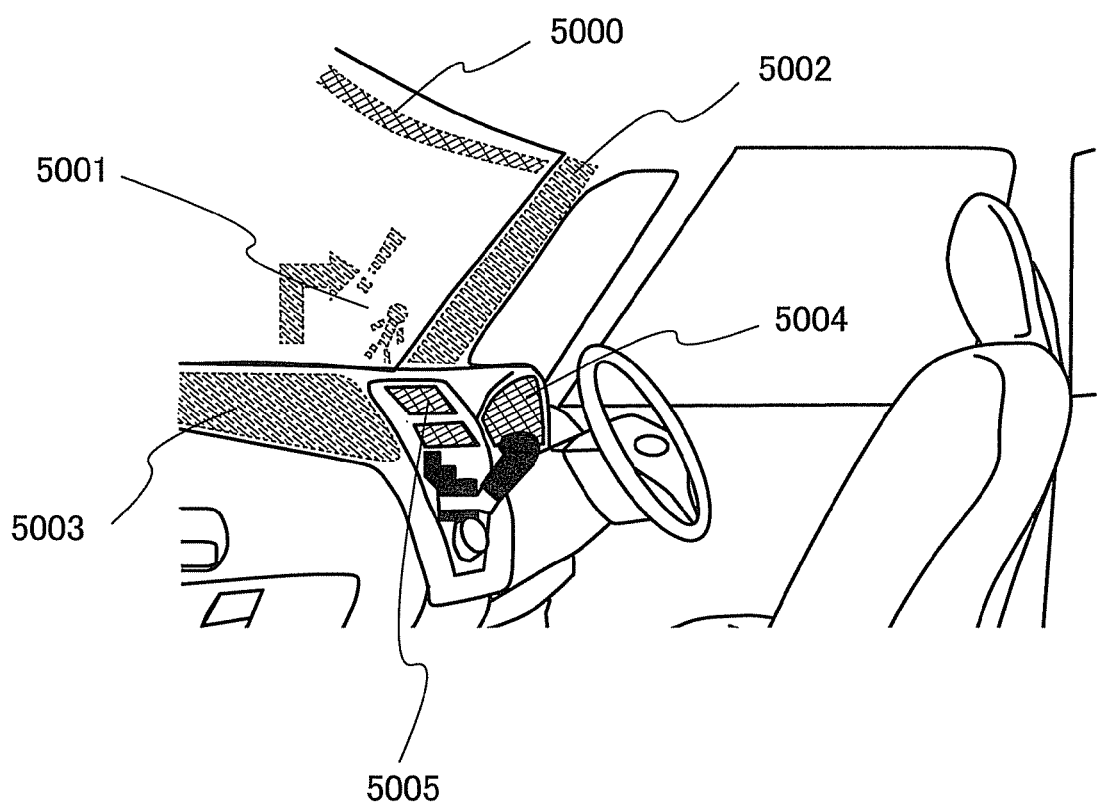
FIG. 9 illustrates car-mounted display devices and lighting devices.

The light-emitting element described in Embodiment 6 can be used for a windshield or a dashboard on a car. FIG. 9 illustrates one embodiment in which the light-emitting device described in Embodiment 6 is used for a windshield or a dashboard on a car. Displays 5000 to 5005 each include the light-emitting device described in Embodiment 6.

The display 5000 and the display 5001 are light-emitting devices provided in the windshield on the car, which are described in Embodiment 6. The light-emitting devices described in Embodiment 6 can be so-called see-through display devices, through which the opposite side can be seen, because a first electrode and a second electrode are formed using light-transmitting materials. Such see-through display devices can be provided even in the windshield on the car, without hindering the vision. In addition, for example, when a transistor for driving the light-emitting element is provided, a transistor having a light-transmitting property, such as an organic transistor using an organic semiconductor material or a transistor using an oxide semiconductor, is preferably used.

The display 5002 is a display device provided in a pillar portion. The display 5002 can compensate for the view hindered by the pillar portion by showing an image taken by an imaging unit provided in the car body. Similarly, the display 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see, makes it possible for the driver to confirm safety easily and comfortably.

The display 5004 and the display 5005 can provide a variety of kinds of information such as information of navigation, speedometer, tachometer, mileage (travel distance), fuel meter, gearshift indicator, and air condition. The content or layout of the display can be changed freely by a user as appropriate. Further, such information can also be shown in the displays 5000 to 5003. Note that the displays 5000 to 5005 can be used as lighting devices by light emission on the entire areas of the displays 5000 to 5005.

Since the light-emitting device described in Embodiment 6 includes any of the carbazole compounds described in Embodiment 1, it can be driven with a low driving voltage or reduce power consumption. When a number of large screens are provided, load to a battery can be reduced, which provides comfortable driving.

Example 1

Synthesis Example 1

In this example, described is a method of synthesizing 3-(dibenzofuran-2-yl)-9-[4-(10-phenyl-9-anthryl)phenyl]-9H-carbazole (abbreviation: FrCPA), which is one of the carbazole compounds described in Embodiment 1. A structure of FrCPA is shown in a structural formula below.

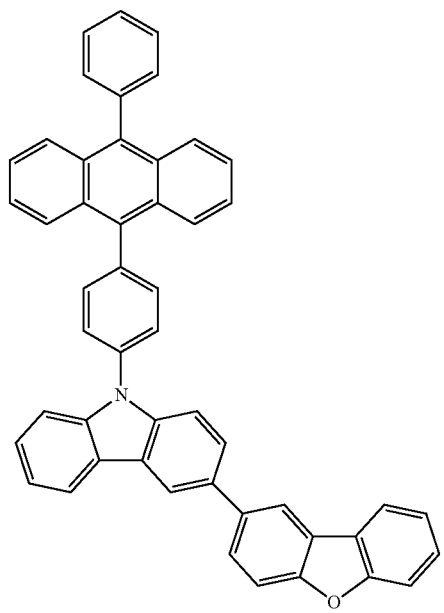 [SMILES: c1ccc(-c2c3ccccc3c(-c3ccc(-n4c5ccccc5c5cc(-c6ccc7oc8ccccc8c7c6)ccc54)cc3)c3ccccc23)cc1]

Step 1: Synthesis of 2-Iododibenzofuran

In a 500-mL three-neck flask, a suspension of 8.4 g (50 mmol) of dibenzofuran, 6.2 g (25 mmol) of iodine, 5.7 g (25 mmol) of orthoperiodic acid, 150 mL of glacial acetic acid, 30 mL of water, and 500 µL of sulfuric acid was heated and stirred at 60° C. for 4.5 hours. After that, the mixture was stirred at room temperature for 16 hours. The generated precipitate was collected by filtration, and the resulting matter was dissolved in 150 mL of toluene and a toluene solution was made. This toluene solution was washed with water three times. After the washing, magnesium sulfate was added to the toluene solution to adsorb moisture. This mixture was filtered and the given filtrate was concentrated. After that, hexane was added, and the mixture was irradiated with ultrasonic waves to perform recrystallization, so that 11.3 g of white powder, which was the objective substance, was obtained in 77% yield. A synthetic scheme of Step 1 is shown in (a-1) below.

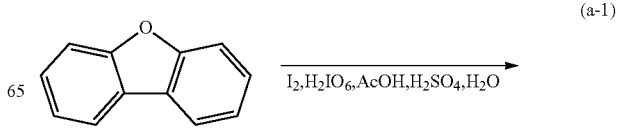

(a-1)

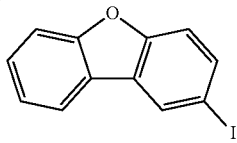

Step 2: Synthesis of Dibenzofuran-2-boronic acid

Into a 500-mL three-neck flask was put 5.0 g (17 mmol) of 2-iodedibenzofuran, and the air in the flask was replaced with nitrogen. Into this flask was added 150 mL of tetrahydrofuran (THF), and this solution was cooled to −80° C. Then, 13 mL (20 mmol) of n-butyllithium (a 1.6 mol/L hexane solution) was dripped into this solution with a syringe. After the dripping, this solution was stirred at the same temperature for 1 hour. After the solution was stirred, to this solution was added 2.8 mL (25 mmol) of trimethyl borate, and the mixture was stirred for about 15 hours while the temperature of the mixture was being brought back to room temperature. After the stirring, about 50 mL of dilute hydrochloric acid (1.0 mol/L) was added to this solution, followed by stirring for 1 hour. After the stirring, the aqueous layer of this mixture was extracted with ethyl acetate, and the solution of the extract was combined with the organic layer, and washed with a saturated aqueous solution of sodium hydrogen carbonate and saturated brine. The organic layer was dried with magnesium sulfate. After the drying, the mixture was filtered. The obtained filtrate was concentrated, so that a pale brown solid was obtained. This solid was recrystallized with toluene/hexane to give 2.0 g of a white powder, which was the objective substance, in 55% yield. The synthesis scheme of Step 2 is shown in (a-2).

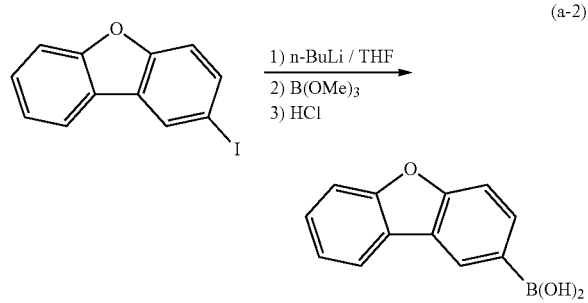

(a-2)

Step 3: Synthesis of 3-(Dibenzofuran-2-yl)-9H-carbazole

Into a 300-mL three-neck flask were put 2.3 g (9.4 mmol) of 3-bromo-9H-carbazole, 2.0 g (9.4 mmol) of dibenzofuran-2-boronic acid, and 0.42 g (1.4 mmol) of tris(2-methylphenyl)phosphine. To the mixture were added 30 mL of ethanol, 50 mL of toluene, and 10 mL (2.0 mol/L) of an aqueous solution of potassium carbonate. This mixture was stirred to be degassed while the pressure was reduced. To this mixture was added 63 mg (0.28 mmol) of palladium(II) acetate. This mixture was stirred at 90° C. for 5 hours, cooled to room temperature, and then left for 15 hours; accordingly, a brown solid was precipitated. The precipitated solid was subjected to suction filtration and then collected. The collected solid was dissolved in about 30 mL of hot toluene, and this solution was suction-filtered through Celite (produced by Wako Pure Chemical Industries, Ltd., Catalog No. 531-16855), alumina, and Florisil (produced by Wako Pure Chemical Industries, Ltd., Catalog No. 540-00135). The resulting filtrate was concentrated to give a white solid. This solid was recrystallized with toluene/hexane to give 0.87 g of white powder in 27% yield. The synthesis scheme of Step 3 is shown in (a-3).

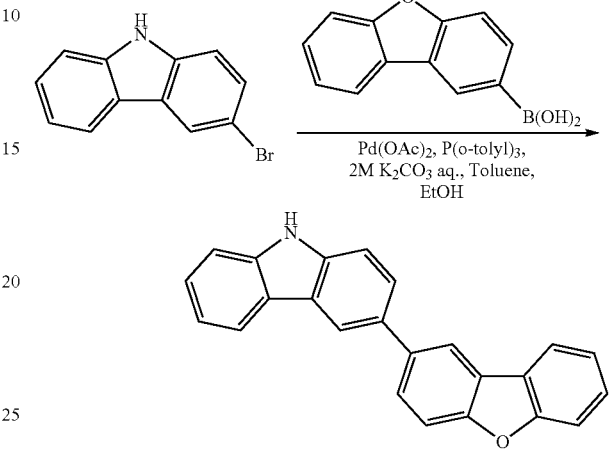

(a-3)

Step 4: Synthesis of 3-(Dibenzofuran-2-yl)-9-[4-(10-phenyl-9-anthryl)phenyl]-9H-carbazole (abbreviation: FrCPA)

Into a 200-mL three-neck flask were put 1.0 g (2.6 mmol) of 9-(4-bromophenyl)-10-phenylanthracene, 0.86 g (2.6 mmol) of 3-(dibenzofuran-2-yl)-9H-carbazole, and 0.50 g (5.2 mmol) of sodium tert-butoxide. The air in the flask was replaced with nitrogen, and then, to the mixture were added 50 mL of toluene and 0.20 mL of tri(tert-butyl)phosphine (a 10 wt % hexane solution). This mixture was degassed under reduced pressure while being stirred, and then 75 mg (0.13 mmol) of bis(dibenzylideneacetone)palladium(0) was added to this mixture. This mixture was stirred at 110° C. for 2 hours under a nitrogen stream. After the stirring, this mixture was subjected to suction filtration through Celite, alumina, and Florisil. The obtained filtrate was concentrated to give a light-yellow oily substance. This oily substance was recrystallized from toluene/hexane to give 1.4 g of light-yellow powder in 80% yield. The synthesis scheme of Step 4 is shown in (a-4).

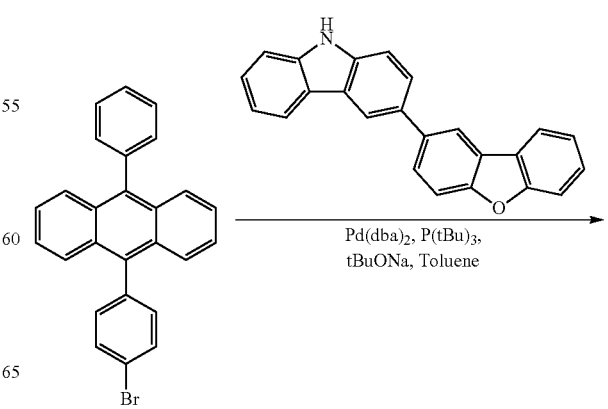

(a-4)

-continued

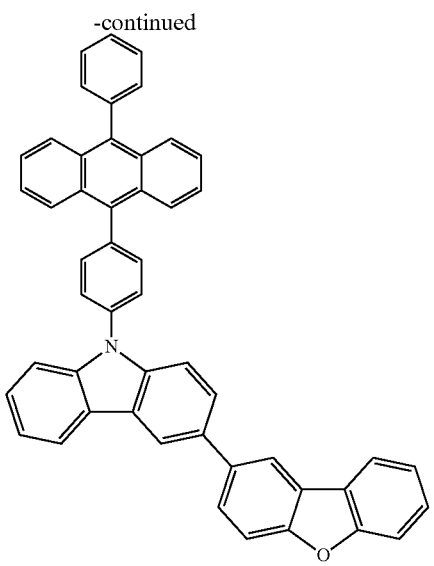

By a train sublimation method, 0.98 g of the obtained pale yellow powdered solid was purified. The purification was conducted by heating FrCPA at 320° C. under a pressure of 10 Pa with a flow rate of argon gas of 4.0 mL/min. After the purification, 0.87 g of a pale yellow solid was obtained in 88% yield.

The obtained substance was analyzed by $^1$H NMR. The measurement data are shown below.

$^1$H NMR (CDCl$_3$, 300 MHz): δ=7.37-7.56 (m, 10H), 7.58-7.67 (m, 4H), 7.68-7.79 (m, 7H), 7.82-7.90 (m, 6H), 8.08 (d, J=7.8 Hz, 1H), 8.29 (d, J=4.8 Hz, 1H), 8.31 (s, 1H), 8.49 (sd, J=1.5 Hz, 1H)

Figure 10A:
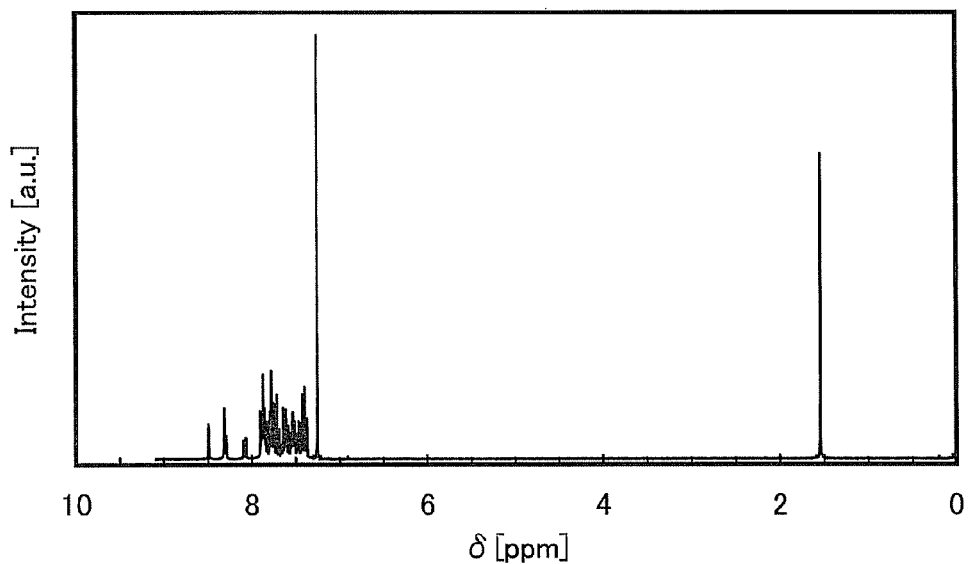
FIGS. 10A and 10B show $^1$H NMR charts of FrCPA.
Figure 10B:
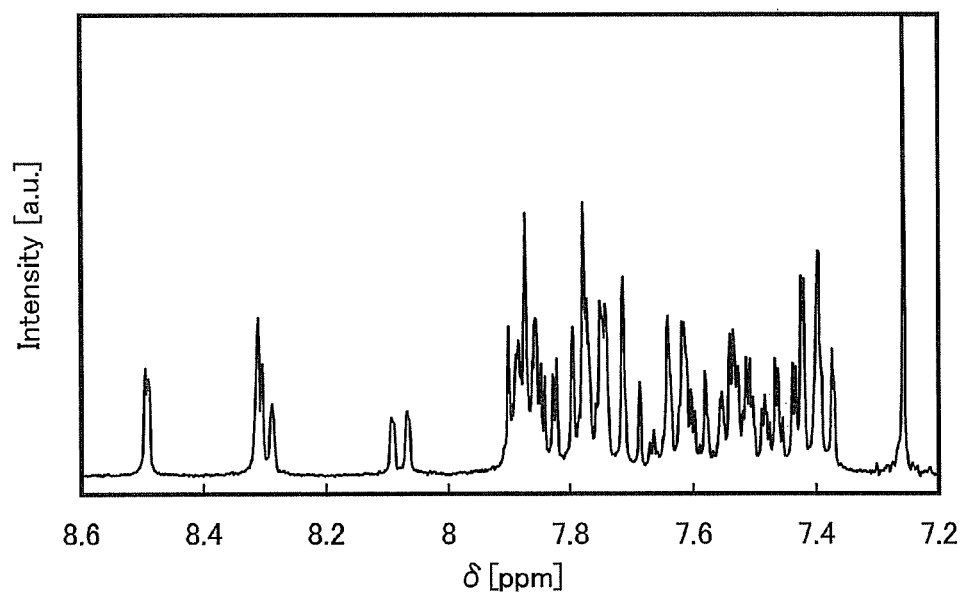

The $^1$H NMR charts are shown in FIGS. 10A and 10B. FIG. 10B is a chart showing an enlarged part of FIG. 10A in the range of 7.2 to 8.6 ppm. The measurement results showed that FrCPA, which is the carbazole compound represented by the above structural formula, was obtained.

The thermogravimetry-differential thermal analysis (TG-DTA) of the obtained FrCPA was performed. For the measurement, a high vacuum differential type differential thermal balance (type TG-DTA2410SA, manufactured by Bruker AXS K.K.) was used. The measurement was performed under normal pressure in a stream of nitrogen (at a flow rate of 200 mL/min) at a rate of temperature increase of 10° C./min. From the relationship between the weight and the temperature (thermogravimetry), it was understood that a 5% weight reduction was seen at temperatures of 477.9° C., and FrCPA has a high heat resistance.

Figure 11A:
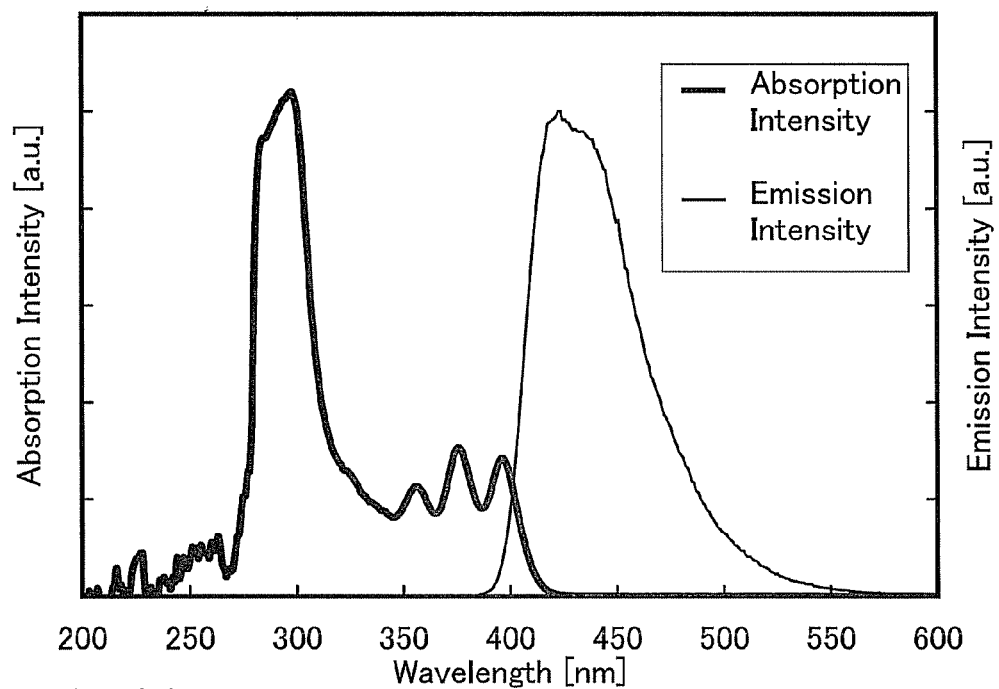
FIGS. 11A and 11B show absorption spectra and emission spectra of FrCPA.
Figure 11B:
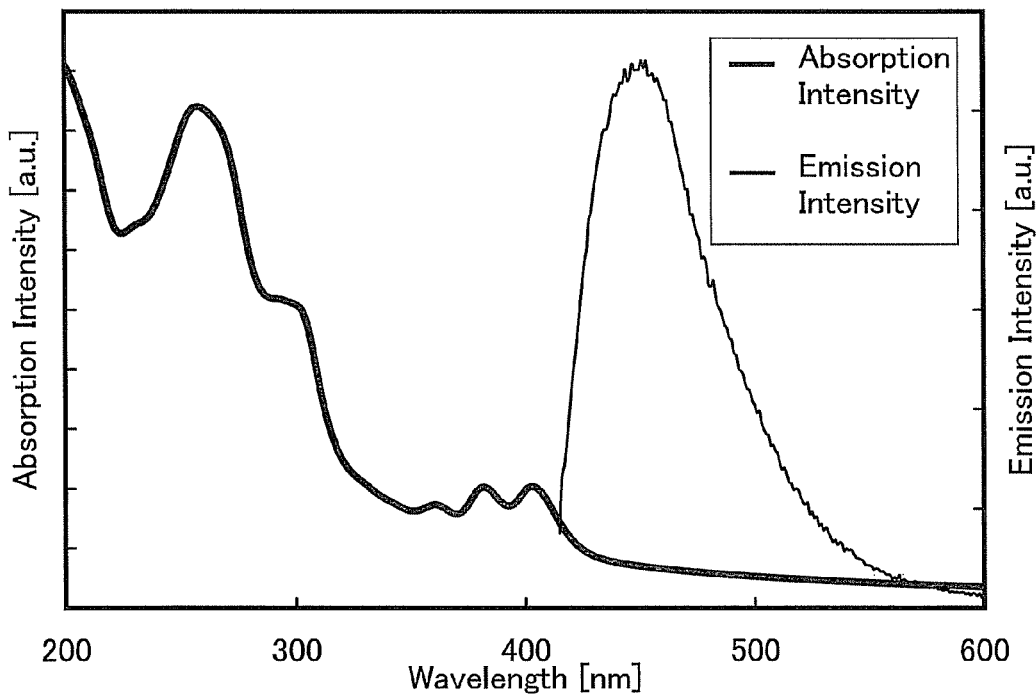

Next, an absorption and emission spectra of FrCPA in a toluene solution of FrCPA are shown in FIG. 11A, and an absorption and emission spectra of a thin film of FrCPA are shown in FIG. 11B. The absorption spectrum was measured with an ultraviolet-visible spectrophotometer (V-550, manufactured by JASCO Corporation). In the case of the toluene solution, the measurements were made with the toluene solution of FrCPA put in a quartz cell, and the absorption spectrum obtained by subtraction of absorption spectra of the quartz cell and toluene from the measured spectrum is shown in the drawing. In addition, as for the absorption spectrum of the thin film, a sample was prepared by evaporation of FrCPA on a quartz substrate, and the absorption spectrum obtained by subtraction of that of quartz from the spectrum of this sample is shown in the drawing. The emission spectrum was measured with the ultraviolet-visible spectrophotometer (V-550, manufactured by JASCO Corporation) which is the same as that for the measurement of the absorption spectrum. The emission spectrum of FrCPA in the toluene solution of FrCPA was measured in a quartz cell, and the emission spectrum of the thin film of FrCPA was measured by fabricating the sample by evaporation of FrCPA over a quartz substrate. Thus, it was found that the greatest emission wavelength of FrCPA in the toluene solution of FrCPA was around 422 nm (at an excitation wavelength of 299 nm), and that the greatest emission wavelength of the thin film of FrCPA was around 452 nm (at an excitation wavelength of 400 nm).

These results indicate that FrCPA, which is one of the carbazole compounds described in Embodiment 1, emits blue light and can be used as a blue light-emitting material.

Further, the ionization potential of FrCPA in a thin film state was measured by a photoelectron spectrometer (AC-2, manufactured by Riken Keiki, Co., Ltd.) in air. The obtained value of the ionization potential was converted to a negative value, so that the HOMO level of FrCPA was −5.73 eV. From the data of the absorption spectra of the thin film in FIG. 11B, the absorption edge of FrCPA, which was obtained from Tauc plot with an assumption of direct transition, was 2.93 eV. Therefore, the optical energy gap of FrCPA in the solid state was estimated at 2.93 eV; from the values of the HOMO level obtained above and this energy gap, the LUMO level of FrCPA was able to be estimated at −2.80 eV. It was thus found that FrCPA had a wide energy gap of 2.93 eV in the solid state.

These results indicate that FrCPA, which is one of the carbazole compounds described in Embodiment 1, has a wide band gap and can be used as a host material of a blue light-emitting material (or a material that emits visible light with a wavelength longer than that of blue).

In addition, oxidation reaction characteristics of FrCPA were measured. The oxidation reaction characteristics were examined by a cyclic voltammetry (CV) measurement. An electrochemical analyzer (ALS model 600A or 600C, manufactured by BAS Inc.) was used for the measurement.

For a solution for the CV measurement, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurement was conducted at room temperature (20 to 25° C.). The scan speed at these CV measurements was set at 0.1 V/s.

Figure 12:
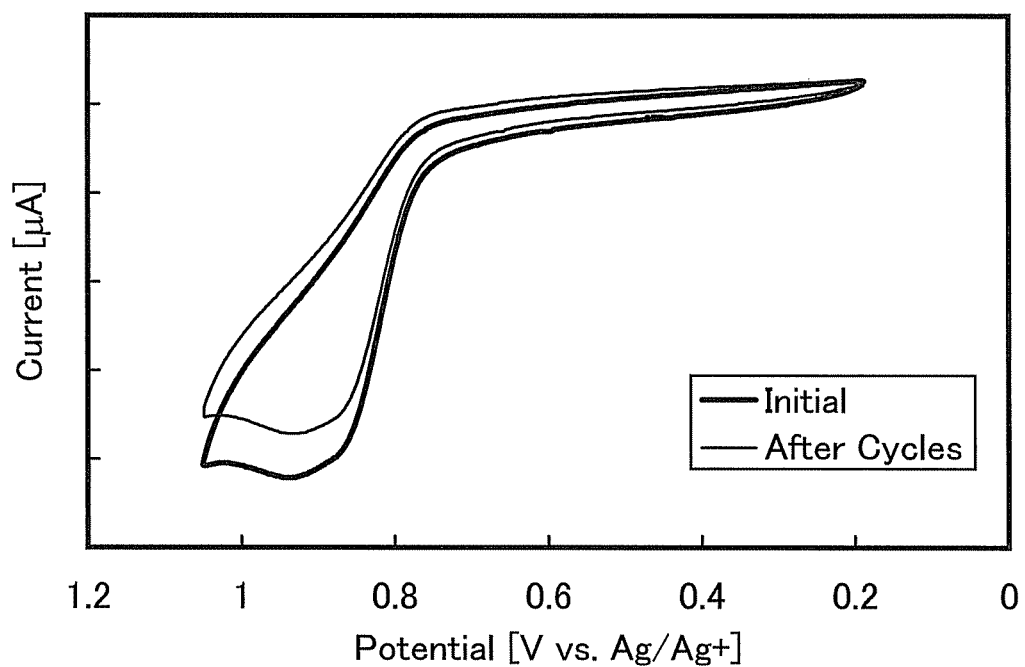
FIG. 12 shows CV charts of FrCPA.

In the measurement, scanning in which the potential of the working electrode with respect to the reference electrode was changed from 0.189 V to 1.05 V and then changed from 1.05 V to 0.189 V was one cycle, and 100 cycles were performed. Results of the measurement are shown in FIG. 12. The measurement results revealed that the oxidation peak kept 88% of the initial state and that FrCPA showed properties effective against repetition of redox reactions between an oxidized state and a neutral state even after the 100 cycles in the measurement.

Furt
her, the HOMO level of FrCPA was determined also by calculation from the CV measurement result.

First, the potential energy of the reference electrode (Ag/Ag$^+$ electrode) with respect to the vacuum level used was found to be −4.94 eV, and the oxidation peak potential $E_{pa}$ of FrCPA was 0.94 V. In addition, the reduction peak potential $E_{pa}$ thereof was 0.74 V. Therefore, a half-wave potential (an intermediate potential between $E_{pa}$ and $E_{pa}$) can be calculated at 0.84 V. This means that FrCPA is oxidized by an electric energy of 0.84 [V versus Ag/Ag$^+$], and this energy corresponds to the HOMO level. Here, since the potential energy of the reference electrode, which was used in this example, with respect to the vacuum level was −4.94 [eV] as described above, the HOMO level of FrCPA was calculated as follows: −4.94−0.84=−5.78 [eV].

Note that the potential energy of the reference electrode (Ag/Ag$^+$ electrode) with respect to the vacuum level corresponds to the Fermi level of the Ag/Ag$^+$ electrode, and should be calculated from a value obtained by measuring a substance whose potential energy with respect to the vacuum level is known, with the use of the reference electrode (Ag/Ag$^+$ electrode).

How the potential energy (eV) of the reference electrode (Ag/Ag$^+$ electrode), which was used in this example, with respect to the vacuum level is determined by calculation is specifically described. It is known that the oxidation-reduction potential of ferrocene in methanol is +0.610 [V vs. SHE] with respect to a standard hydrogen electrode (Reference: Christian R. Goldsmith et al., J. Am. Chem. Soc., Vol. 124, No. 1, pp. 83-96, 2002). On the other hand, using the reference electrode used in this example, the oxidation-reduction potential of ferrocene in methanol was calculated to be +0.11 [V vs. Ag/Ag$^+$]. Therefore, it was found that the potential energy of this reference electrode was lower than that of the standard hydrogen electrode by 0.50 [eV].

Here, it is known that the potential energy of the standard hydrogen electrode with respect to the vacuum level is −4.44 eV (Reference: Toshihiro Ohnishi and Tamami Koyama, High Molecular EL Material, Kyoritsu Shuppan, pp. 64-67). Therefore, the potential energy of the reference electrode used in this example with respect to the vacuum level can be calculated at −4.44−0.50=−4.94 [eV].

Example 2

In this example, described is a light-emitting element (a light-emitting element 1) in which 3-(dibenzofuran-2-yl)-9-[4-(10-phenyl-9-anthryl)phenyl]-9H-carbazole (abbreviation: FrCPA), which is one of the carbazole compounds described in Embodiment 1, is used as a host material in a light-emitting layer including an emission center substance that emits blue fluorescence. As a comparative example, a light-emitting element (a comparative element 1) in which 9-[4-(10-phenyl-9-anthryl)phenyl]-9H-carbazole (abbreviation: CzPA) is used instead of FrCPA was also fabricated at the same time and evaluated.

Molecular structures of organic compounds used in this example are shown in structural formulas (i) to (v) below. An element structure in which an electron-injection layer is provided between an electron-transport layer 114 and a second electrode 104 of the element structure shown in FIG. 1A was employed.

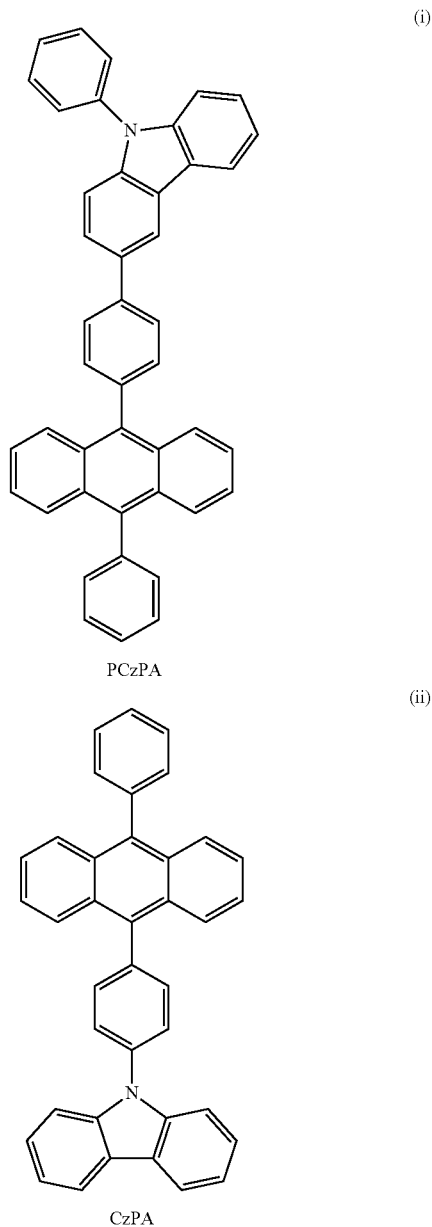

(i) PCzPA (ii) CzPA

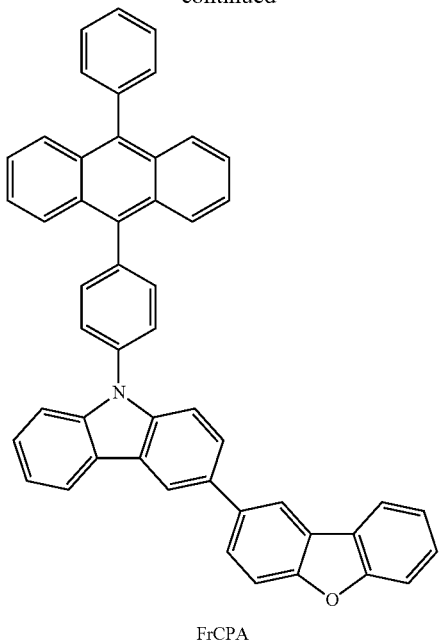

FrCPA

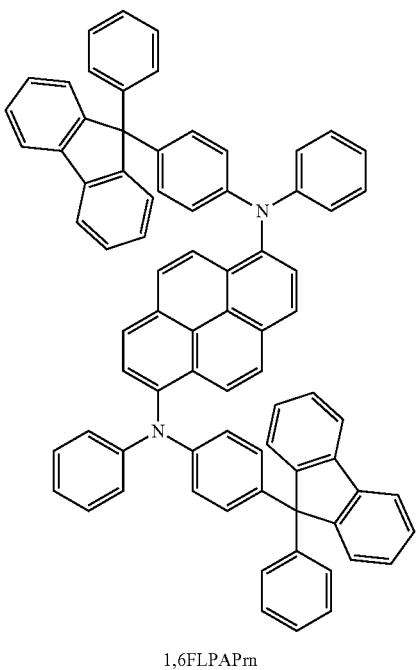

1,6FLPAPrn

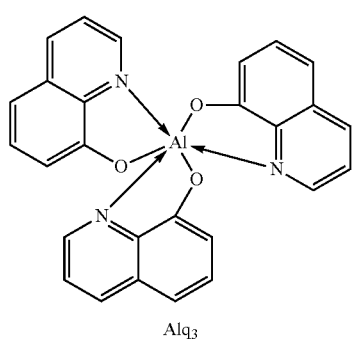

Alq₃

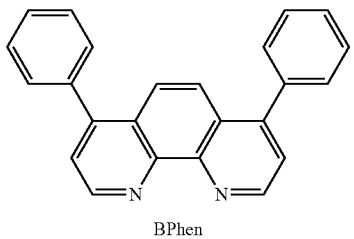

BPhen

[Fabrication of Light-emitting Element 1 and Comparative Element 1]

First, a glass substrate 101 over which indium tin oxide containing silicon (ITSO) with a thickness of 110 nm was formed as a first electrode 102 was prepared. A surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for 1 hour, and then a UV ozone treatment was performed for 370 seconds. After that, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Next, the substrate 101 was fixed on a holder provided in the vacuum evaporation apparatus such that the surface of the substrate 101 provided with ITSO faced downward.

After the pressure in the vacuum evaporation apparatus was reduced to $10^{-4}$ Pa, 9-[4-(9-phenylcarbazol-3-yl)]phenyl-10-phenylanthracene (abbreviation: PCzPA) represented by the structural formula (i) above, and molybdenum(VI) oxide were co-evaporated with a mass ratio of PCzPA to molybdenum oxide being 2:1, whereby a hole-injection layer 111 was formed. The thickness thereof was 50 nm. Note that co-evaporation is an evaporation method in which a plurality of different substances is concurrently vaporized from respective different evaporation sources.

Next, PCzPA was evaporated to a thickness of 10 nm, whereby a hole-transport layer 112 was formed.

Further, in the light-emitting element 1, on the hole-transport layer 112, FrCPA, which is one of the carbazole compounds described in Embodiment 1, and N,N'-bis[4-(9-phenyl-9H-fluoren-9-yl)phenyl]-N,N'-diphenylpyrene-1,6-diamine (abbreviation: 1,6FLPAPrn) represented by the above structural formula (iii) were evaporated to a thickness of 30 nm with a mass ratio of FrCPA to 1,6FLPAPrn being 1:0.05, whereby a light-emitting layer 113 was foliated.

In the comparative element 1, on the hole-transport layer 112, 9-[4-(10-phenyl-9-anthryl)phenyl]-9H-carbazole (abbreviation: CzPA) represented by the above structural formula (II) and 1,6FLPAPm were co-evaporated to a thickness of 30 nm with a mass ratio of CzPA and 1,6FLPAPrn being 1:0.05, whereby a light-emitting layer 113 was formed.

Next, on the light-emitting layer 113, tris(8-quinolinolato)aluminum(III) represented by the above structural formula (iv) was evaporated to a thickness of 10 nm, and then bathophenanthroline (abbreviation: BPhen) represented by the above structural formula (v) was evaporated to a thickness of 15 nm, whereby the electron-transport layer 114 was formed. Further, lithium fluoride was evaporated to a thickness of 1 nm on the electron-transport layer 114, whereby the electron-injection layer was formed. Lastly, aluminum was formed with a thickness of 200 nm as a second electrode 104 which serves as a cathode, whereby the light-emitting element 1 and the comparative element 1 were completed. Note that in the above evaporation process, evaporation was all performed by a resistance heating method.

[Operation Characteristics of Light-emitting Element 1 and Comparative Element 1]

The light-emitting element 1 and the comparative element 1 thus obtained were sealed in a glove box under a nitrogen atmosphere without being exposed to air. After that, the operation characteristics of the light-emitting elements were measured. Note that the measurement was carried out at room temperature (in an atmosphere kept at 25° C.). Note that the light-emitting element 1 and the comparative element 1 were formed over the same substrate, and the light-emitting element 1 and the comparative element 1 except the light-emitting layer 113 were formed in the same steps.

Figure 13:
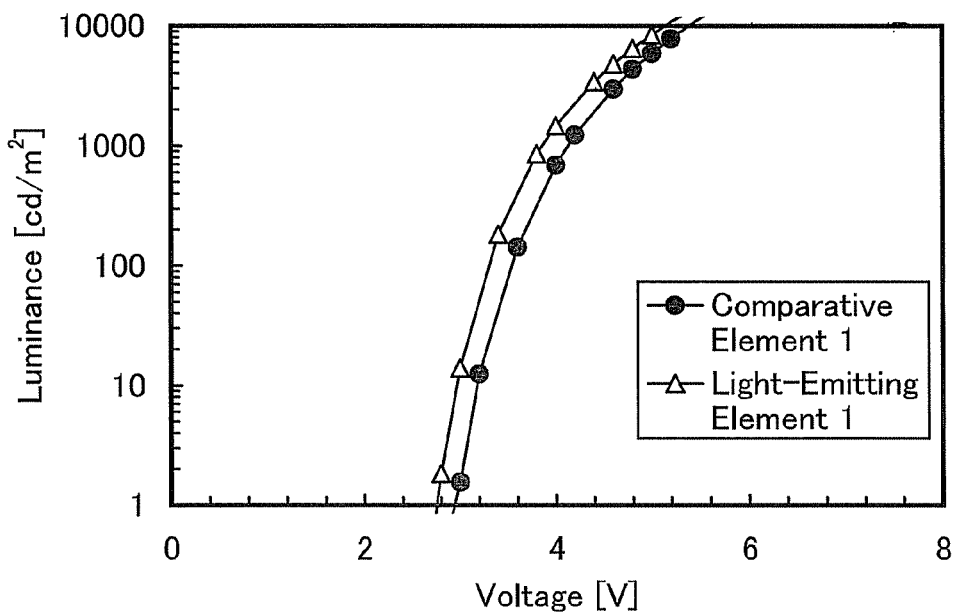
FIG. 13 shows characteristics of luminance versus voltage of a light-emitting element 1 and a comparative element 1.
Figure 14:
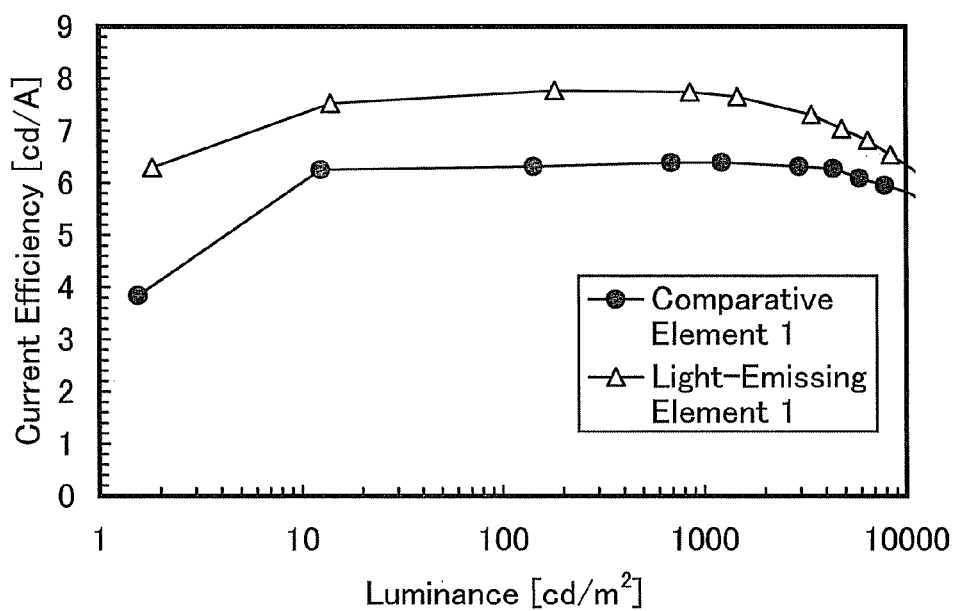
FIG. 14 shows characteristics of current efficiency versus luminance of the light-emitting element 1 and the comparative element 1.
Figure 15:
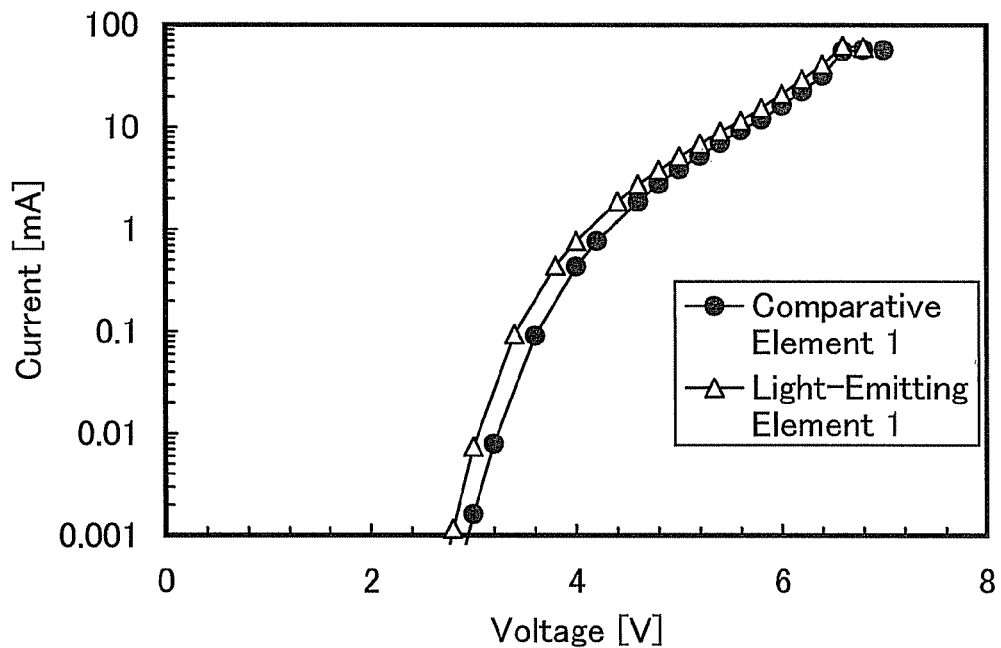
FIG. 15 shows characteristics of current versus voltage of the light-emitting element 1 and the comparative element 1.
Figure 16:
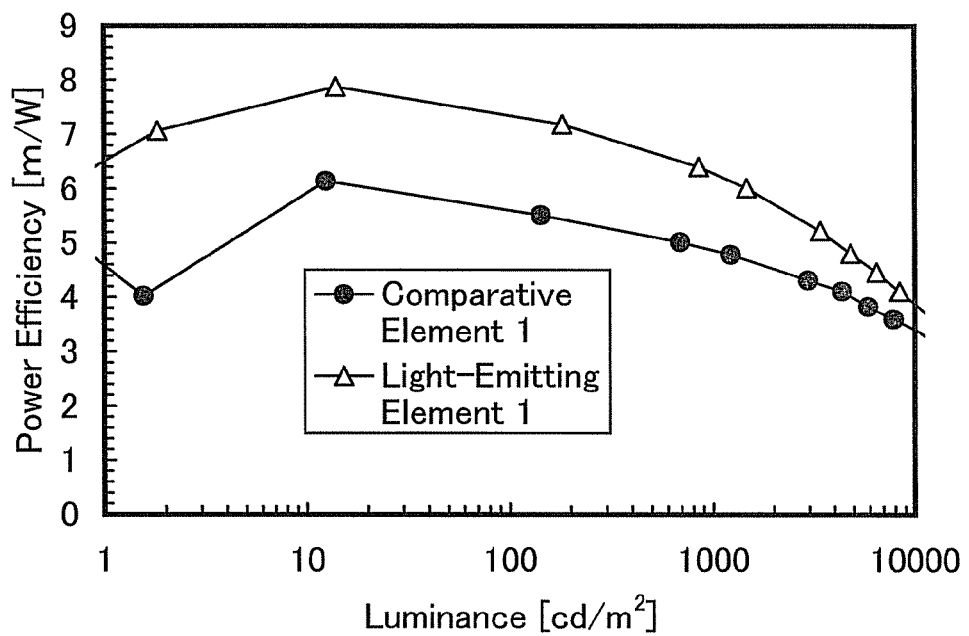
FIG. 16 shows characteristics of power efficiency versus luminance of the light-emitting element 1 and the comparative element 1.
Figure 17:
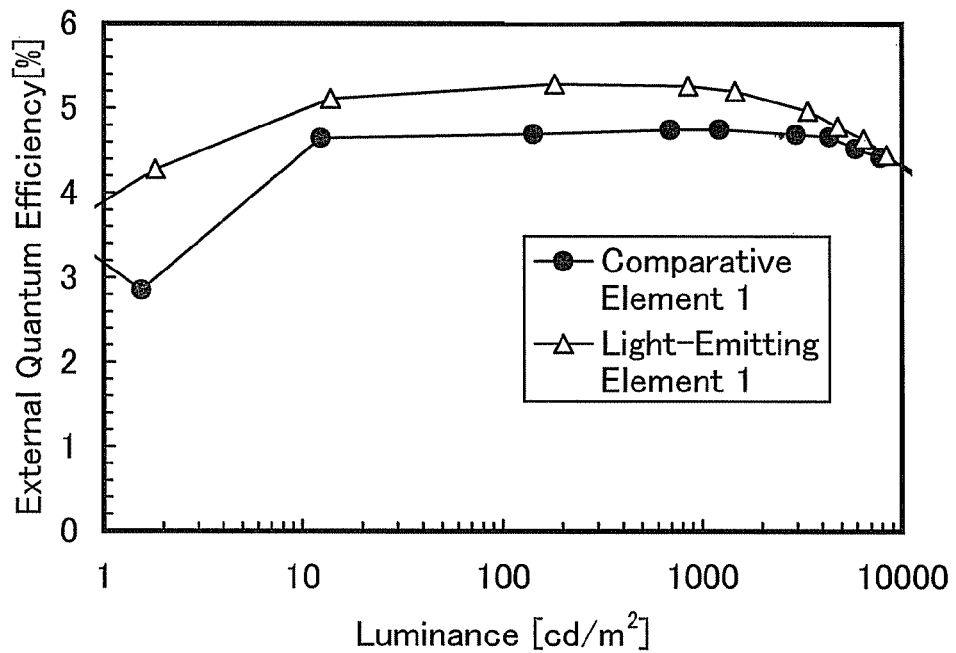
FIG. 17 shows characteristics of external quantum efficiency versus luminance of the light-emitting element 1 and the comparative element 1.

FIG. 13 shows luminance versus voltage characteristics of the light-emitting elements, FIG. 14 shows current efficiency versus luminance characteristics thereof, FIG. 15 shows current versus voltage characteristics thereof, FIG. 16 shows power efficiency versus luminance characteristics thereof, and FIG. 17 shows external quantum efficiency versus luminance characteristics thereof.

From FIG. 14 and FIG. 16, it is found that the light-emitting element 1 in which the carbazole compound described in Embodiment 1 is used as a host material in a light-emitting layer of the light-emitting element that emits blue fluorescence shows favorable characteristics of current efficiency versus luminance and characteristics of power efficiency versus luminance and thus has high emission efficiency. This is because the carbazole compound described in Embodiment 1 has a wide energy gap, and thus even a light-emitting substance that emits blue fluorescence and has a wide energy gap can be effectively excited. In addition, from FIG. 13, it is found that the light-emitting element 1 in which the carbazole compound described in Embodiment 1 is used as a host material in a light-emitting layer of the light-emitting element that emits blue fluorescence shows favorable luminance versus voltage characteristics and is driven with a low driving voltage. Further, FIG. 17 shows favorable characteristics of external quantum efficiency versus luminance of the light-emitting element 1. It is found that there is a significant difference between the light-emitting element 1 and the comparative element 1 which has a similar structure and in which CzPA is used instead of FrCPA.

FIG. 15 shows that the light-emitting element 1 had as favorable characteristics of current versus voltage as the comparative element 1. This indicates that the carbazole compound described in Embodiment 1 has an excellent carrier-transport property.

Figure 18:
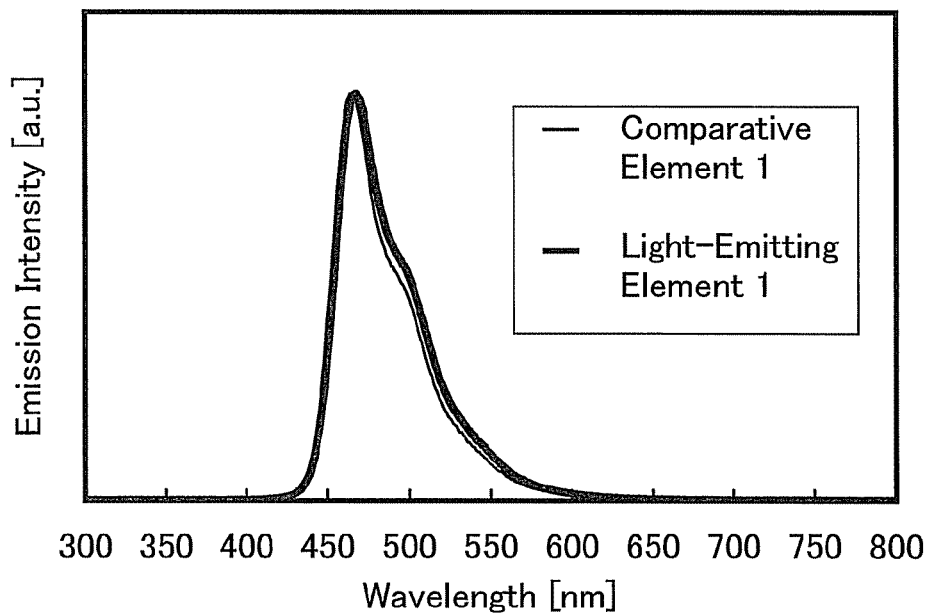
FIG. 18 shows emission spectra of the light-emitting element 1 and the comparative element 1.

FIG. 18 shows emission spectra when a current of 1 mA flows to the obtained light-emitting elements. In FIG. 18, the vertical axis represents emission wavelength (nm), and the horizontal axis represents emission intensity. The emission intensity is shown as a value relative to the maximum emission intensity assumed to be 1. FIG. 18 reveals that the light-emitting element 1 and the comparative element 1 emit blue light due to 1,6FLPAPrn, which is the emission center substance.

Figure 19:
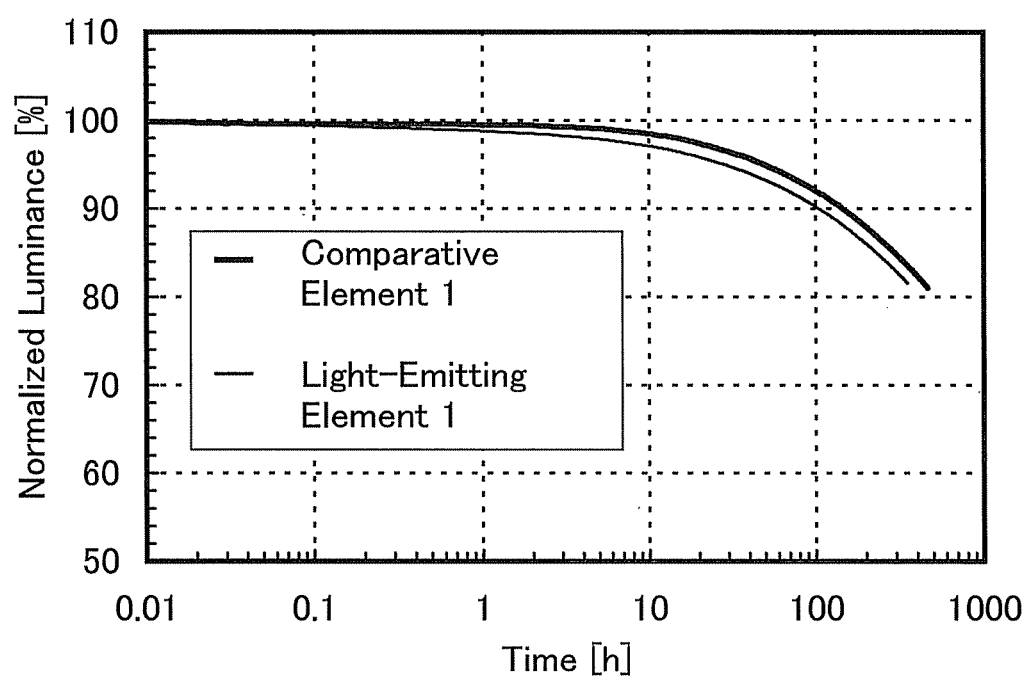
FIG. 19 is a graph showing change of characteristics of normalized luminance versus time of the light-emitting element 1 and the comparative element 1.

Next, the initial luminance is set at 1000 cd/m$^2$, these elements were driven under a condition where the current density was constant, and changes in luminance with respect to the driving time were examined. FIG. 19 shows characteristics of normalized luminance versus time of the light-emitting elements. From FIG. 19, it is found that both the light-emitting element 1 and the comparative element 1 show favorable characteristics and have high reliability.

The evaporation rate of FrCPA, which is one of the carbazole compounds described in Embodiment 1, was very stable when FrCPA was evaporated as a film. Therefore, it is found that FrCPA is a material whose evaporation rate is easy to control and productivity of films is high. In contrast, although the compound CzPA is one of materials having favorable element characteristics, the evaporation rate thereof is hardly stable, resulting in difficulty in fabricating an element.

Reference Example 1

A method of synthesizing N,N'-bis[4-(9-phenyl-9H-fluoren-9-yl)phenyl]-N,N'-diphenylpyrene-1,6-diamine (abbreviation: 1,6FLPAPrn) (structural formula (vi)) used in the above Example is specifically described. A structure of 1,6FLPAPrn is shown below.

(vi)

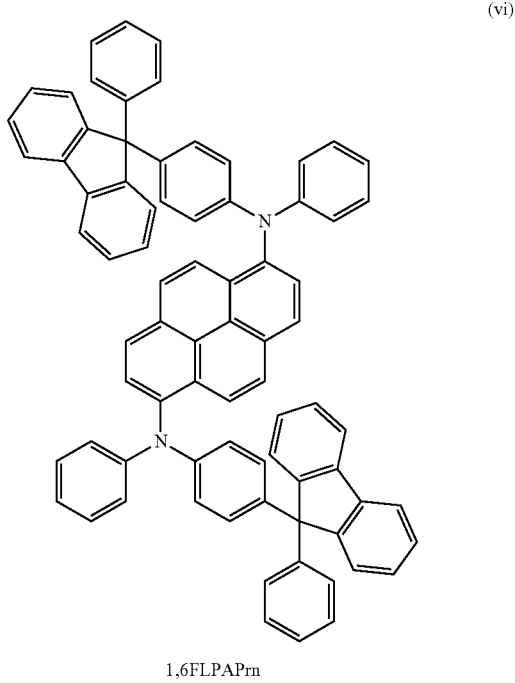 [SMILES: c1ccc(N(c2ccc(C3(c4ccccc4)c4ccccc4-c4ccccc43)cc2)c2ccc3ccc4c(N(c5ccccc5)c5ccc(C6(c7ccccc7)c7ccccc7-c7ccccc76)cc5)ccc5ccc2c3c54)cc1]

1,6FLPAPrn

Step 1: Method of Synthesizing
9-(4-Bromophenyl)-9-phenylfluorene

In a 100-mL three-neck flask, 1.2 g (50 mmol) of magnesium was heated and stirred under reduced pressure for 30 minutes to be activated. The flask was cooled to room temperature and was made to have a nitrogen atmosphere, and then several drops of dibromoethane were added, so that babble and heat generation was confirmed. After 12 g (50 mmol) of 2-bromobiphenyl dissolved in 10 mL of diethyl ether was slowly added dropwise to this mixture, the mixture was stirred for 2.5 hours, so that a Grignard reagent was prepared.

Into a 500-mL three-neck flask were put 10 g (40 mmol) of 4-bromobenzophenone and 100 mL of diethyl ether, and the air in the flask was replaced with nitrogen. After the Grignard reagent which was synthesized in advance was slowly dropped into this mixture, the mixture was stirred and heated under reflux for 9 hours.

After the reaction, this mixture was filtrated to obtain resulting matter. The obtained matter was dissolved in 150 mL of ethyl acetate, and 1M-hydrochloric acid was added to the mixture until it was made acid. After the mixture was made acid, the mixture was stirred for 2 hours. The organic layer of this mixture was washed with water, and dried by addition of magnesium sulfate. This mixture was filtered, and the obtained filtrate was concentrated to give an oily substance.

Into a 500-mL recovery flask were put this oily substance, 50 mL of glacial acetic acid, and 1.0 mL of hydrochloric acid. The mixture was stirred and heated at 130° C. for 1.5 hours under a nitrogen atmosphere.

After the reaction, this reaction mixture was filtrated to obtain resulting matter. The obtained matter was washed with water, an aqueous solution of sodium hydroxide, water, and methanol in this order. Then, the mixture was dried, so that 11 g of white powder which was the objective substance was obtained in 69% yield. The synthesis scheme of Step 1 is shown in (E1-1) below.

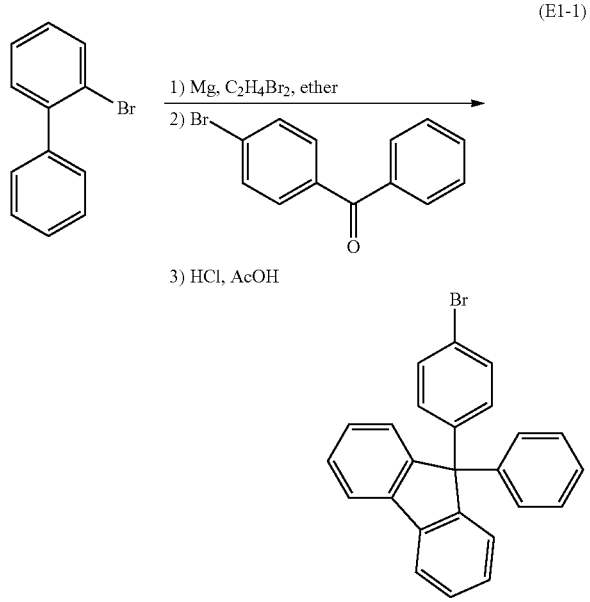

(E1-1)

Step 2: Method of Synthesizing 4-(9-Phenyl-9H-fluoren-9-yl)diphenylamine (abbreviation: FLPA)

Into a 200-mL three-neck flask were put 5.8 g (14.6 mmol) of 9-(4-bromophenyl)-9-phenylfluorene, 1.7 mL (18.6 mmol) of aniline, and 4.2 g (44.0 mmol) of sodium tert-butoxide, and the air in the flask was replaced with nitrogen. To this mixture were added 147.0 mL of toluene and 0.4 mL of a 10% hexane solution of tri(tert-butyl)phosphine. The temperature of this mixture was set to 60° C., and 66.1 mg (0.1 mmol) of bis(dibenzylideneacetone)palladium(0) was added to the mixture, followed by stirring for 3.5 hours. After the stirring, suction filtration through Florisil (produced by Wako Pure Chemical Industries, Ltd., Catalog No. 540-00135), Celite (produced by Wako Pure Chemical Industries, Ltd., Catalog No. 531-16855), and alumina was carried out to obtain a filtrate. The obtained filtrate was concentrated. The obtained filtrate was concentrated to give a solid, which was then purified by silica gel column chromatography (the developing solvent has a 2:1 ratio of hexane to toluene). The obtained fraction was concentrated to give 6.0 g of a white solid which was the objective substance in 99% yield. The synthesis scheme of Step 2 is shown in (E1-2) below.

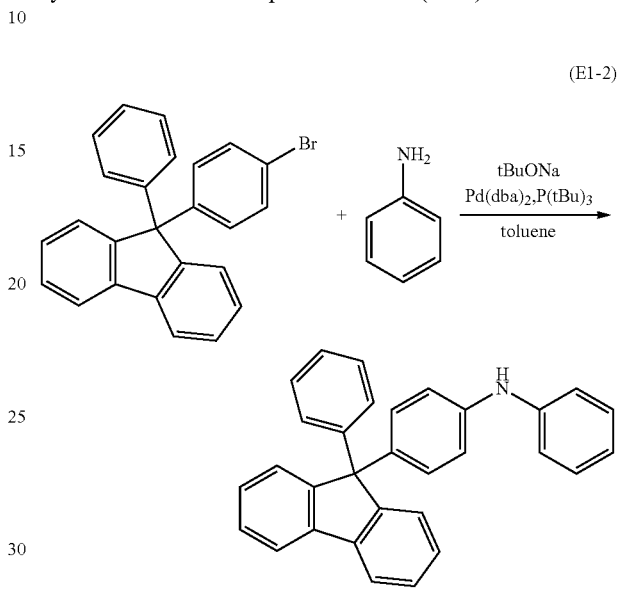

(E1-2)

Step 3: Method of Synthesizing N,N'-Bis[4-(9-phenyl-9H-fluoren-9-yl)phenyl]-N,N'-diphenylpyrene-1,6-diamine (abbreviation: 1,6FLPAPm)

Into a 50 mL three-neck flask were put 0.4 g (1.2 mmol) of 1,6-dibromopyrene, 1.0 g (2.4 mmol) of 4-(9-phenyl-9H-fluoren-9-yl)diphenylamine (abbreviation: FLPA) obtained in Step 2 of Reference Example 1, and 0.3 g (3.6 mmol) of sodium tert-butoxide, and the air in the flask was replaced with nitrogen. To this mixture were added 11.5 mL of toluene and 0.20 mL of a 10% hexane solution of tri(tert-butyl)phosphine. The temperature of this mixture was set to 70° C., and 31.1 mg (0.05 mmol) of bis(dibenzylideneacetone)palladium (0) was added to the mixture, followed by stirring for 4.0 hours. After the stirring, the mixture was suction-filtered through Florisil, Celite, and alumina to give a filtrate. The obtained filtrate was concentrated. The obtained filtrate was concentrated to give a solid, which was then purified by silica gel column chromatography (the developing solvent was chloroform), and the obtained fraction was concentrated to give a yellow solid. The obtained solid was washed with a mixed solvent of toluene and hexane, and then the mixture was suction-filtered to give a yellow solid. The obtained yellow solid was washed with a mixed solvent of chloroform and hexane, so that 0.8 g of a pale yellow powdered solid was obtained in 68% yield.

By a train sublimation method, 0.8 g of the obtained pale yellow solid was purified. Under a pressure of 2.7 Pa with a flow rate of argon at 5.0 mL/min, the purification was carried out at 360° C. After the purification, 0.4 g of the objective substance was obtained in 56% yield. The synthesis scheme of Step 3 is illustrated in (E2-A) below.

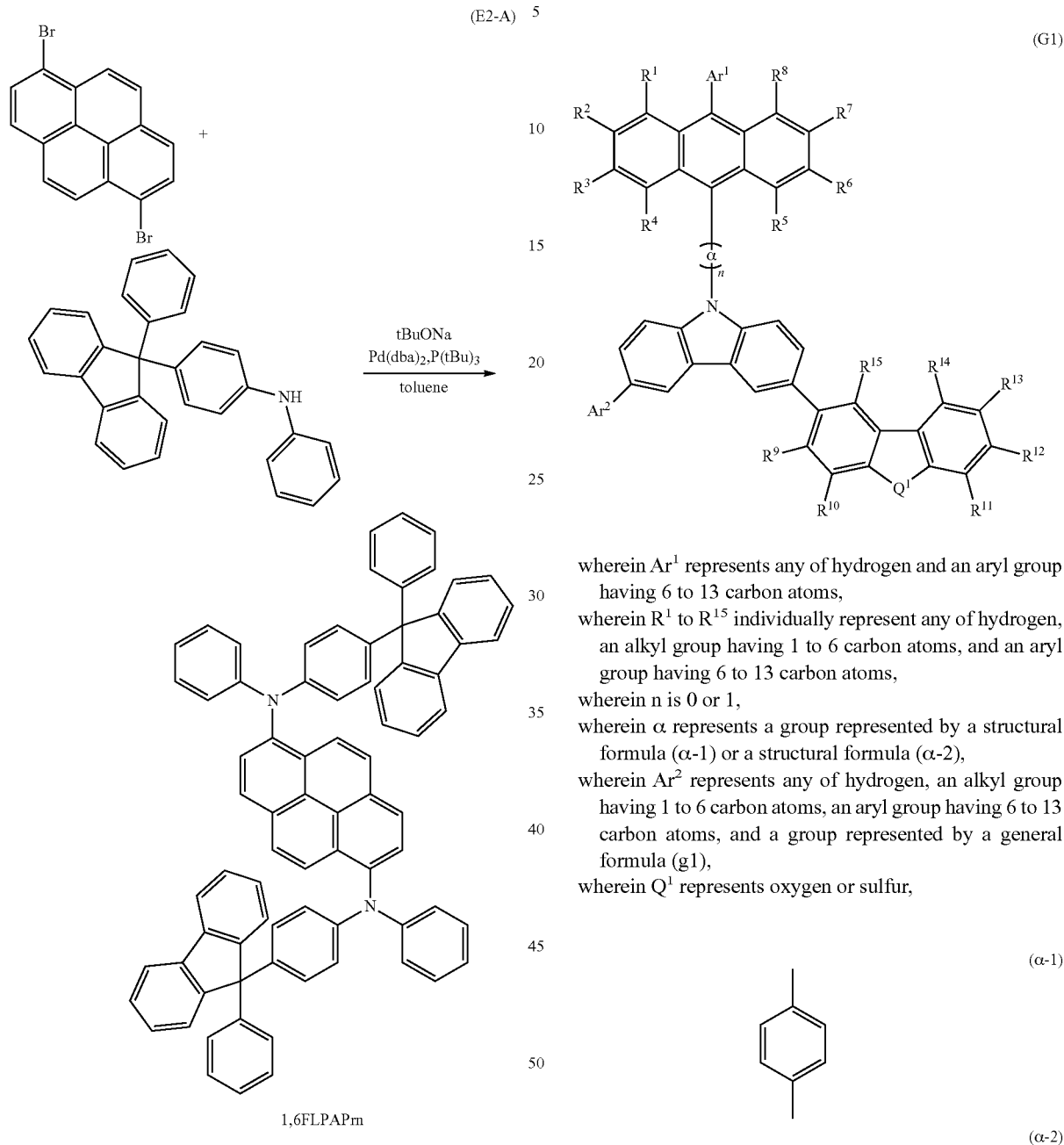

1,6FLPAPrn

A nuclear magnetic resonance (NMR) method and a mass spectrometry identified the obtained compound as N,N'-bis[4-(9-phenyl-9H-fluoren-9-yl)phenyl]-N,N'-diphenylpyrene-1,6-diamine (abbreviation: 1,6FLPAPrn). The $^1$H NMR data are given below.

$^1$H NMR (CDCl$_3$, 300 MHz): δ=6.88-6.91 (m, 6H), 7.00-7.03 (m, 8H), 7.13-7.40 (m, 26H), 7.73-7.80 (m, 6H), 7.87 (d, J=9.0 Hz, 2H), 8.06-8.09 (m, 4H)

This application is based on Japanese Patent Application serial no. 2010-243133 filed with Japan Patent Office on Oct. 29, 2010, the entire contents of which are hereby incorporated by reference.

What is claimed is:
1. A carbazole compound represented by a general formula (G1),

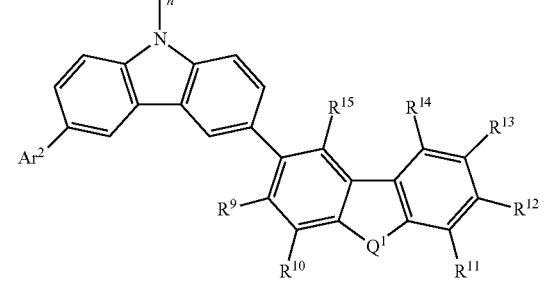

wherein Ar$^1$ represents any of hydrogen and an aryl group having 6 to 13 carbon atoms, wherein R$^1$ to R$^{15}$ individually represent any of hydrogen, an alkyl group having 1 to 6 carbon atoms, and an aryl group having 6 to 13 carbon atoms, wherein n is 0 or 1, wherein α represents a group represented by a structural formula (α-1) or a structural formula (α-2), wherein Ar$^2$ represents any of hydrogen, an alkyl group having 1 to 6 carbon atoms, an aryl group having 6 to 13 carbon atoms, and a group represented by a general formula (g1), wherein Q$^1$ represents oxygen or sulfur,

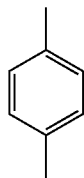

(α-1)

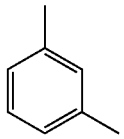

(α-2)

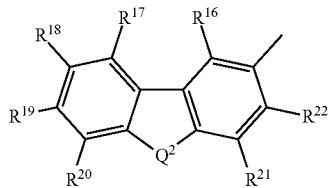

(g1)

wherein $R^{16}$ to $R^{22}$ individually represent any of hydrogen, an alkyl group having 1 to 6 carbon atoms, and an aryl group having 6 to 13 carbon atoms, and wherein $Q^2$ represents oxygen or sulfur.

2. The carbazole compound according to claim 1, wherein $Ar^1$ is a phenyl group, and wherein n is 1.

3. The carbazole compound according to claim 2, wherein $R^1$, $R^4$, $R^5$, $R^8$, $R^9$, $R^{12}$, $R^{14}$, $R^{15}$, $R^{16}$, $R^{17}$, $R^{19}$, and $R^{22}$ represent hydrogen.

4. The carbazole compound according to claim 3, wherein $R^{10}$, $R^{11}$, $R^{13}$, $R^{18}$, $R^{20}$, and $R^{21}$ represent hydrogen.

5. The carbazole compound according to claim 4, wherein $R^2$, $R^3$, $R^6$, and $R^7$ represent hydrogen.

6. The carbazole compound according to claim 2, wherein α is represented by the formula (α-1).

7. The carbazole compound according to claims 6, wherein $R^1$, $R^4$, $R^5$, $R^8$, $R^9$, $R^{12}$, $R^{14}$, $R^{15}$, $R^{16}$, $R^{17}$, $R^{19}$, and $R^{22}$ represent hydrogen.

8. The carbazole compound according to claim 7, wherein $R^{10}$, $R^{11}$, $R^{18}$, $R^{20}$, and $R^{21}$ represent hydrogen.

9. The carbazole compound according to claim 8, wherein $R^2$, $R^3$, $R^6$, and $R^7$ represent hydrogen.

10. The carbazole compound according to claim 9, wherein $Ar^2$ represents hydrogen.

11. The carbazole compound according to claim 10, wherein $Q^2$ represents oxygen.

12. The carbazole compound according to claim 9, wherein $Ar^2$ represents a group represented by a general formula (g3), and

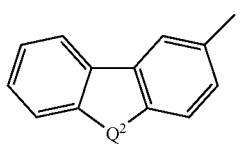

(g3)

wherein $Q^2$ represents oxygen or sulfur.

13. The carbazole compound according to claim 12, wherein $Q^2$ represents sulfur.

14. The carbazole compound according to claim 1, wherein the carbazole compound is included in a light-emitting layer.

15. The carbazole compound according to claim 1, wherein the carbazole compound is included in a carrier-transport layer.

16. An organic semiconductor material comprising the carbazole compound according to claim 1.

17. A light-emitting element comprising:

a pair of electrodes; and a layer comprising a carbazole compound represented by a general formula (G1),

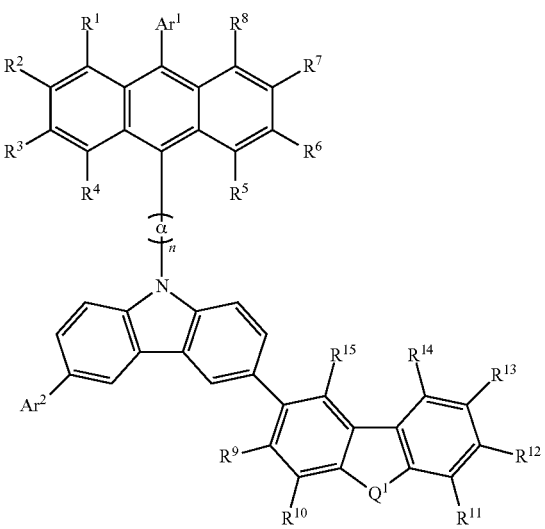

(G1)

wherein $Ar^1$ represents any of hydrogen and an aryl group having 6 to 13 carbon atoms, wherein $R^1$ to $R^{15}$ individually represent any of hydrogen, an alkyl group having 1 to 6 carbon atoms, and an aryl group having 6 to 13 carbon atoms, wherein n is 0 or 1, wherein α represents a group represented by a structural formula (α-1) or a structural formula (α-2), wherein $Ar^2$ represents any of hydrogen, an alkyl group having 1 to 6 carbon atoms, an aryl group having 6 to 13 carbon atoms, and a group represented by a general formula (g1), wherein $Q^1$ represents oxygen or sulfur,

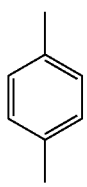

(α-1)

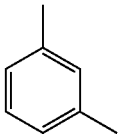

(α-2)

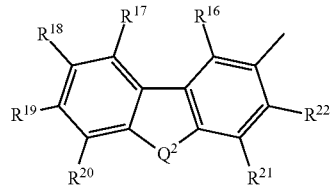

(g1)

wherein $R^{16}$ to $R^{22}$ individually represent any of hydrogen, an alkyl group having 1 to 6 carbon atoms, and an aryl group having 6 to 13 carbon atoms, and wherein $Q^2$ represents oxygen or sulfur.

18. The light-emitting element according to claim 17, wherein $Ar^1$ is a phenyl group, and wherein n is 1.

19. The light-emitting element according to claim 18, wherein $R^1$, $R^4$, $R^5$, $R^8$, $R^9$, $R^{12}$, $R^{14}$, $R^{15}$, $R^{16}$, $R^{17}$, $R^{19}$, and $R^{22}$ represent hydrogen.

20. The light-emitting element according to claim 19, wherein $R^{10}$, $R^{11}$, $R^{13}$, $R^{18}$, $R^{20}$, and $R^{21}$ represent hydrogen.

21. The light-emitting element according to claim 20, wherein $R^2$, $R^3$, $R^6$, and $R^7$ represent hydrogen.

22. The light-emitting element according to claim 18, wherein α is represented by the formula (α-1).

23. The light-emitting element according to claim 22, wherein $R^1$, $R^4$, $R^5$, $R^8$, $R^9$, $R^{12}$, $R^{14}$, $R^{15}$, $R^{16}$, $R^{17}$, $R^{19}$, and $R^{22}$ represent hydrogen.

24. The light-emitting element according to claim 23, wherein $R^{10}$, $R^{11}$, $R^{13}$, $R^{18}$, $R^{20}$, and $R^{21}$ represent hydrogen.

25. The light-emitting element according to claim 24, wherein $R^2$, $R^3$, $R^6$, and $R^7$ represent hydrogen.

26. The light-emitting element according to claim 25, wherein $Ar^2$ represents hydrogen.

27. The light-emitting element according to claim 26, wherein $Q^2$ represents oxygen.

28. The light-emitting element according to claim 25, wherein $Ar^2$ represents a group represented by a general formula (g3), and

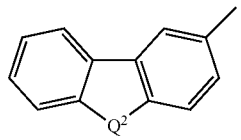

(g3)

wherein $Q^2$ represents oxygen or sulfur.

29. The light-emitting element according to claim 28, wherein $Q^2$ represents sulfur.

30. The light-emitting element according to claim 17, wherein the layer is a light-emitting layer.

31. The light-emitting element according to claim 17, wherein the layer is a carrier-transport layer.

32. A light-emitting device comprising the light-emitting element according to claim 17.

33. A lighting device comprising the light-emitting element according to claim 17.

34. An electronic device comprising the light-emitting element according to claim 17.

* * * * *

UNITED STATES PATENT AND TRADEMARK OFFICE
CERTIFICATE OF CORRECTION

PATENT NO. : 9,150,551 B2
APPLICATION NO. : 13/282722
DATED : October 6, 2015
INVENTOR(S) : Hiroki Suzuki et al.

It is certified that error appears in the above-identified patent and that said Letters Patent is hereby corrected as shown below:

In the Specification:

Column 4, Line 26; Change "group, represented" to --group represented--.

Column 40, Line 25; Change "high, hole-transport" to --high hole-transport--.

Column 40, Line 50; Change "bipheriyl" to --biphenyl--.

Column 42, Lines 8 to 9; Change "poly(-vinyltiphenylamine)" to --poly(4-vinyltriphenylamine)--.

Column 42, Line 37; Change "the N,N'-bis" to --the following. N,N'-bis--.

Column 42, Line 53; Change "N''',N'''" to --N''',N''''--.

Column 42, Line 60; Change "N,N,N" to --N,N',N'--.

Column 42, Line 65; Change "N,N" to --N,N'--.

Column 43, Line 13; Change "benzo    quinolizin-9-yl)" to --benzo[ij]quinolizin-9-yl)--.

Column 43, Line 14; Change "ylidenel}" to --ylidene}--.

Column 45, Line 45; Change "funned" to --formed--.

Column 50, Line 67; Change "described Embodiment 1," to --described in Embodiment 1,--.

Column 61, Line 21; Change "$E_{pa}$" to --$E_{pc}$--.

Column 61, Line 22; Change "$E_{pa}$ and $E_{pa}$)" to --$E_{pa}$ and $E_{pc}$)--.

Column 64, Line 53; Change "foliated." to --formed.--.

Column 64, Lines 56 to 57; Change "formula (II)" to --formula (ii)--.

Column 64, Line 57; Change "1,6FLPAPm" to --1,6FLPAPrn--.

Column 68, Line 37; Change "1,6FLPAPm)" to --1,6FLPAPrn--.

Signed and Sealed this
Twenty-third Day of August, 2016

Michelle K. Lee
*Director of the United States Patent and Trademark Office*